US006831193B2

(12) United States Patent
Lee et al.

(10) Patent No.: US 6,831,193 B2
(45) Date of Patent: Dec. 14, 2004

(54) TRISUBSTITUTED-N-[(1S)-1,2,3,4-TETRAHYDRO-1-NAPHTHALENYL] BENZAMIDES WHICH INHIBIT P2X₃ AND P2X$_{2/3}$ CONTAINING RECEPTORS

(75) Inventors: Chih-Hung Lee, Vernon Hills, IL (US); Richard J. Perner, Gurnee, IL (US); Daniel P. Larson, Highland Park, IL (US); John R. Koenig, Chicago, IL (US); Arthur R. Gomtsyan, Vernon Hills, IL (US); Guo Zhu Zheng, Lake Bluff, IL (US); Stanley DiDomenico, Richmond, IL (US); Andrew O. Stewart, Libertyville, IL (US); Erol K. Bayburt, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 188 days.

(21) Appl. No.: 10/141,989

(22) Filed: May 10, 2002

(65) Prior Publication Data

US 2003/0083359 A1 May 1, 2003

Related U.S. Application Data

(60) Provisional application No. 60/291,823, filed on May 18, 2001.

(51) Int. Cl.⁷ .......................................... C07C 229/00
(52) U.S. Cl. .................... 560/563; 560/41; 564/123; 564/161; 514/408
(58) Field of Search .............. 560/41, 563; 514/408; 564/123, 161

(56) References Cited

FOREIGN PATENT DOCUMENTS

| WO | 96/34851 | 7/1996 |
|---|---|---|
| WO | WO 9634851 | * 11/1996 |
| WO | 98/47869 | 10/1998 |

OTHER PUBLICATIONS

Virginio et al., "Trinitrophenyl–substituted nucleotides are potent antagonists selective for P2X₁, P2X₃, and heteromeric PX2$_{2/3}$ receptors," Molecular Pharmacology 53(6):969–973 (1998).
Abbott et al. "The formalin test: scoring properties fo the first and second phases of the pain response in rats", Pain 60:91–102 (1995).
Berge, J. Pharmaceutical Sciences 66:1 et seq. (1977).
Bianchi et al., "Pharmacological characterization of recombinant human and rat P2X receptor subtypes", European Journal of Pharmacology 376:127–138 (1999).
Bland–Ward et al., Acute nociception mediated y hindpay P2X receptor activation in the rat,: Br. J. Pharmacol 122:365–371 (1997).
Bleehen, "The effects of adenine nucleotides on cutaneous afferent nerve activity", Br. J. Pharmacol 62:573–577 (1978).
Boeckmann et al., Chem. Ber. 110:703 (1977).

Brake et al., "New structural motif for ligand–gated ion channels defined by an ionotopical ATP receptor", Nature 371:519–523 (1994).
Cesare et al, Drug Dev. Res. 50:S01–02 (2000).
Chen et al., "A purinoceptor expressed by a subset of sensory neurons", Nature 377:428–430 (1995).
Cockayne et al., Drug Dev. Res. 50:005 (2000).
Cook et al., "Distinct ATP receptors on pain–sensing and stretch–sensing neurons", Nature 387:505–508 (1997).
Ding et al., "Single channel properties of P2X2 purinoceptors," J. Gen Physiol 113:695–719 (1999).
Driessen et al., "Modulation of neural noradrealine and ATP release by angiotensin II and prostaglandin E₂ in guinea–pig vas deferens", Naunyn Schmiedebergs Arch Pharmacol 350:618–625 (1994).
Gu et al., "Activation of ATP P2X receptors elicits glutamate release from sensory neuron synapses", Nature 389:749–753 (1997).
Hamilton et al, "The effects of inflammation and inflammatory mediators on nociceptive behavior induced by ATP analogues in the rat," Br. J. Pharmacol 126:326–332 (1999).
Holton and Holton, "The capillary dilator substance in dry powders of spinal roots; a possible role of adenosine triphosphate in chemical transmission from nerve endings", J. Physiol (Lond) 126:124–140 (1954).
Le et al., "Central P2X₄ and P2X₆ channel subunits coassemble into a novel heteromeric ATP receptor", The Journal of Neuroscience 18:7152–7159 (1998).
Lewis et al, "Coexpression of P2X₂ and P2X₃ receptor subunits can account for ATP–gated currents in sensory neurons", Nature 377:432–435 (1995).

(List continued on next page.)

Primary Examiner—Alan L. Rotman
Assistant Examiner—Hector M. Reyes
(74) Attorney, Agent, or Firm—Johanna M. Corbin; Michael J. Ward

(57) ABSTRACT

Compounds of formula (I)

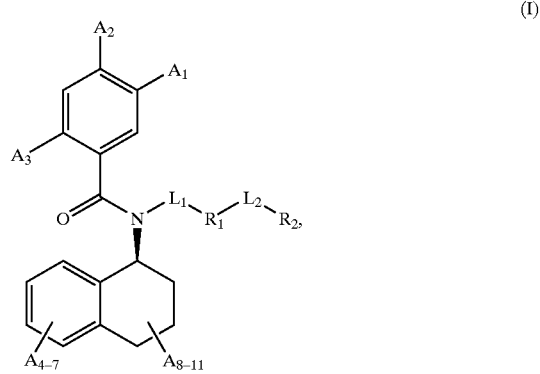

(I)

are novel P2X₃ and P2X₂/P2X₃ antagonists which are useful in treating pain, urinary incontinence and bladder overactivity.

68 Claims, No Drawings-

OTHER PUBLICATIONS

Namasivayam et al., "Purinergic sensory neurotransmission in the urinary bladder: an invitro study in the rat", Brit J. Urol Int. 84L:854–860 (1999).

Novakovic et al., "Immunocytochemical localization of P2X3 purinoceptors in sensory neurons in naïve rats and following neuropathic injury," Pain 80:273–282 (1999).

Prescott et al., Methods in Cell Biology, Academic Press, New York 14:33 et seq. (1976).

Ralevic and Burnstock, "Receptors for purines and pyrimidines," Pharmacol. Rev 50:413–492 (1998).

Saccomano et al., "Calcium–independent phosphodiesterase inhibitors as putative antidepressants: [3–(bicycloalkyloxy)–4–methoxyphenyl]–2–imidazolidinones", J. Med. Chem. 34:291–298 (1991).

Simon et al., "Localization and functional expression of splice variants of the $P2X_2$ receptor", Molecular Pharmacology 52:237–248 (1997).

Tanaka et al., "Inhibitors of acyl–coa: cholesterol O–acyltransferase:–3–discovery of a novel series of n–alkyl–n[(fluorophenoxy)benyl]–n–arylureas with weak toxicological effects on adrenal glands", J. Med. Chem. 41:4408–4420 (1998).

Thomas et al., "The antagonist trinitrophenyl–ATP reveals co–existence of distinct P2X receptor channels in rat nodose neurons", J. Physiol (Lond) 509(Pt. 2):411–417 (1998).

Torres et al., "Co–expression of $P2X_1$ and $P2X_5$ receptor subunits reveals a novel ATP–gated ion chennel", Molecular Pharmacology 54:989–993 (1998).

Tsuda et al., "In vivo pathway of thermal hyperalgesia by intrathecal administration of—methylene ATP in mouse spinal cord: involvement of the glutamate–NMDA receptor system," Br. J. Pharamcol 127:449–456 (1999).

Virginio et al., "Calcium permeability and block at homomeric and hetermeric $P2X_2$ and $P2_3$ receptors, and P2X receptors in rat nodose neurons", Journal of Physiology (Lond) 510(1):27–35 (1998).

Vulchanova et al., "Immunohistochemical study of the $P2X_2$ and $P2X_3$ receptor subunits in rat and monkey sensory neurons and their central terminals", Neuropharmacology 36(9):1229–1242 (1997).

Vulchanova et al., "Differential distribution of two ATP–gated ion channels ($P_{2x}$receptors) determined by immunocytochemistry", Proc Natl Acad Sci USA 93:8063–8067 (1996).

* cited by examiner

TRISUBSTITUTED-N-[(1S)-1,2,3,4-TETRAHYDRO-1-NAPHTHALENYL] BENZAMIDES WHICH INHIBIT P2X$_3$ AND P2X$_{2/3}$ CONTAINING RECEPTORS

This application claims priority to U.S. Provisional application Ser. No. 60/291,823, filed May 18, 2001.

TECHNICAL FIELD

The present invention relates to compounds of formula (I), which are useful for treating diseases or conditions caused by or exacerbated by P2X receptor activity, pharmaceutical compositions containing compounds of formula (I) and methods of treatment using compounds of formula (I).

BACKGROUND OF THE INVENTION

P2X receptors function as homomultimeric cation-permeable ion channels and, in some cases, as heteromeric channels consisting of two different P2X receptor subtypes ((Lewis et al., Nature 377:432–435 (1995); Le et al., The Journal of Neuroscience, 18 (1998) 7152–7159, Torres et al., Molecular Pharmacology, 54 (1998) 989–993). At least one pair of P2X receptor subtypes, P2X$_2$ and P2X$_3$, functions as a heteromeric channel in rat nodose ganglion neurons where it exhibits distinct pharmacological and electrophysiological properties (Lewis et al., Nature 377:432–435 1995).

With respect to individual receptors, the rat P2X$_2$ containing receptor is expressed in the spinal cord, and in the nodose and dorsal root ganglia (Brake et al., Nature 371:519–523 (1994)), while rat P2X$_3$ containing receptor expression is found primarily in a subset of neurons of the sensory ganglia (Chen et al., Nature 377:428–430 (1995); Vulchanova et al., Neuropharmacol. 36:1229–1242 (1997)). The distribution of both receptors is consistent with a role in pain transmission. The P2X$_2$ and P2X$_3$ subunits form functional channels when expressed alone, and can also form a functional heteromultimeric channel that has properties similar to currents seen in native sensory channels when co-expressed (Lewis et al., Nature 377:432–435 (1995)). Evidence from studies in rat nodose ganglia indicate that both P2X$_2$/P2X$_3$ heteromeric channels and P2X$_2$ homomeric channels contribute to adenosine triphosphate-induced currents (Virginio et al., J Physiol (Lond) 510:27–35 (1998); Thomas et al., J Physiol (Lond) 509 (Pt 2):411–417 (1998)); Vulchanova et al., Proc Natl Acad Sci U S A 93:8063–8067 (1996);; Simon et al., Mol Pharmacol 52:237–248 (1997)).

ATP, which activates P2X$_2$, P2X$_3$, and P2X$_2$/P2X$_3$ containing receptors, functions as an excitatory neurotransmitter in the spinal cord dorsal horn and in primary afferents from sensory ganglia (Holton and Holton, J. Physiol. (Lond.) 126:124–140 (1954)). ATP-induced activation of P2X receptors on dorsal root ganglion nerve terminals in the spinal cord stimulates the release of glutamate, a key neurotransmitter involved in nociceptive signaling (Gu and MacDermott, Nature 389:749–753 (1997)). Thus, ATP released from damaged cells can evoke pain by activating P2X$_2$, P2X$_3$, or P2X$_2$/P2X$_3$ containing receptors on nociceptive nerve endings of sensory nerves. This is consistent with the induction of pain by intradermally applied ATP in the human blister-base model (Bleehen, Br J Pharmacol 62:573–577 (1978)); the identification of P2X$_3$ containing receptors on nociceptive neurons in the tooth pulp (Cook et al., Nature 387:505–508 (1997)); and with reports that P2X antagonists are analgesic in animal models (Driessen and Starke, Naunyn Schmiedebergs Arch Pharmacol 350:618–625 (1994)). This evidence suggests that P2X$_2$ and P2X$_3$ function in nociception, and that modulators of these human P2X receptors are useful as analgesics.

It has been recently demonstrated that P2X$_3$ receptor gene disruption results in a diminished sensitivity to noxious chemical stimuli and reduced pain (Cesare et al., Drug Dev. Res. 50: S01–02 (2000); Cockayne et al., Drug Dev. Res. 50: 005 (2000)). P2X$_3$ containing receptor knock-out mice also exhibited a marked urinary bladder hyporeflexia upon cystometric evaluation, suggesting that P2X$_3$ antagonists have utility for treating bladder overactivity. P2X$_3$ knock-out mice had decreased voiding frequency, increased voiding volume, but normal bladder pressure. It has been proposed that ATP acts as a physiological regulator of sensory neurotransmission in visceral hollow organs such as bladder (Namasivayam et al., Brit. J. Urol. Int. 84L 854–860. (1999), and P2X$_3$ containing receptors localized on the basal surface of the urothelium. The urology data on the P2X$_3$ knock-out mice suggest that P2X$_3$ plays a major role in modulating the volume threshold for activation of micturition and that P2X$_3$ antagonists have therapeutic utility for urinary incontinence.

The nociceptive effects of exogenously administered ATP and P2X containing receptor agonists have also been demonstrated in laboratory animals (Bland-Ward and Humphrey, 1997; Hamilton et al., 1999). The peripheral nociceptive actions of P2X activation and stimulation of spinal P2X containing receptors also contribute to nociception as indicated by the ability of intrathecally (i.t.) administered P2 receptor agonists to increase sensitivity to acute and persistent noxious stimuli in rodents (Driessen et al., 1994; Tsuda et al., 1999a; 1999b).

The utility of available purinergic ligands to evaluate the role of individual P2 receptor subtypes in mammalian physiology has been complicated by the susceptibility of P2 receptor agonists to undergo enzymatic degradation, and by the lack of P2 receptor subtype-selective agonists and antagonists (King et al., 1999; Ralevic and Burnstock, 1998).

Since subtype-selective ligands for the individual P2 receptors have yet to be identified, efforts to elucidate the specific P2X containing receptor subtypes involved in the transmission of nociceptive signals has been largely based on receptor localization and functional studies using immunohistochemical techniques. These studies have shown that both the homomeric P2X$_3$ and heteromeric P2X$_{2/3}$ containing receptor subtypes are selectively localized to the central and peripheral terminals of small diameter sensory neurons (Chen et al., 1995; Lewis et al., 1995; Vulchanova et al., 1997; 1998). Further, recent data has shown that P2X$_3$ specific immunoreactivity is significantly increased in both the injured dorsal root ganglion and in the ipsalateral spinal dorsal horn following chronic constriction injury of the rat sciatic nerve (Novakovic et al., 1999).

The functional and immunohistochemical localization of P2X$_3$ and/or P2X$_{2/3}$ containing receptors on sensory nerves indicates that these P2X containing receptors have a primary role in mediating the nociceptive effects of exogenous ATP. Thus, compounds which block or inhibit activation of P2X$_3$ containing receptors serve to block the pain stimulus. Antagonists of the P2X$_3$ homomeric channel and/or the P2X$_2$/P2X$_3$ heteromeric channel could successfully block the transmission of pain.

The compounds of the present invention are novel P2X$_3$ and P2X$_{2/3}$ antagonists, having utility in treating pain as well as in treating bladder overactivity and urinary incontinence.

SUMMARY OF THE INVENTION

The present invention discloses trisubstituted-N-[(1S)-1, 2,3,4-tetrahydro-1-naphthalenyl]benzamides compounds, a method for controlling pain in mammals, and pharmaceutical compositions including those compounds. More particularly, the present invention is directed to compounds of formula (I):

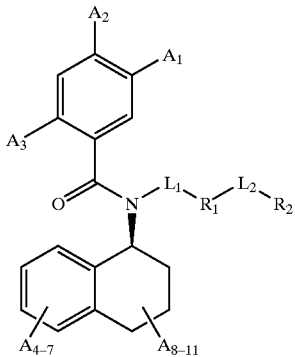

or pharmaceutically acceptable salts or prodrugs thereof, wherein $A_1$ and $A_2$ are each independently selected from alkoxycarbonyl, alkylcarbonyloxy, carboxy, hydroxy, hydroxyalkyl, $(NR_AR_B)$carbonyl, $(NR_CS(O)_2R_D)$carbonyl, —S(O)$_2$OH, or tetrazolyl; or $A_1$ and $A_2$ together with the carbon atoms to which they are attached form a five membered heterocycle containing a sulfur atom wherein the five membered heterocycle is optionally substituted with 1 or 2 substituents selected from mercapto or oxo;

$A_3$ is selected from alkoxycarbonyl, alkylcarbonyloxy, carboxy, hydroxy, hydroxyalkyl, $(NR_AR_B)$carbonyl, $(NR_CS(O)_2R_D)$carbonyl, —S(O)$_2$OH, or tetrazolyl;

$A_4$, $A_5$, $A_6$ and $A_7$ are each independently selected from hydrogen, alkoxy, alkoxycarbonyl, alkenyl, alkyl, alkylcarbonyl, alkylcarbonyloxy, alkynyl, aryl, carboxy, cyano, haloalkoxy, haloalkyl, halogen, heterocycle, hydroxy, hydroxyalkyl, nitro, —NR$_E$R$_F$, or $(NR_ER_F)$carbonyl;

$A_8$, $A_9$, $A_{10}$ and $A_{11}$ are each independently selected from hydrogen, alkoxy, alkoxycarbonyl, alkenyl, alkyl, alkylcarbonyl, alkylcarbonyloxy, alkynyl, aryl, carboxy, haloalkoxy, haloalkyl, halogen, heterocycle, hydroxy, hydroxyalkyl, —NR$_E$R$_F$, $(NR_ER_F)$carbonyl, or oxo;

$R_A$ and $R_B$ are each independently selected from hydrogen, alkyl, or cyano;

$R_C$ is selected from hydrogen or alkyl;

$R_D$ is selected from alkoxy, alkyl, aryl, arylalkoxy, arylalkyl, haloalkoxy, or haloalkyl;

$R_E$ and $R_F$ are each independently selected from hydrogen, alkyl, alkylcarbonyl, formyl, or hydroxyalkyl;

$L_1$ is selected from alkenylene, alkylene, alkynylene, —(CH$_2$)$_m$O(CH$_2$)$_n$—, —(CH$_2$)$_m$S(CH$_2$)$_n$—, or —(CH$_2$)$_p$C(O)(CH$_2$)$_q$— wherein each group is drawn with the left end attached to N and the right end attached to $R_1$;

m is an integer 0–10;

n is an integer 0–10;

$R_1$ is selected from aryl, cycloalkenyl, cycloalkyl, or heterocycle;

$L_2$ is absent or selected from a covalent bond, alkenylene, alkylene, alkynylene, —(CH$_2$)$_p$O(CH$_2$)$_q$—, (CH$_2$)$_p$S(CH$_2$)$_q$—, (CH$_2$)$_p$C(O)(CH$_2$)$_q$—, or —(CH$_2$)$_p$CH=NO(CH$_2$)$_q$— wherein each group is drawn with the left end attached to $R_1$ and the right end attached to $R_2$;

p is an integer 0–10;

q is an integer 0–10; and $R_2$ is absent or selected from aryl, cycloalkenyl, cycloalkyl, or heterocycle.

DETAILED DESCRIPTION OF THE INVENTION

The principle embodiment of the present invention is directed to compounds of formula (I):

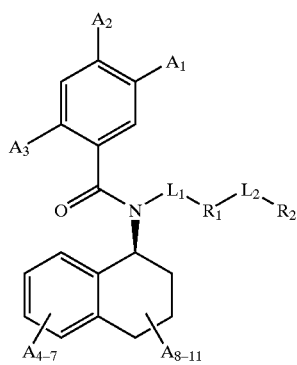

or pharmaceutically acceptable salts or prodrugs thereof, wherein $A_1$ and $A_2$ are each independently selected from alkoxycarbonyl, alkylcarbonyloxy, carboxy, hydroxy, hydroxyalkyl, $(NR_AR_B)$carbonyl, $(NR_CS(O)_2R_D)$carbonyl, —S(O)$_2$OH, or tetrazolyl;

or $A_1$ and $A_2$ together with the carbon atoms to which they are attached form a five membered heterocycle containing a sulfur atom wherein the five membered heterocycle is optionally substituted with 1 or 2 substituents selected from mercapto or oxo;

$A_3$ is selected from alkoxycarbonyl, alkylcarbonyloxy, carboxy, hydroxy, hydroxyalkyl, $(NR_AR_B)$carbonyl, $(NR_CS(O)_2R_D)$carbonyl, —S(O)$_2$OH, or tetrazolyl;

$A_4$, $A_5$, $A_6$ and $A_7$ are each independently selected from hydrogen, alkoxy, alkoxycarbonyl, alkenyl, alkyl, alkylcarbonyl, alkylcarbonyloxy, alkynyl, aryl, carboxy, cyano, haloalkoxy, haloalkyl, halogen, heterocycle, hydroxy, hydroxyalkyl, nitro, —NR$_E$R$_F$, or $(NR_ER_F)$carbonyl;

$A_8$, $A_9$, $A_{10}$ and $A_{11}$ are each independently selected from hydrogen, alkoxy, alkoxycarbonyl, alkenyl, alkyl, alkylcarbonyl, alkylcarbonyloxy, alkynyl, aryl, carboxy, haloalkoxy, haloalkyl, halogen, heterocycle, hydroxy, hydroxyalkyl, —NR$_E$R$_F$, $(NR_ER_F)$carbonyl, or oxo;

$R_A$ and $R_B$ are each independently selected from hydrogen, alkyl, or cyano;

$R_C$ is selected from hydrogen or alkyl;

$R_D$ is selected from alkoxy, alkyl, aryl, arylalkoxy, arylalkyl, haloalkoxy, or haloalkyl;

$R_E$ and $R_F$ are each independently selected from hydrogen, alkyl, alkylcarbonyl, formyl, or hydroxyalkyl;

$L_1$ is selected from alkenylene, alkylene, alkynylene, —$(CH_2)_mO(CH_2)_n$—, —$(CH_2)_mS(CH_2)_n$—, or —$(CH_2)_pC(O)(CH_2)_q$— wherein each group is drawn with the left end attached to N and the right end attached to $R_1$;

m is an integer 0–10;

n is an integer 0–10;

$R_1$ is selected from aryl, cycloalkenyl, cycloalkyl, or heterocycle;

$L_2$ is absent or selected from a covalent bond, alkenylene, alkylene, alkynylene, —$(CH_2)_pO(CH_2)_q$—, —$(CH_2)_pS(CH_2)_q$—, —$(CH_2)_pC(O)(CH_2)_q$—, or —$(CH_2)_pCH=NO(CH_2)_q$— wherein each group is drawn with the left end attached to $R_1$ and the right end attached to $R_2$;

p is an integer 0–10;

q is an integer 0–10; and $R_2$ is absent or selected from aryl, cycloalkenyl, cycloalkyl, or heterocycle.

In another embodiment, compounds of the present invention have formula (I) wherein $A_1$ and $A_2$ are each independently selected from alkoxycarbonyl, carboxy, hydroxy, $(NR_AR_B)$carbonyl, $(NR_CS(O)_2R_D)$carbonyl, and —$S(O)_2OH$; $A_3$ is carboxy; $A_4$, $A_5$, $A_6$, $A_7$, $A_8$, $A_9$, $A_{10}$ and $A_{11}$ are each hydrogen; $R_A$ and $R_B$ are each independently selected from hydrogen, alkyl, and cyano; $L_1$ is selected from alkylene and —$(CH_2)_mO(CH_2)_n$—; $R_1$ is selected from aryl, cycloalkyl and heterocycle; $L_2$ is absent or selected from a covalent bond, alkylene, —$(CH_2)_pO(CH_2)_q$—, —$(CH_2)_pC(O)(CH_2)_q$—, $(CH_2)_pC(OH)(CH_2)_q$—, —$(CH_2)_pS(CH_2)_q$—, and —$(CH_2)_pCH=NO(CH_2)_q$—; P is 0; q is an integer 0–1; $R_2$ is absent or selected from aryl, cycloalkenyl, cycloalkyl and heterocycle; and $R_C$ and $R_D$ are as defined in formula (I).

In another embodiment, compounds of the present invention have formula (I) wherein $A_1$ and $A_2$ together with the carbon atoms to which they are attached form a five membered heterocycle containing a sulfur atom wherein the five membered heterocycle is optionally substituted with 1 or 2 substituents selected from mercapto and oxo; and $A_3$, $A_4$, $A_5$, $A_6$, $A_7$, $A_8$, $A_9$, $A_{10}$, $A_{11}$, $L_1$, $R_1$, $L_2$ and $R_2$ are as defined in formula (I).

In another embodiment, compounds of the present invention have formula (I) wherein $L_1$ is alkylene; $R_1$ is aryl; $L_2$ is absent; $R_2$ is absent; and $A_1$, $A_2$, $A_3$, $A_4$, $A_5$, $A_6$, $A_7$, $A_8$, $A_9$, $A_{10}$ and $A_{11}$ are as defined in formula (I).

In another embodiment, compounds of the present invention have formula (I) wherein $L_1$ is alkylene; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, $(NR_ER_F)$carbonyl, —$N(R_A)C(O)NR_BR_C$, or —$CH=NOR_{EE}$; $L_2$ is absent; $R_2$ is absent; and $R_A$, $R_B$, $R_C$, $R_E$, $R_F$, $R_{EE}$, $A_1$, $A_2$, $A_3$, $A_4$, $A_5$, $A_6$, $A_7$, $A_8$, $A_9$, $A_{10}$ and $A_{11}$ are as defined in formula (I).

In another embodiment, compounds of the present invention have formula (I) wherein $A_1$, $A_2$ and $A_3$ are each carboxy; $A_4$, $A_5$, $A_6$, $A_7$, $A_8$, $A_9$, $A_{10}$ and $A_{11}$ are each hydogen; $L_1$ is alkylene wherein said is alkylene selected from —$CH_2$—, —$CH_2CH_2$— and —$CH_2CH(CH_3)$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, or —$NR_ER_F$; $L_2$ is absent; and $R_2$ is absent; and $R_E$, $R_F$, and $R_{EE}$ are as defined as in formula (I).

In another embodiment, compounds of the present invention have formula (I) wherein $L_1$ is alkylene; $R_1$ is aryl wherein said aryl is fluorenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxy, hydroxyalkyl, nitro, oxo, or —$NR_ER_F$; $L_2$ is absent; $R_2$ is absent; and $R_E$, $R_F$, $A_1$, $A_2$, $A_3$, $A_4$, $A_5$, $A_6$, $A_7$, $A_8$, $A_9$, $A_{10}$ and $A_{11}$ are as defined in formula (I).

In another embodiment, compounds of the present invention have formula (I) wherein $A_1$, $A_2$ and $A_3$ are each carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is fluorenyl substituted with 0 or 1 substituent selected from hydroxy and oxo; $L_2$ is absent; and $R_2$ is absent.

In another embodiment, compounds of the present invention have formula (I) wherein $L_1$ is alkylene; $R_1$ is aryl; $L_2$ is a covalent bond; $R_2$ is aryl; and $A_1$, $A_2$, $A_3$, $A_4$, $A_5$, $A_6$, $A_7$, $A_8$, $A_9$, $A_{10}$ and $A_{11}$ are as defined in formula (I).

In another embodiment, compounds of the present invention have formula (I) wherein $L_1$ is alkylene; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, $(NR_ER_F)$carbonyl, —$N(R_A)C(O)NR_BR_C$, or —$CH=NOR_{EE}$; $L_2$ is a covalent bond; $R_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, $(NR_ER_F)$carbonyl, —$N(R_A)C(O)NR_BR_C$, or —$CH=NOR_{EE}$; and $R_A$, $R_B$, $R_C$, $R_E$, $R_F$, $R_{EE}$, $A_1$, $A_2$, $A_3$, $A_4$, $A_5$, $A_6$, $A_7$, $A_8$, $A_9$, $A_{10}$ and $A_{11}$ are each hydrogen; $L_1$ is In another embodiment, compounds of the present invention have formula (I) wherein $A_1$, $A_2$ and $A_3$ are each carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, or —$NR_ER_F$; $L_2$ is a covalent bond; and $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, or —$NR_ER_F$; and $R_E$, $R_F$, and $R_{EE}$ are as defined as in formula (I).

In another embodiment, compounds of the present invention have formula (I) wherein $A_1$ and $A_2$ together with the carbon atoms to which they are attached form a five membered heterocycle containing a sulfur atom wherein the five membered heterocycle is substituted with 0, 1, or 2 substituents selected from mercapto and oxo; $A_3$ is carboxy; $A_4$, $A_5$, $A_6$, $A_7$, $A_8$, $A_9$, $A_{10}$, and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; $L_2$ is a covalent bond; $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; and $R_E$, $R_F$, and $R_{EE}$ are as defined as in formula (I).

In another embodiment, compounds of the present invention have formula (I) wherein $L_1$ is alkylene; $R_1$ is aryl; $L_2$ is a covalent bond; $R_2$ is heterocycle; and $A_1, A_2, A_3, A_4, A_5, A_6, A_7, A_8, A_9, A_{10}$ and $A_{11}$ are as defined in formula (I).

In another embodiment, compounds of the present invention have formula (I) wherein $L_1$ is alkylene; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, or —CH=$NOR_{EE}$; $L_2$ is a covalent bond; $R_2$ is heterocycle wherein said heterocycle is selected from azetidinyl, azepanyl, aziridinyl, furyl, morpholinyl, piperazinyl, piperidinyl, pyrazinyl, pyridazinyl, pyridinyl, pyrimidinyl, pyrrolidinyl and thienyl wherein said heterocycle is substituted with 0, 1, 2, or 3 substituents independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, arylalkoxycarbonyl, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, or —CH=$NOR_{EE}$; and $R_A$, $R_B$, $R_C$, $R_E$, $R_F$, $R_{EE}$, $A_1, A_2, A_3, A_4, A_5, A_6, A_7, A_8, A_9, A_{10}$ and $A_{11}$ are as defined in formula (I).

In another embodiment, compounds of the present invention have formula (I) wherein $A_1$, $A_2$ and $A_3$ are each carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; $L_2$ is a covalent bond; and $R_2$ is heterocycle wherein said heterocycle is selected from pyridinyl, pyrrolidinyl, and thienyl wherein said heterocycle is substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, nitro, —$N(R_A)C(O)NR_BR_C$, or —$NR_ER_F$; and $R_A$, $R_B$, $R_C$, $R_E$, $R_F$, $R_{EE}$ are as defined in formula (I).

In another embodiment, compounds of the present invention have formula (I) wherein $L_1$ is alkylene; $R_1$ is aryl; $L_2$ is alkylene; $R_2$ is aryl; and $A_1, A_2, A_3, A_4, A_5, A_6, A_7, A_8, A_9, A_{10}$ and $A_{11}$ are as defined in formula (I).

In another embodiment, compounds of the present invention have formula (I) wherein $L_1$ is alkylene; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, or —CH=$NOR_{EE}$; $L_2$ is alkylene; $R_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, or —CH=$NOR_{EE}$; and $R_A$, $R_B$, $R_C$, $R_E$, $R_F$, $R_{EE}$, $A_1, A_2, A_3, A_4, A_5, A_6, A_7, A_8, A_9, A_{10}$ and $A_{11}$ are as defined in formula (I).

In another embodiment, compounds of the present invention have formula (I) wherein $A_1$, $A_2$ and $A_3$ are each carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; $L_2$ is alkylene wherein said alkylene is —$CH_2$—; and $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; and $R_E$, $R_F$, and $R_{EE}$ are as defined in formula (I).

In another embodiment, compounds of the present invention have formula (I) wherein $L_1$ is alkylene; $R_1$ is aryl; $L_2$ is —$(CH_2)_pO(CH_2)_q$—; $R_2$ is aryl; and $A_1, A_2, A_3, A_4, A_5, A_6, A_7, A_8, A_9, A_{10}$ $A_{11}$, p and q are as defined in formula (I).

In another embodiment, compounds of the present invention have formula (I) wherein $L_1$ is alkylene; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, or —CH=$NOR_{EE}$; $L_2$ is —$(CH_2)_pO(CH_2)_q$—;

$R_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, or —CH=$NOR_{EE}$; and $R_A$, $R_B$, $R_C$, $R_E$, $R_F$, $R_{EE}$, $A_1$, $A_2$, $A_3$, $A_4$, $A_5$, $A_6$, $A_7$, $A_8$, $A_9$, $A_{10}$ $A_{11}$, p and q are as defined in formula (I).

In another embodiment, compounds of the present invention have formula (I) wherein $A_1$, $A_2$ and $A_3$ are each carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; $L_2$ is —$(CH_2)_pO(CH_2)_q$—; p is 0; q is 0; and $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; and $R_E$, $R_F$, and $R_{EE}$ are as defined in formula (I).

In another embodiment, compounds of the present invention have formula (I) wherein $A_1$ and $A_2$ are each independently selected from alkoxycarbonyl, carboxy, hydroxy, ($NR_AR_B$)carbonyl, or —S(O)$_2$OH; $A_3$ is carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; $L_2$ is —$(CH_2)_pO(CH_2)_q$—; p is 0; q is 0; and $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; and $R_E$, $R_F$, and $R_{EE}$ are as defined in formula (I).

In another embodiment, compounds of the present invention have formula (I) wherein $A_1$ and $A_2$ are each independently selected from carboxy or ($NR_CS(O)_2R_D$)carbonyl wherein one of $A_1$ or $A_2$ is ($NR_CS(O)_2R_D$)carbonyl; $A_3$ is carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, or —CH=$NOR_{EE}$; $L_2$ is —$(CH_2)_pO(CH_2)_q$—; p is 0; q is 0; $R_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, or —CH=$NOR_{EE}$; and $R_A$, $R_B$, $R_C$, $R_D$, $R_E$, $R_F$, and $R_{EE}$ are as defined in formula (I).

In another embodiment, compounds of the present invention have formula (I) wherein $A_1$ and $A_2$ are each independently selected from carboxy or ($NR_CS(O)_2R_D$)carbonyl wherein one of $A_1$ or $A_2$ is ($NR_CS(O)_2R_D$)carbonyl; $A_3$ is carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; $L_2$ is —$(CH_2)_pO(CH_2)_q$—; p is 0; q is 0; $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, or —$NR_ER_F$; $R_D$ is selected from alkyl or aryl; and $R_A$, $R_B$, $R_C$, $R_E$, $R_F$, and $R_{EE}$ are as defined in formula (I).

In another embodiment, compounds of the present invention have formula (I) wherein $A_1$ and $A_2$ are each independently selected from carboxy or ($NR_CS(O)_2R_D$)carbonyl wherein one of $A_1$ or $A_2$ is ($NR_CS(O)_2R_D$)carbonyl; $A_3$ is carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$; $L_2$ is —$(CH_2)_pO(CH_2)_q$—; p is 0; q is 0; $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH—$NOR_{EE}$, and —$NR_ER_F$; $R_D$ is selected from alkyl or aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, —$NR_ER_F$, and —$N(R_A)C(O)NR_BR_C$; and $R_A$, $R_B$, $R_C$, $R_E$, $R_F$, and $R_{EE}$ are as defined in formula (I).

In another embodiment, compounds of the present invention have formula (I) wherein $A_1$ and $A_2$ are each independently selected from carboxy or ($NR_CS(O)_2R_D$)carbonyl wherein one of $A_1$ or $A_2$ is ($NR_CS(O)_2R_D$)carbonyl; $A_3$ is carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; L$_2$ is —(CH$_2$)$_p$O(CH$_2$)$_q$—; p is 0; q is 0; R$_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; R$_D$ is heterocycle; and R$_A$, R$_B$, R$_C$, R$_E$, R$_F$, and R$_{EE}$ are as defined in formula (I).

XX In another embodiment, compounds of the present invention have formula (I) wherein A$_1$ and A$_2$ are each independently selected from carboxy or (NR$_C$S(O)$_2$R$_D$) carbonyl wherein one of A$_1$ or A$_2$ is (R$_C$S(O)$_2$R$_D$)carbonyl; A$_3$ is carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; L$_2$ is —(CH$_2$)$_p$O(CH$_2$)$_q$—; p is 0; q is 0; R$_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; R$_D$ is heterocycle wherein said heterocycle is pyridinyl and thienyl wherein said heterocycle is substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, nitro, —N(R$_A$)C(O)NR$_B$R$_C$, or —NR$_E$R$_F$; and R$_A$, R$_B$, R$_C$, R$_E$, R$_F$, and R$_{EE}$ are as defined in formula (I).

In another embodiment, compounds of the present invention have formula (I) wherein A$_1$ and A$_2$ are each independently selected from carboxy or (NR$_C$S(O)$_2$R$_D$)carbonyl wherein one of A$_1$ or A$_2$ is (NR$_C$S(O)$_2$R$_D$)carbonyl; A$_3$ is carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; L$_2$ is —(CH$_2$)$_p$O(CH$_2$)$_q$—; p is 0; q is 0; R$_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; R$_D$ is arylalkyl; and R$_A$, R$_B$, R$_C$, R$_E$, R$_F$, and R$_{EE}$ are as defined in formula (I).

In another embodiment, compounds of the present invention have formula (I) wherein A$_1$ and A$_2$ are each independently selected from carboxy or (NR$_C$S(O)$_2$R$_D$)carbonyl wherein one of A$_1$ or A$_2$ is (NR$_C$S(O)$_2$R$_D$)carbonyl; A$_3$ is carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; L$_2$ is —(CH$_2$)$_p$O(CH$_2$)$_q$—; p is 0; q is 0; R$_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; R$_D$ is arylalkyl wherein the aryl of arylalkyl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; and R$_C$, R$_E$, R$_F$, and R$_{EE}$ are as defined in formula (I).

In another embodiment, compounds of the present invention have formula (I) wherein A$_1$, A$_2$ and A$_3$ are each carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; L$_2$ is —(CH$_2$)$_p$O(CH$_2$)$_q$—; p is 0; q is 1; and R$_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; and R$_E$, R$_F$, and R$_{EE}$ are as defined in formula (I).

In another embodiment, compounds of the present invention have formula (I) wherein L$_1$ is alkylene; R$_1$ is aryl; L$_2$ is —(CH$_2$)$_p$O(CH$_2$)$_q$—; R$_2$ is cycloalkyl; and A$_1$, A$_2$, A$_3$, A$_4$, A$_5$, A$_6$, A$_7$, A$_8$, A$_9$, A$_{10}$ A$_{11}$, p and q are as defined in formula (I).

In another embodiment, compounds of the present invention have formula (I) wherein L$_1$ is alkylene; R$_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; L$_2$ is —(CH$_2$)$_p$O(CH$_2$)$_q$—; R$_2$ is cycloalkyl; and A$_1$, A$_2$, A$_3$, A$_4$, A$_5$, A$_6$, A$_7$, A$_8$, A$_9$, A$_{10}$, A$_{11}$, p and q are as defined in formula (I); and R$_A$, R$_B$, R$_C$, R$_E$, R$_F$, and R$_{EE}$ are as defined in formula (I).

In another embodiment, compounds of the present invention have formula (I) wherein A$_1$, A$_2$ and A$_3$ are each carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; L$_2$ is —(CH$_2$)$_p$O(CH$_2$)$_q$—; p is 0; q is 0; and R$_2$ is cycloalkyl; and R$_E$, R$_F$, and R$_{EE}$ are as defined in formula (I).

In another embodiment, compounds of the present invention have formula (I) wherein L$_1$ is alkylene; R$_1$ is aryl; L$_2$ is —(CH$_2$)$_p$O(CH$_2$)$_q$—; R$_2$ is cycloalkenyl; and A$_1$, A$_2$, A$_3$, A$_4$, A$_5$, A$_6$, A$_7$, A$_8$, A$_9$, A$_{10}$ A$_{11}$, p and q are as defined in formula (I).

In another embodiment, compounds of the present invention have formula (I) wherein L$_1$ is alkylene; R$_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; L$_2$ is —(CH$_2$)$_p$O(CH$_2$)$_q$—; R$_2$ is cycloalkenyl; and A$_1$, A$_2$, A$_3$, A$_4$, A$_5$, A$_6$, A$_7$, A$_8$, A$_9$, A$_{10}$ A$_{11}$, p and q are defined in formula (I); and R$_A$, R$_B$, R$_C$, R$_E$, R$_F$, and R$_{EE}$ are as defined in formula (I).

In another embodiment, compounds of the present invention have formula (I) wherein A$_1$, A$_2$ and A$_3$ are each carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; L$_2$ is —(CH$_2$)$_p$O(CH$_2$)$_q$—; p is 0; q is 0; and R$_2$ is cycloalkenyl; and R$_E$, R$_F$, and R$_{EE}$ are as defined in formula (I).

In another embodiment, compounds of the present invention have formula (I) wherein L$_1$ is alkylene; R$_1$ is aryl; L$_2$ is —(CH$_2$)$_p$O(CH$_2$)$_q$—; R$_2$ is heterocycle; and A$_1$, A$_2$, A$_3$, A$_4$, A$_5$, A$_6$, A$_7$, A$_8$, A$_9$, A$_{10}$ A$_{11}$, p and q are as defined in formula (I).

In another embodiment, compounds of the present invention have formula (I) wherein L$_1$ is alkylene; R$_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; L$_2$ is —(CH$_2$)$_p$O(CH$_2$)$_q$—; R$_2$ is heterocycle wherein heterocycle is selected from furyl, pyrazinyl, pyridazinyl, pyridinyl, pyrimidinyl, and thienyl wherein said heterocycle is substituted with 0, 1, 2, or 3 substituents independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, arylalkoxycarbonyl, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; and R$_A$, R$_B$, R$_C$, R$_E$, R$_F$, R$_{EE}$, A$_1$, A$_2$, A$_3$, A$_4$, A$_5$, A$_6$, A$_7$, A$_8$, A$_9$, A$_{10}$ A$_{11}$, p, and q are as defined in formula (I).

In another embodiment, compounds of the present invention have formula (I) wherein A$_1$, A$_2$ and A$_3$ are each carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; L$_2$ is —(CH$_2$)$_p$O(CH$_2$)$_q$—; p is 0; q is 0; and R$_2$ is heterocycle wherein heterocycle is selected from pyridinyl or pyrimidinyl wherein the heterocycle is substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, nitro, —N(R$_A$)C(O)NR$_B$R$_C$, or —NR$_E$R$_F$; and R$_A$, R$_B$, R$_C$, R$_E$, R$_F$, and R$_{EE}$ are as defined in formula (I).

In another embodiment, compounds of the present invention have formula (I) wherein L$_1$ is alkylene; R$_1$ is aryl; L$_2$ is —(CH$_2$)$_p$S(CH$_2$)$_q$—; R$_2$ is aryl; and A$_1$, A$_2$, A$_3$, A$_4$, A$_5$, A$_6$, A$_7$, A$_8$, A$_9$, A$_{10}$ A$_{11}$, p and q are as defined in formula (I).

In another embodiment, compounds of the present invention have formula (I) wherein L$_1$ is alkylene; R$_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; L$_2$ is —(CH$_2$)$_p$S(CH$_2$)$_q$—; R$_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; and R$_A$, R$_B$, R$_C$, R$_E$, R$_F$, R$_{EE}$, A$_1$, A$_2$, A$_3$, A$_9$ A$_5$, A$_6$, A$_7$, A$_8$, A$_9$, A$_{10}$ A$_{11}$, p and q are as defined in formula (I).

In another embodiment, compounds of the present invention have formula (I) wherein A$_1$, A$_2$ and A$_3$ are each carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; L$_2$ is —(CH$_2$)$_p$S(CH$_2$)$_q$—; p is 0; q is 0; and R$_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; and R$_E$, R$_F$, and R$_{EE}$ are as defined in formula (I).

In another embodiment, compounds of the present invention have formula (I) wherein L$_1$ is aryl; L$_2$ is —$(CH_2)_pC(O)(CH_2)_q$—; $R_2$ is aryl; and $A_1$, $A_2$, $A_3$, $A_4$, $A_5$, $A_6$, $A_7$, $A_8$, $A_9$, $A_{10}$ $A_{11}$, p and q are as defined in formula (I).

In another embodiment, compounds of the present invention have formula (I) wherein $L_1$ is alkylene; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, $(NR_ER_F)$carbonyl, —$N(R_A)C(O)NR_BR_C$, or —$CH=NOR_{EE}$; $L_2$ is —$(CH_2)_pC(O)(CH_2)_q$—; $R_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, $(NR_ER_F)$carbonyl, —$N(R_A)C(O)NR_BR_C$, or —$CH=NOR_{EE}$; and $R_A$, $R_B$, $R_C$, $R_E$, $R_F$, $R_{EE}$, $A_1$, $A_2$, $A_3$, $A_4$, $A_5$, $A_6$, $A_7$, $A_8$, $A_9$, $A_{10}$ $A_{11}$, p and q are as defined in formula (I).

In another embodiment, compounds of the present invention have formula (I) wherein $A_1$, $A_2$ and $A_3$ are each carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, or —$NR_ER_F$; $L_2$ is —$(CH_2)_pC(O)(CH_2)_q$—; p is 0; q is 0; and $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, or —$NR_ER_F$; and $R_E$, $R_F$, and $R_{EE}$ are as defined in formula (I).

In another embodiment, compounds of the present invention have formula (I) wherein $L_1$ is alkylene; $R_1$ is aryl; $L_2$ is —$(CH_2)_pC(OH)(CH_2)_q$—; $R_2$ is aryl; and $A_1$, $A_2$, $A_3$, $A_4$, $A_5$, $A_6$, $A_7$, $A_8$, $A_9$, $A_{10}$ $A_{11}$, p and q are as defined in formula (I).

In another embodiment, compounds of the present invention have formula (I) wherein $L_1$ is alkylene; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, $(NR_ER_F)$carbonyl, —$N(R_A)C(O)NR_BR_C$, or —$CH=NOR_{EE}$; $L_2$ is —$(CH_2)_pC(OH)(CH_2)_q$—; $R_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, $(NR_ER_F)$carbonyl, —$N(R_A)C(O)NR_BR_C$, or —$CH=NOR_{EE}$; and $R_A$, $R_B$, $R_C$, $R_E$, $R_F$, $R_{EE}$, $A_1$, $A_2$, $A_3$, $A_5$, $A_6$, $A_7$, $A_8$, $A_9$, $A_{10}$ $A_{11}$, p, and q are as defined in formula (I).

In another embodiment, compounds of the present invention have formula (I) wherein $A_1$, $A_2$ and $A_3$ are each carboxy; $A_4$, $A_5$, $A_6$, $A_7$, As, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, or —$NR_ER_F$; $L_2$ is —$(CH_2)_pC(OH)(CH_2)_pC(OH)(CH_2)_q$—; p is 0; q is 0; and $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH—NOR_{EE}$, or —$NR_ER_F$; and $R_E$, $R_F$, and $R_{EE}$ are as defined in formula (I).

In another embodiment, compounds of the present invention have formula (I) wherein $L_1$ is alkylene; $R_1$ is aryl; $L_2$ is —$(CH_2)_pCH=NO(CH_2)_q$—; $R_2$ is aryl; and $A_1$, $A_2$, $A_3$, $A_4$, $A_5$, $A_7$, $A_8$, $A_9$, $A_{10}$ $A_{11}$, p and q are as defined in formula (I).

In another embodiment, compounds of the present invention have formula (I) wherein $L_1$ is alkylene; $R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, $(NR_ER_F)$carbonyl, —$N(R_A)C(O)NR_BR_C$, or —$CH=NOR_{EE}$; $L_2$ is —$(CH_2)_pCH=NO(CH_2)_q$—; $R_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, $(NR_ER_F)$carbonyl, —$N(R_A)C(O)NR_BR_C$, or —$CH=NOR_{EE}$; and $R_A$, $R_B$, $R_C$, $R_E$, $R_F$, $R_{EE}$, $A_1$, $A_2$, $A_3$, $A_4$, $A_5$, $A_6$, $A_7$, $A_8$, $A_9$, $A_{10}$ $A_{11}$, p, and q are as defined in formula (I).

In another embodiment, compounds of the present invention have formula (I) wherein $A_1$, $A_2$ and $A_3$ are each carboxy; $A_4$, $A_5$, $A_6$, $A_7$, $A_8$, $A_9$, $A_{10}$ and $A_{11}$ are each hydrogen; $L_1$ is alkylene wherein said alkylene is —$CH_2$—; $R_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, or —$NR_ER_F$; $L_2$ is —$(CH_2)_pCH=NO(CH_2)_q$—; p is 0; q is an integer 0–1; and $R_2$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; and R$_E$, R$_F$, and R$_{EE}$ are as defined in formula (I).

In another embodiment, compounds of the present invention have formula (I) wherein L$_1$ is alkylene; R$_1$ is aryl; L$_2$ is —(CH$_2$)$_p$CH=NO(CH$_2$)$_q$—; R$_2$ is heterocycle; and A$_1$, A$_2$, A$_3$, A$_4$, A$_5$, A$_6$, A$_7$, A$_8$, A$_9$, A$_{10}$ A$_{11}$, p and q are as defined in formula (I).

In another embodiment, compounds of the present invention have formula (I) wherein A$_1$, A$_2$ and A$_3$ are each carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is aryl wherein said aryl is phenyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; L$_2$ is —(CH$_2$)$_p$CH=NO(CH$_2$)$_q$—; p is 0; q is 0; and R$_2$ is heterocycle wherein said heterocycle is pyranyl substituted with 0,1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, nitro, —N(R$_A$)C(O)NR$_B$R$_C$, or —NR$_E$R$_F$; and R$_A$, R$_B$, R$_C$, R$_E$, R$_F$, and R$_{EE}$ are as defined in formula (I).

In another embodiment, compounds of the present invention have formula (I) wherein L$_1$ is alkylene; R$_1$ is cycloalkyl; L$_2$ is absent; R$_2$ is absent; and A$_1$, A$_2$, A$_3$, A$_4$, A$_5$, A$_6$, A$_7$, A$_8$, A$_9$, A$_{10}$ A$_{11}$, p and q are as defined in formula (I).

In another embodiment, compounds of the present invention have formula (I) wherein A$_1$, A$_2$ and A$_3$ are each carboxy; A$_4$, A$_5$, A$_6$, A$_7$, A$_8$, A$_9$, A$_{10}$ and A$_{11}$ are each hydrogen; L$_1$ is —CH$_2$—; R$_1$ is cycloalkyl; L$_2$ is absent; and R$_2$ is absent.

In another embodiment, compounds of the present invention have formula (I) wherein L$_1$ is —(CH$_2$)$_m$O(CH$_2$)$_n$—; R$_1$ is aryl; L$_2$ is absent; R$_2$ is absent; and A$_1$, A$_2$, A$_3$, A$_4$, A$_5$, A$_6$, A$_7$, A$_8$, A$_9$, A$_{10}$ A$_{11}$, and n are as defined in formula (I).

In another embodiment, compounds of the present invention have formula (I) wherein L$_1$ is —(CH$_2$)$_n$O(CH$_2$)$_n$—; R$_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; L$_2$ is absent; R$_2$ is absent; and R$_A$, R$_B$, R$_C$, R$_E$, R$_F$, R$_{EE}$, A$_1$, A$_2$, A$_3$, A$_4$, A$_5$, A$_6$, A$_7$, A$_8$, A$_9$, A$_{10}$ A$_{11}$, m, and n are as defined in formula (I).

In another embodiment, compounds of the present invention have formula (I) wherein A$_1$, A$_2$ and A$_3$ are each carboxy; A$_4$, A$_5$, A$_6$, A$_7$, A$_8$, A$_9$, A$_{10}$ and A$_{11}$ are each hydrogen; L$_1$ is —(CH$_2$)$_m$O(CH$_2$)$_n$—; m is an integer 2–4; n is 0; R$_1$ is aryl wherein said aryl is phenyl with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, or —NR$_E$R$_F$; L$_2$ is absent; R$_2$ is absent; and R$_E$, R$_F$, and R$_{EE}$ are as defined in formula (I).

In another embodiment, compounds of the present invention have formula (I) wherein L$_1$ is alkylene; R$_1$ is heterocycle; L$_2$ is absent; R$_2$ is absent; and A$_1$, A$_2$, A$_3$, A$_4$, A$_5$, A$_6$, A$_7$, A$_8$, A$_9$, A$_{10}$ and A$_{11}$ are as defined in formula (I).

In another embodiment, compounds of the present invention have formula (I) wherein L$_1$ is alkylene; R$_1$ is heterocycle wherein said heterocycle is selected from furyl, pyrazinyl, pyridazinyl, pyridinyl, pyrimidinyl and thienyl wherein said heterocycle is substituted with 0, 1, 2, or 3 substituents independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, arylalkoxycarbonyl, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, or —CH=NOR$_{EE}$; L$_2$ is absent; R$_2$ is absent; and A$_1$, A$_2$, A$_3$, A$_4$, A$_5$, A$_6$, A$_7$, A$_8$, A$_9$, A$_{10}$ and A$_{11}$ are as defined in formula (I); and R$_A$, R$_B$, R$_C$, R$_E$, R$_F$, and R$_{EE}$ are as defined in formula (I).

In another embodiment, compounds of the present invention have formula (I) wherein A$_1$, A$_2$ and A$_3$ are each carboxy; A$_4$, A$_5$, A$_6$, A$_7$, A$_8$, A$_9$, A$_{10}$ and A$_{11}$ are each hydrogen; L$_1$ is alkylene wherein said alkylene is —CH$_2$—; R$_1$ is heterocycle wherein said heterocycle is thienyl substituted with 0, 1, or 2 substituents selected from alkoxy, alkoxycarbonyl, alkenyl, alkenyloxy, alkyl, alkylthio, cyano, formyl, haloalkoxy, haloalkyl, haloalkylthio, halogen, hydroxyalkyl, nitro, —N(R$_A$)C(O)NR$_B$R$_C$, or —NR$_E$R$_F$; L$_2$ is absent; R$_2$ is absent; and R$_E$, R$_F$, and R$_{EE}$ are as defined in formula (I).

Another embodiment of the present invention relates to pharmaceutical compositions comprising a therapeutically effective amount of a compound of formula (I) or a pharmaceutically acceptable salt thereof in combination with a pharmaceutically acceptable carrier.

Another embodiment of the present invention relates to a method for controlling pain in a mammal in need of such treatment comprising administering a therapeutically effective amount of a compound of formula (I) or a pharmaceutically acceptable salt thereof in combination with a pharmaceutically acceptable carrier.

Another embodiment of the present invention relates to a method of treating urinary incontinence in a host mammal in need of such treatment comprising administering a therapeutically effective amount of a compound of formula (I) or a pharmaceutically acceptable salt thereof in combination with a pharmaceutically acceptable carrier.

Another embodiment of the present invention relates to a method of treating bladder overactivity in a host mammal in need of such treatment comprising administering a therapeutically effective amount of a compound of formula (I) or a pharmaceutically acceptable salt thereof in combination with a pharmaceutically acceptable carrier.

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of from 2 to 10 carbon atoms containing at least one double bond. Representative examples of alkenylene include, but are not limited to, —CH═CH—, —CH═CH$_2$CH$_2$—, and —CH═C(CH$_3$)CH$_2$—.

The term "alkenyloxy" as used herein, means an alkenyl group, as defined herein, is appended to the parent molecular moiety through an oxygen atom. Representative examples of alkenyloxy include, but are not limited to, allyloxy, 2-butenyloxy and 3-butenyloxy.

The term "alkoxy" as used herein, means an alkyl group, as defined herein, is appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, is appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, is appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, is appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, is appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, is appended appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, is appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, is appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, is appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" denotes a divalent group derived from a straight or branched chain hydrocarbon of from 1 to 10 carbon atoms. Representative examples of alkylene include, but are not limited to, —CH$_2$—, —CH$_2$CH$_2$—, —CH$_2$CH(CH$_3$)— —CH$_2$CH$_2$CH$_2$—, —CH$_2$CH$_2$CH$_2$CH$_2$—, and —CH$_2$CH(CH$_3$)CH$_2$—.

The term "alkylsulfonyl" as used herein, means an alkyl group, as defined herein, is appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, is appended to the parent molecular moiety through a sulfur atom. Representative examples of alkylthio include, but are not limited, methylsulfanyl, ethylsulfanyl, tert-butylsulfanyl, and hexylsulfanyl.

The term "alkylthioalkyl" as used herein, means an alkylthio group, as defined herein, is appended to the parent molecular moiety through an alkyl group, as defined herein. Representative examples of alkylthioalkyl include, but are not limited, methylsulfanylmethyl and 2-(ethylsulfanyl) ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynylene" denotes a divalent group derived from a straight or branched chain hydrocarbon of from 2 to 10 carbon atoms containing at least one triple bond. Representative examples of alkynylene include, but are not limited to, —C≡C—, —CH$_2$C≡C—, —CH(CH$_3$)CH$_2$C≡C—, —C≡CCH$_2$—, and —C≡CCH(CH$_3$)CH$_2$—.

The term "alkynyloxy," as used herein, means an alkynyl group, as defined herein, is appended to the parent molecular moiety through an oxygen atom. Representative examples of alkynyloxy include, but are not limited to, 2-propynyloxy and 2-butynyloxy.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indanyl, indenyl, naphthyl, phenyl, and tetrahydronaphthyl.

The aryl groups of this invention are substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, and —CH═NOR$_{EE}$ wherein R$_{EE}$ is selected from hydrogen and alkyl, as defined herein.

The term "arylalkoxy" as used herein, means an aryl group, as defined herein, is appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" as used herein, means an arylalkoxy group, as defined herein, is appended to the parent molecular moiety through a carbonyl group, as defined herein. Representative examples of arylalkoxycarbonyl include, but are not limited to, benzyloxycarbonyl and naphth-2-ylmethoxycarbonyl.

The term "carbonyl" as used herein, means a —C(O)— group.

The term "carboxy" as used herein, means a —CO$_2$H group.

The term "carboxyalkyl" as used herein, means a carboxy group, as defined herein, is appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, is appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2] nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of this invention are substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl and —CH=NOR$_{EE}$ wherein R$_{EE}$ is selected from hydrogen and alkyl, as defined herein.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The cycloalkenyl groups of this invention are substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl and —CH=NOR$_{EE}$ wherein R$_{EE}$ is selected from hydrogen and alkyl, as defined herein.

The term "ethylenedioxy" as used herein, refers to a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "haloalkoxy" as used herein, means at least one halogen, as defined herein, is appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, is appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylthio" as used herein, means a haloalkyl group, as defined herein, is appended to the parent molecular moiety through a sulfur atom. Representative examples of haloalkylthio include, but are not limited to, (trifluoromethyl)sulfanyl and (pentafluoroethyl)sulfanyl.

The term "heterocycle" or "heterocyclic" as used herein, means a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo[b,d]furanyl, dibenzo[b,d]thienyl, naphtho[2,3-b]furan, naphtho[2,3-b]thienyl, phenazinyl, phenothiazinyl, phenoxazinyl, thianthrenyl, thioxanthenyl and xanthenyl.

The heterocycles of this invention are substituted with 0, 1, 2, or 3 substituents independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, arylalkoxycarbonyl, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —CH=$NOR_{EE}$ wherein $R_{EE}$ is selected from hydrogen and alkyl, as defined herein.

The term "hydroxy," as used herein, means an —OH group.

The term "hydroxyalkyl," as used herein, means at least one hydroxy group, as defined herein, is appended to the parent molecular moiety through an alkyl group, as defined herein. Representative examples of hydroxyalkyl include, but are not limited to, 1,3-dihydroxypropyl, 1,2-dihydroxypropyl, hydroxymethyl, 2-hydroxyethyl, 3-hydroxypropyl, and 2-ethyl-4-hydroxyheptyl.

The term "mercapto" as used herein, means a —SH group.

The term "methylenedioxy" as used herein, means a —OC($Z_3$)($Z_4$)O— group wherein the oxygen atoms of the methylenedioxy are attached to the parent molecular moiety through two adjacent carbon atoms. $Z_3$ and $Z_4$ are each independently selected from hydrogen or alkyl or $Z_3$ and $Z_4$ together with the carbon atom to which they are attached form a 5 or 6 membered cycloalkyl group, as defined herein.

The term "nitro" as used herein, refers to a —$NO_2$ group.

The term "—$NR_AR_B$" as used herein, means two groups, $R_A$ and $R_B$, are appended to the parent molecular moiety through a nitrogen atom. $R_A$ and $R_B$ are each independently selected from hydrogen, alkyl and cyano. Representative examples of —$NR_AR_B$ include, but are not limited to, amino, methylamino, dimethylamino and cyanoamino.

The term "($NR_AR_B$)carbonyl" as used herein, means a —$NR_AR_B$ group, as defined herein, is appended to the parent molecular moiety through a carbonyl group, as defined herein. Representative examples of ($NR_AR_B$)carbonyl include, but are not limited to, aminocarbonyl, (methylamino)carbonyl, (dimethylamino)carbonyl, (cyanoamino)carbonyl and (ethylmethylamino)carbonyl.

The term "—$NR_ER_F$" as used herein, means two groups, $R_E$ and $R_F$, are appended to the parent molecular moiety through a nitrogen atom. $R_E$ and $R_F$ are each independently selected from hydrogen, alkyl, alkylcarbonyl, formyl, and hydroxyalkyl. Representative examples of —$NR_ER_F$ include, but are not limited to, amino, acetylamino, methylamino, dimethylamino, ethylmethylamino, (2,3-dihydoxypropyl)amino, and formylamino.

The term "($NR_ER_F$)carbonyl" as used herein, means a —$NR_ER_F$ group, as defined herein, is appended to the parent molecular moiety through a carbonyl group, as defined herein. Representative examples of ($NR_ER_F$)carbonyl include, but are not limited to, aminocarbonyl, (methylamino)carbonyl, (dimethylamino)carbonyl and (ethylmethylamino)carbonyl.

The term "—$NR_CS(O)_2R_D$" is used herein means $R_D$ appended to the parent molecular moiety through a sulfonyl group, the sulfonyl group with is further appended to the parent molecular moiety through an amino group as defined herein. Examples of —$NR_CS(O)_2R_D$ include, but not limited to, arylsulfonylamino wherein aryl is substituted or unsubstituted phenyl.

The term "($NR_CS(O)_2R_D$)carbonyl" is used herein means a —$NR_CS(O)_2R_D$ group appended to the parent molecular moiety through a carbonyl group.

The term "oxo" as used herein, means a =O moiety.

The term "sulfonyl" as used herein, means a —$SO_2$— group.

In vitro Data Determination of Inhibition Potencies

Compounds of the present invention were determined to be $P2X_3$ and $P2X_{2/3}$ antagonists based on their ability to inhibit increases in cytosolic $Ca^{2+}$ concentration elicited by the P2X receptor agonist αβ-methyleneATP (αβ-meATP; Sigma, St. Louis, Mo.) as described in Bianchi et al. (1999). The fluorescent $Ca^{2+}$ chelating dye fluo-4 was used as an indicator of the relative levels of intracellular $Ca^{2+}$ in a 96-well format using a Fluorescence Imaging Plate Reader (FLIPR, Molecular Devices, Sunnyvale, Calif.). Cells expressing recombinant human $P2X_3$ or $P2X_{2/3}$ containing receptors were grown to confluence and plated in 96-well black-walled tissue culture plates approximately 18 hours prior to the experiment. One to two hours before the assay, cells were loaded with fluo-4 AM (2.28 μM; Molecular Probes, Eugene, Oreg.) in D-PBS and maintained in a dark environment at room temperature. Immediately before the assay, each plate was washed twice with 250 μl D-PBS per well to remove extracellular fluo-4 AM and then 100 μl D-PBS was added to the wells. Two 50 μl additions of compounds (4× concentration prepared in D-PBS) were made to the cells during each experiment. The first addition consisting of test antagonist was made and incubation continued for 3 minutes before the addition of the agonist αβ-meATP, measurement continued for 3 minutes after this final addition. Fluorescence data was collected at 1 or 5 second intervals throughout the course of each experiment and were analyzed based on the peak increase in relative fluorescence units compared with basal fluorescence. Antagonist concentration-response data, expressed as a percentage of the maximal αβ-meATP response in the absence of test antagonist, were analyzed using GraphPad Prism (San Diego, Calif.).

The compounds of the present invention were found to be antagonists of the $P2X_3$ containing receptor with potencies from 5000 nM to 0.5 nM. In a preferred range, the compounds of the present invention antagonized $P2X_3$ containing receptors with potencies from 500 nM to 0.5 nM. In a more preferred range, the compounds of the present invention antagonized $P2X_3$ containing receptors with potencies from 50 nM to 0.5 nM.

Additionally, the compounds of the present invention were found to be antagonists of the $P2X_{2/3}$ containing receptors with potencies from 4800 nM to 0.5 nM. In a preferred range, the compounds of the present invention antagonized $P2X_{2/3}$ containing receptors with potencies from 500 nM to 0.5 nM. In a more preferred range, the compounds of the present invention antagonized $P2X_{2/3}$ containing receptors with potencies from 50 nM to 0.5 nM.

In vivo Data Determination of Antinociceptive Effect

Following a 30-minute acclimation period to individual clear observation cages, 50 μl of a 5% formalin solution was injected subcutaneously (s.c.) into the dorsal aspect of the right hindpaw of rats (male Sprague-Dawley, 200–300 g) were then returned to the observation cages, which were suspended above mirrors. Rats, six per group, were observed for either a continuous period of 60 minutes or for periods of time corresponding to phase 1 and phase 2 of the formalin test (Abbott et al., Pain, 60 (1995) 91–102). Phase 1 of the formalin test was defined as the period of time immediately following injection of formalin until 10 minutes after the formalin injection. Effects on Phase 2 of the formalin test were determined by monitoring for the 20 minute period of time from 30 to 50 minutes following formalin injection. Nociceptive behaviors were recorded from animals during the session by observing each animal for one 60 second observation period during each 5 minute interval. Nociceptive behaviors recorded included flinching, licking or biting the injected paw.

The compounds of the present invention were found to have antinociceptive effects with potencies from 100 μmol/kg to 15 μmol/kg.

The in vitro and in vivo data demonstrates that compounds of the present invention antagonize the $P2X_3$ containing receptor, antagonize the $P2X_{2/3}$ containing receptor, and are useful for treating pain. Compounds of the present invention are thus useful for ameliorating or preventing additional disorders that are affected by the $P2X_3$ and/or the $P2X_{2/3}$ containing receptors such as bladder overactivity and urinary incontinence.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.01 to about 100 mg/kg/day. For purposes of oral administration, more preferable doses can be in the range of from about 0.1 to about 25 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Compounds of the present invention that are formed by in vivo conversion of a different compound that was administered to a mammal are intended to be included within the scope of the present invention.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The compounds of the invention, including but not limited to those specified in the examples, are $P2X_3$ and $P2X_2/P2X_3$ containing receptor antagonists in mammals. As $P2X_3$ and $P2X_2/P2X_3$ containing receptor antagonists, the compounds of the present invention are useful for the treatment and prevention of disorders such as bladder overactivity, urinary incontinence or pain.

The ability of the compounds of the present invention, including but not limited to those specified in the examples, to treat bladder overactivity or urinary incontinence is demonstrated by Namasivayam et al., Brit. J. Urol. Int. 84L 854–860. (1999).

The ability of the compounds of the present invention, including but not limited to those specified in the examples, to treat pain is demonstrated by Cesare et al., Drug Dev. Res. 50: S01–02 (2000); Cockayne et al., Drug Dev. Res. 50: 005 (2000); Bleehen, Br. J. Pharmacol. 62:573–577 (1978); Cook et al., Nature 387:505–508 (1997); and Driessen and Starke, Naunyn Schmiedebergs Arch. Pharmacol. 350:618–625 (1994).

Abbreviations

Abbreviations which have been used in the descriptions of the Schemes and the Examples that follow are: DCC for 1,3-dicyclohexylcarbodiimide, DME for dimethoxyethane, DMF for N,N-dimethylformamide, DMSO for dimethylsulfoxide, EDCI or EDC for 1-ethyl-3-[3-(dimethylamino)propyl]-carbodiimide hydrochloride, LAH for lithium aluminum hydride, RP-HPLC for reverse phase-high pressure liquid chromatography and THF for tetrahydrofuran.

Preparation of Compounds of the Present Invention

The compounds and processes of the present invention will be better understood in connection with the following synthetic Schemes and Examples which illustrate a means by which the compounds of the present invention can be prepared.

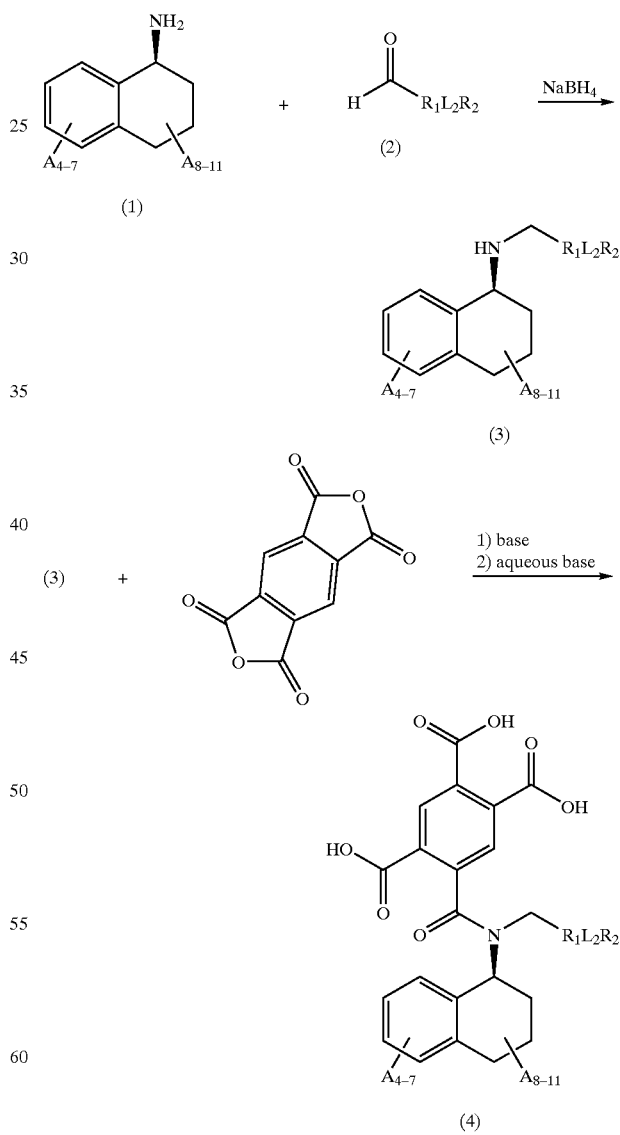

Benzenetricarboxylic acids of general formula (4), wherein $A_4$, $A_5$, $A_6$, $A_7$, $A_8$, $A_9$, $A_{10}$, $A_{11}$, $R_1$, $R_2$ and $L_2$ are as defined in formula (I), may be prepared as described in Scheme 1. (1S)-1,2,3,4-Tetrahydro-1-naphthalenylamines of general formula (1), purchased commercially or prepared using standard chemistry known to those in the art, may be treated with aldehydes of general formula (2) and a hydride source such as sodium borohydride in a solvent such as ethanol to provide secondary amines of general formula (3). Secondary amines of general formula (3) may be treated with 1,2,4,5-benzenetetracarboxylic dianhydride and an organic base such as triethylamine and after a period of 4–72 hours a base in water such as sodium carbonate/water may be added to the reaction mixture to provide benzenetricarboxylic acids of general formula (4).

coupling conditions may be used such as thionyl chloride or chloroformates to provide amides of general formula (7). Amides of general formula (7) may be treated with borane-tetrahyrofuran complex or lithium aluminum hydride to provide secondary amines of general formula (3). Secondary amines of general formula (3) may be processed as described in Scheme 1 to provide benzenetricarboxylic acids of general formula (4).

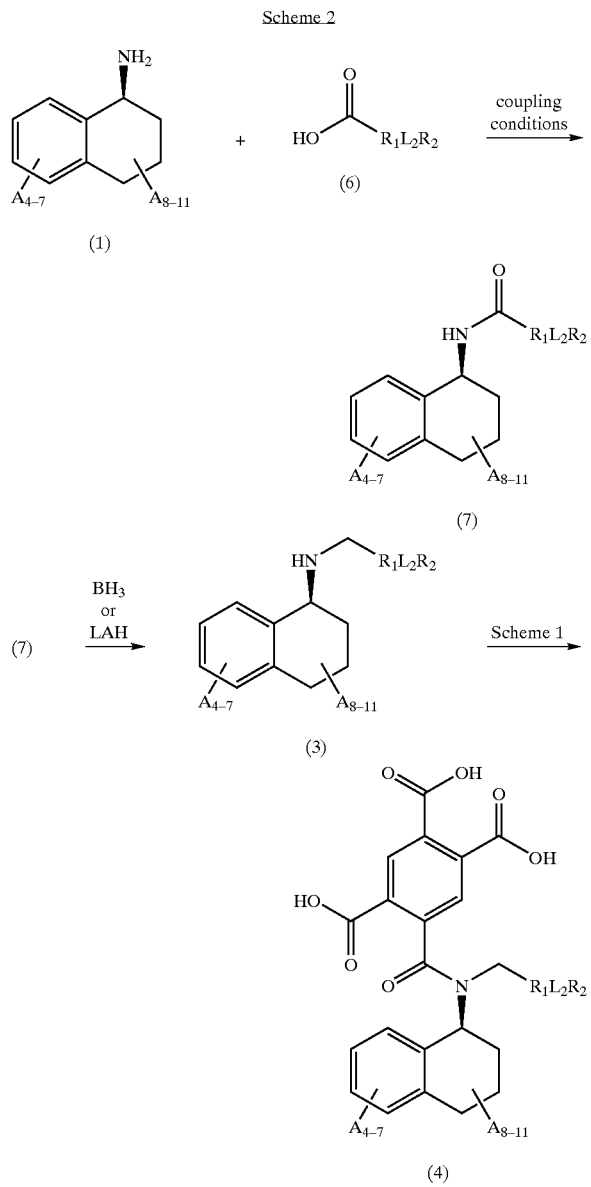

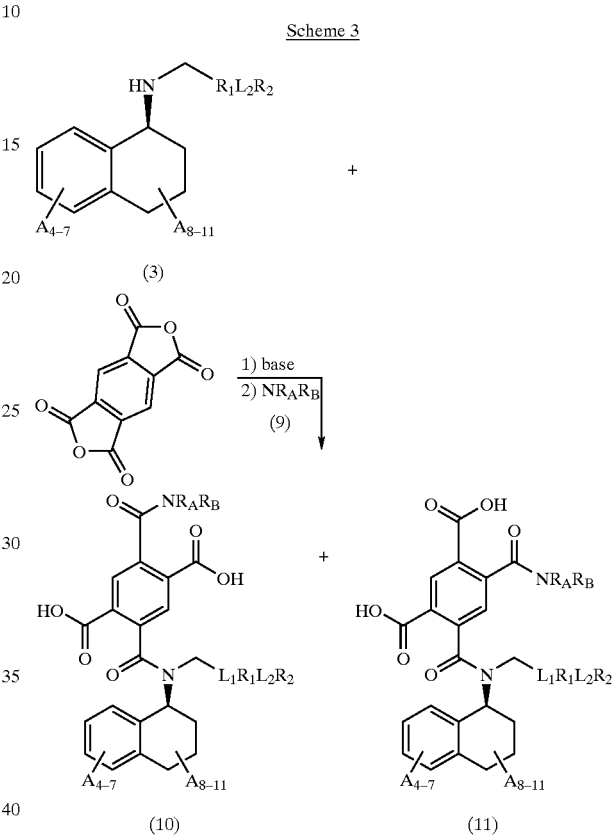

Amides of general formula (10) and (11), wherein $A_4$, $A_5$, $A_6$, $A_7$, $A_8$, $A_9$, $A_{10}$, $A_{11}$, $R_1$, $R_2$, $L_1$, $L_2$, $R_A$ and $R_B$ are as defined in formula (I), may be prepared as described in Scheme 2. Secondary amines of general formula (3) may be treated with 1,2,4,5-benzenetetracarboxylic dianhydride and an organic base such as triethylamine and after a period of 4–72 hours an amine of general formula (9) may be added to the reaction mixture to provide amides of general formula (10) and (11). Esters may also be prepared in similar fashion except that an alcohol is added after the 4–72 hour period instead of an amine.

An alternate method of preparing benzenetricarboxylic acids of general formula (4), wherein $A_4$, $A_5$, $A_6$, $A_7$, $A_8$, $A_9$, $A_{10}$, $A_{11}$, $R_1$, $R_2$ and $L_2$ are as defined in formula (I), may be used as described in Scheme 2. (1S)-1,2,3,4-Tetrahydro-1-naphthalenylamines of general formula (1) may be coupled with acids of general formula (6) using standard coupling conditions known to those in the art such. Carbodiimides such as DCC or EDCI may be used or other

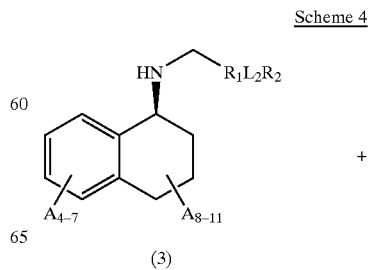

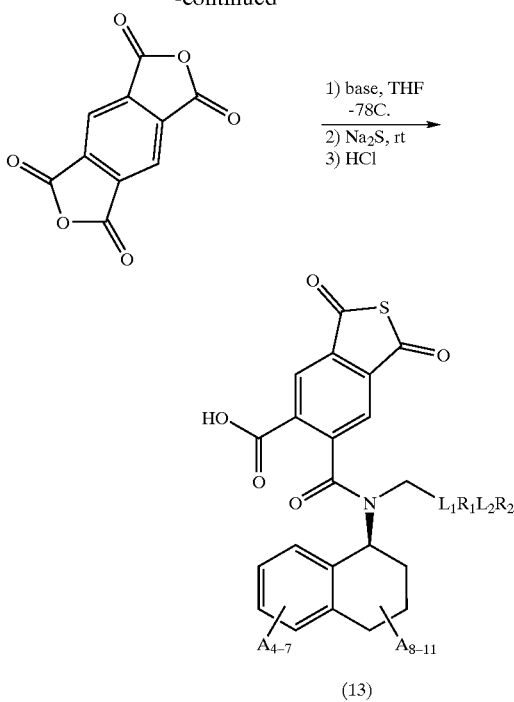

1,3-Dioxo-1,3-dihydro-2-benzothiophene-5-carboxylic acids of general formula (13), wherein $A_4$, $A_5$, $A_6$, $A_7$, $A_8$, $A_9$, $A_{10}$, $A_{11}$, $R_1$, $R_2$, $L_1$ and $L_2$ are defined in formula (I), may be prepared as described in Scheme 4. Secondary amines of general formula (3) may be treated with 1,2,4,5-benzenetetracarboxylic dianhydride and an organic base such as triethylamine at −78° C. and allowed to warm to ambient temperature and stir for 4–72 hours. The reaction mixture may then be recooled to −78° C. and treated with sodium sulfide nonahydrate followed by aqueous acid to provide 1,3-dioxo-1,3-dihydro-2-benzothiophene-5-carboxylic acids of general formula (13).

The following Examples are intended as an illustration of and not a limitation upon the scope of the invention as defined in the appended claims.

EXAMPLE 1

5-({[3-(4-chlorophenoxy)benzyl][(1S)-1,2,3,4-tetrahydro-1-naphthalenyl]amino}carbonyl)-1,2,4-benzenetricarboxylic acid

EXAMPLE 1A

N-[3-(4-chlorophenoxy)benzyl]-N-[(1S)-1,2,3,4-tetrahydro-1-naphthalenyl]amine 3-(4-Chlorophenoxy)benzaldehyde (1.50 mL, 7.82 mmol, purchased from Acros Organics) in 30 mL absolute ethanol was treated with (1S)-1,2,3,4-tetrahydro-1-naphthalenylamine (1.12 mL, 7.82 mmol, purchased from Lancaster). After stirring at ambient temperature for 4 hours, the mixture was treated with NaBH$_4$ (0.33 g, 8.60 mmol) in one portion. After stirring an additional 18 hours, the reaction mixture was concentrated under reduced pressure and the residue dissolved in diethyl ether and quenched by addition of a solution of 1N NaOH. The phases were allowed to separate and the aqueous phase was extracted with diethyl ether. The organic phases were combined, washed with water, brine, dried (Na$_2$SO$_4$), filtered and the filtrate concentrated under reduced pressure. The residue was purified by flash chromatography (silica gel, 15% ethyl acetate/hexanes) to provide the title compound as a colorless oil (2.26 g, 79%). $^1$H NMR (300 MHz, CDCl$_3$) δ6.85–7.37 (m, 12H), 3.75–3.95 (m, 3H), 2.65–2.9 (m, 2H), 1.4–2.1 (m, 5H); MS (ESI+) 364 (M+H)$^+$.

EXAMPLE 1B 5-({[3-(4-chlorophenoxy)benzyl][(1S)-1,2,3,4-tetrahydro-1-naphthalenyl]amino}carbonyl)-1,2,4-benzenetricarboxylic acid 1,2,4,5-Benzenetetracarboxylic dianhydride (2.70 g, 12.4 mmol) and triethylamine (2.15 mL, 15.5 mmol) in THF (60 mL)were treated dropwise with the product from Example 1A (2.25 g, 6.18 mmol) in THF (10 mL) at −78° C. The reaction mixture was allowed to stir for 16 hours gradually warming to ambient temperature. The mixture was treated with saturated aqueous Na$_2$CO$_3$ solution, stirred vigorously for 30 minutes and then carefully acidified using 12M HCl. The acidified solution was extracted with ethyl acetate. The organic extracts were combined, washed with 1N HCl, brine, dried (Na$_2$SO$_4$), filtered and concentrated under reduced pressure. The residue was purified by flash chromatography (silica gel, 100:1:1 ethyl acetate:HCO$_2$H:H$_2$O) to provide the title compound as a white solid (1.92 g, 52% yield).
$^1$H NMR (300 MHz, DMSO-d$_6$) δ13.9 (bs, 1H), 6.6–8.3 (m, 14H), 3.9–5.65 (m, 3H), 2.5–2.7 (m, 2H), 1.3–2.2 (m, 4H); MS (ESI+) 600 (M+H)$^+$.

EXAMPLE 2

5-({([1,1'-biphenyl]-4-ylmethyl)[(1S)-1,2,3,4-tetrahydro-1-naphthalenyl]amino}carbonyl)-1,2,4-benzenetricarboxylic acid

EXAMPLE 2A

N-([1,1'-biphenyl]-4-ylmethyl)-N-[(1S)-1,2,3,4-tetrahydro-1-naphthalenyl]amine

[1,1'-Biphenyl]-4-carbaldehyde and (1S)-1,2,3,4-tetrahydro-1-naphthalenylamine were processed as described in Example 1A to provide the title compound.
$^1$H NMR (CDCl$_3$) δ7.61–7.05 (m, 13H), 4.02–3.81 (m, 3H), 2.78 (m, 2H), 2.10–1.90 (m, 3H), 1.76 (m, 1H), 1.50 (broad s, 1H); MS (ESI+) 314 (M+H)$^+$.

EXAMPLE 2B 5-({([1,1'-biphenyl]-4-ylmethyl)[(1S)-1,2,3,4-tetrahydro-1-naphthalenyl]amino}carbonyl)-1,2,4-benzenetricarboxylic acid The product from Example 2A and 1,2,4,5-benzenetetracarboxylic dianhydride were processed as described in Example 1B to provide the title compound.
$^1$H NMR (DMSO-d$_6$) δ8.40–7.05 (m, 15H), 5.04–4.61 (m, 1H), 4.37–3.89 (m, 2H), 3.37 (broad s, 3H), 2.71–2.55 (m, 2H), 2.10–1.18 (m, 4H); MS (ESI+) 550 (M+H)$^+$.

EXAMPLE 3

5-({[(2'-chloro[1,1'-biphenyl]-4-yl)methyl][(1S)-1,2,3,4-tetrahydro-1-naphthalenyl]amino}carbonyl)-1,2,4-benzenetricarboxylic acid

EXAMPLE 3A

N—[(2'-chloro[1,1'-biphenyl]-4-yl)methyl]-N-[(1S)-1,2,3,4-tetrahydro-1-naphthalenyl]amine 2'-Chloro[1,1'-biphenyl]-4-carbaldehyde and (1S)-1,2,3,4-tetrahydro-1-naphthalenylamine were processed as described in Example 1A to provide the title compound.

¹H NMR (CDCl₃) δ7.50–7.05 (m, 12H), 4.02–3.80 (m, 3H), 2.78 (m, 2H), 2.10–1.90 (m, 3H), 1.76 (m, 1H), 1.53 (broad s, 1H); MS (ESI+) 348 (M+H)⁺.

EXAMPLE 3B 5-({[(2'-chloro[1,1'-biphenyl]-4-yl)methyl][(1S)-1,2,3,4-tetrahydro-1-naphthalenyl]amino}carbonyl)-1,2,4-benzenetricarboxylic acid The product from Example 3A and 1,2,4,5-benzenetetracarboxylic dianhydride were processed as described in Example 1B to provide the title compound.

¹H NMR (DMSO-d₆) δ8.30–7.05 (m, 14H), 5.11–4.61 (m, 1H), 4.37–3.90 (m, 2H), 2.71–2.55 (m, 2H), 2.13–1.40 (m, 4H); MS (ESI−) 583 (M−H)⁻.

EXAMPLE 4

5-({[3',5'-dichloro[1,1'-biphenyl]-4-yl)methyl][(1S)-1,2,3,4-tetrahydro-1-naphthalenyl]amino}carbonyl)-1,2,4-benzenetricarboxylic acid

EXAMPLE 4A

N-[(3',5'-dichloro[1,1'-biphenyl]-4-yl)methyl]-N-[(1S)-1,2,3,4-tetrahydro-1-naphthalenyl]amine 3',5'-Dichloro[1,1'-biphenyl]-4-carbaldehyde and (1S)-1,2,3,4-tetrahydro-1-naphthalenylamine were processed as described in Example 1A to provide the title compound.

¹H NMR (CDCl₃) δ7.50–7.05 (m, 11H), 4.02–3.80 (m, 3H), 2.80 (m, 2H), 2.10–1.90 (m, 3H), 1.76 (m, 1H), 1.56 (broad s, 1H); MS (ESI+) 382 (M+H)⁺.

EXAMPLE 4B 5-({[(3',5'-dichloro[1,1'-biphenyl]-4-yl)methyl][(1S)-1,2,3,4-tetrahydro-1-naphthalenyl]amino}carbonyl)-1,2,4-benzenetricarboxylic acid The product from Example 4A and 1,2,4,5-benzenetetracarboxylic dianhydride were processed as described in Example 1B to provide the title compound.

¹H NMR (DMSO-d₆) δ8.29–7.05 (m, 13H), 5.07–4.61 (m, 1H), 4.37–3.90 (m, 2H), 2.71–2.55 (m, 2H), 2.20–1.38 (m, 4H); MS (ESI+) 618 (M+H)⁺.

EXAMPLE 5

5-({[(2'-methoxy[1,1'-biphenyl]-4-yl)methyl][(1S)-1,2,3,4-tetrahydro-1-naphthalenyl]amino}carbonyl)-1,2,4-benzenetricarboxylic acid

EXAMPLE 5A

N-[(2'-methoxy[1,1'-biphenyl]-4-yl)methyl]-N-[(1S)-1,2,3,4-tetrahydro-1-naphthalenyl]amine 2'-Methoxy[1,1'-biphenyl]-4-carbaldehyde and (1S)-1,2,3,4-tetrahydro-1-naphthalenylamine were processed as described in Example 1A to provide the title compound.

¹H NMR (CDCl₃) δ7.51–6.95 (m, 12H), 4.00–3.82 (m, 3H), 3.80 (s, 3H), 2.80 (m, 2H), 2.10–1.90 (m, 3H), 1.76 (m, 1H), 1.53 (broad s, 1H); MS (ESI+) 344 (M+H)⁺.

EXAMPLE 5B 5-({[(2'-methoxy[1,1'-biphenyl]-4-yl)methyl][(1S)-1,2,3,4-tetrahydro-1-naphthalenyl]amino}carbonyl)-1,2,4-benzenetricarboxylic acid The product from Example 5A and 1,2,4,5-benzenetetracarboxylic dianhydride were processed as described in Example 1B to provide the title compound.

¹H NMR (DMSO-d₆) δ8.29–6.95 (m, 14H), 5.05–4.61 (m, 1H), 4.38–3.87 (m, 2H), 3.78 and 3.70 (2 s, 3H), 2.73–2.55 (m, 2H), 2.20–1.36 (m, 4H); MS (ESI+) 580 (M+H)⁺.

EXAMPLE 6

5-({[(4'-chloro[1,1'-biphenyl]-4-yl)methyl][(1S)-1,2,3,4-tetrahydro-1-naphthalenyl]amino}carbonyl)-1,2,4-benzenetricarboxylic acid

EXAMPLE 6A

N-[(4'-chloro[1,1'-biphenyl]-4-yl)methyl]-N-[(1S)-1,2,3,4-tetrahydro-1-naphthalenyl]amine 4'-Chloro[1,1'-biphenyl]-4-carbaldehyde and (1S)-1,2,3,4-tetrahydro-1-naphthalenylamine were processed as described in Example 1A to provide the title compound.

¹H NMR (CDCl₃) δ7.52–7.05 (m, 12H), 4.02–3.80 (m, 3H), 2.80 (m, 2H), 2.10–1.90 (m, 3H), 1.76 (m, 1H), 1.55 (broad s, 1H); MS (ESI+) 348 (M+H)⁺.

EXAMPLE 6B 5-({[(4'-chloro[1,1'-biphenyl]-4-yl)methyl][(1S)-1,2,3,4-tetrahydro-1-naphthalenyl]amino}carbonyl)-1,2,4-benzenetricarboxylic acid The product from Example 6A and 1,2,4,5-benzenetetracarboxylic dianhydride were processed as described in Example 1B to provide the title compound.

¹H NMR (DMSO-d₆) δ8.29–7.02 (m, 14H), 5.07–4.60 (m, 1H), 4.34–3.87 (m, 2H), 2.73–2.55 (m, 2H), 2.22–1.36 (m, 4H); MS (ESI+) 583 (M+H)⁺.

EXAMPLE 7

5-({[(4'-fluoro[1,1'-biphenyl]-4-yl)methyl][(S)-1,2,3,4-tetrahydro-1-naphthalenyl]amino}carbonyl)-1,2,4-benzenetricarboxylic acid

EXAMPLE 7A

N-[(4'-fluoro[1,1'-biphenyl]-4-yl)methyl]-N-[(1S)-1,2,3,4-tetrahydro-1-naphthalenyl]amine 4'-Fluoro[1,1'-biphenyl]-4-carbaldehyde and (1S)-1,2,3,4-tetrahydro-1-naphthalenylamine were processed as described in Example 1A to provide the title compound.

¹H NMR (CDCl₃) δ7.60–7.00 (m, 12H), 4.02–3.80 (m, 3H), 2.80 (m, 2H), 2.12–1.90 (m, 3H), 1.76 (m, 1H), 1.52 (broad s, 1H); MS (ESI+) 332 (M+H)⁺.

EXAMPLE 7B 5-({[(4'-fluoro[1,1'-biphenyl]-4-yl)methyl][(1S)-1,2,3,4-tetrahydro-1-naphthalenyl]amino}carbonyl)-1,2,4-benzenetricarboxylic acid The product from Example 7A and 1,2,4,5-benzenetetracarboxylic dianhydride were processed as described in Example 1B to provide the title compound.

¹H NMR (DMSO-d₆) δ8.30–7.05 (m, 14H), 5.07–4.60 (m, 1H), 4.34–3.87 (m, 2H, 2.73–2.55 (m, 2H), 2.20–1.36 (m, 4H); MS (ESI+) 568 (M+H)⁺.

EXAMPLE 8

5-({[4'-methoxy[1,1'-biphenyl]-4-yl)methyl][(1S)-1,2,3,4-tetrahydro-1-naphthalenyl]amino}carbonyl)-1,2,4-benzenetricarboxylic acid

EXAMPLE 8A

N-[(4'-methoxy[1,1'-biphenyl]-4-yl)methyl]-N-[(1S)-1,2,3,4-tetrahydro-1-naphthalenyl]amine 4'-Methoxy[1,1'-biphenyl]-4-carbaldehyde and (1S)-1,2,3,4-tetrahydro-1-naphthalenylamine were processed as described in Example 1A to provide the title compound.

EXAMPLE 8B 5-({[(4'-methoxy[1,1'-biphenyl]-4-yl)methyl][(1S)-1,2,3,4-tetrahydro-1-naphthalenyl]amino}carbonyl)-1,2,4-benzenetricarboxylic acid The product from Example 8A and 1,2,4,5-benzenetetracarboxylic dianhydride were processed as described in Example 1B to provide the title compound.

$^1$H NMR (DMSO-d$_6$) δ8.30–6.93 (m, 14H), 5.04–4.61 (m, 1H), 4.33–3.87 (m, 2H), 3.79 and 3.78 (2s, 3H), 2.73–2.55 (m, 2H), 2.20–1.36 (m, 4H); MS (ESI+) 580 (M+H)$^+$.

EXAMPLE 9

5-[((1S)-1,2,3,4-tetrahydro-1-naphthalenyl{[2'-(trifluoromethyl)[1,1'-biphenyl]-4-yl]methyl}amino)carbonyl]-1,2,4-benzenetricarboxylic acid

EXAMPLE 9A

N-[(1S)-1,2,3,4-tetrahydro-1-naphthalenyl]-N-{[2'-(trifluoromethyl)[1,1'-biphenyl]-4-yl]methyl}amine 2'-(Trifluoromethyl)[1,1'-biphenyl]-4-carbaldehyde and (1S)-1,2,3,4-tetrahydro-1-naphthalenylamine were processed as described in Example 1A to provide the title compound.

$^1$H NMR (CDCl$_3$) δ7.75–7.05 (m, 12H), 4.28–3.87 (m, 3H), 2.90 (m, 1H), 2.71 (m 1H), 2.28–2.10 (m, 3H), 1.72 (m, 1H); MS (ESI+) 382 (M+H)$^+$.

EXAMPLE 9B

5-[((1S)-1,2,3,4-tetrahydro-1-naphthalenyl{[2'-(trifluoromethyl)[1,1'-biphenyl]-4-yl]methyl}amino)carbonyl]-1,2,4-benzenetricarboxylic acid The product from Example 9A and 1,2,4,5-benzenetetracarboxylic dianhydride were processed as described in Example 1B to provide the title compound.

$^1$H NMR (DMSO-d$_6$) δ8.30–7.02 (m, 14H), 5.06–4.61 (m, 1H), 4.36–3.90 (m, 2H), 2.73–2.55 (m, 2H), 2.20–1.36 (m, 4H); MS (ESI+) 618 (M+H)$^+$.

EXAMPLE 10

5-({[(2'-methyl[1,1'-biphenyl]-4-yl)methyl][(1S)—1,2,3,4-tetrahydro-1-naphthalenyl]amino}carbonyl)-1,2,4-benzenetricarboxylic acid

EXAMPLE 10A

N-[(2'-methyl[1,1'-biphenyl]-4-yl)methyl]-N-[(1S)-1,2,3,4-tetrahydro-1-naphthalenyl]amine 2'-Methyl[1,1'-biphenyl]-4-carbaldehyde and (1S)-1,2,3,4-tetrahydro-1-naphthalenylamine were processed as described in Example 1A to provide the title compound.

$^1$H NMR (CDCl$_3$) δ7.70–7.05 (m, 12H), 4.28–3.87 (m, 3H), 2.90 (m, 1H), 2.70 (m, 1H), 2.28–2.10 (m, 3H), 2.20 (s, 3H), 1.72 (m, 1H); MS (ESI+) 328 (M+H)$^+$.

EXAMPLE 10B 5-({[(2'-methyl[1,1'-biphenyl]-4-yl)methyl][(1S)-1,2,3,4-tetrahydro-1-naphthalenyl]amino}carbonyl)-1,2,4-benzenetricarboxylic acid The product from Example 10A and 1,2,4,5-benzenetetracarboxylic dianhydride were processed as described in Example 1B to provide the title compound.

$^1$H NMR (DMSO-d$_6$) δ8.29–7.00 (m, 14H), 5.06–4.61 (m, 1H), 4.36–3.92 (m, 2H), 2.78–2.55 (m, 2H), 2.23 and 2.13 (2s, 3H), 2.18–1.36 (m, 4H); MS (ESI+) 564 (M+H)$^+$.

EXAMPLE 11

5-[((1S)-1,2,3,4-tetrahydro-1-naphthalenyl{[4'-(trifluoromethyl)[1,1'-biphenyl]-2-yl]methyl}amino)carbonyl]-1,2,4-benzenetricarboxylic acid

EXAMPLE 11A

N-[(1S)-1,2,3,4-tetrahydro-1-naphthalenyl]-N-{[4'-(trifluoromethyl)[1,1'-biphenyl]-2-yl]methyl}amine 4'-(Trifluoromethyl)[1,1'-biphenyl]-2-carbaldehyde and (1S)-1,2,3,4-tetrahydro-1-naphthalenylamine were processed as described in Example 1A to provide the title compound.

$^1$H NMR (CDCl$_3$) δ8.20 (m, 1H), 7.65–6.95 (m, 11H), 4.10 (t, J=6 Hz, 1H), 3.82 (s, 2H), 2.61 (m, 2H), 2.00–1.43 (m, 4H); MS (ESI+) 382 (M+H)$^+$.

EXAMPLE 11B

5-[((1S)-1,2,3,4-tetrahydro-1-naphthalenyl{[4'-(trifluoromethyl)[1,1'-biphenyl]-2-yl]methyl}amino)carbonyl]-1,2,4-benzenetricarboxylic acid The product from Example 11A and 1,2,4,5-benzenetetracarboxylic dianhydride were processed as described in Example 1B to provide the title compound.

$^1$H NMR (DMSO-d$_6$) δ8.31–6.80 (m, 14H), 4.91–4.52 (m, 1H), 4.22–3.80 (m, 2H), 2.70–2.39 (m, 2H), 1.93–1.20 (m, 4H); MS (ESI+) 618 (M+H)$^+$.

EXAMPLE 12

5-({[(4'-fluoro[1,1'-biphenyl]-2-yl)methyl][(1S)-1,2,3,4-tetrahydro-1-naphthalenyl]amino}carbonyl)-1,2,4-benzenetricarboxylic acid

EXAMPLE 12A

N-[(4'-fluoro[1,1'-biphenyl]-2-yl)methyl]-N-[(1S)-1,2,3,4-tetrahydro-1-naphthalenyl]amine 4'-Fluoro[1,1'-biphenyl]-2-carbaldehyde and (1S)-1,2,3,4-tetrahydro-1-naphthalenylamine were processed as described in Example 1A to provide the title compound.

$^1$ NMR (CDCl$_3$) δ8.20 (m, 1H), 7.49–7.00 (m, 11H), 4.10 (t, J=6 Hz, 1H), 3.90 (s, 2H), 2.63 (m, 2H), 1.98–1.48 (m, 4H); MS (ESI+) 332 (M+H)$^+$.

EXAMPLE 12B 5-({[(4'-fluoro[1,1'-biphenyl]-2-yl)methyl][(1 S)-1,2,3,4-tetrahydro-1-naphthalenyl]amino}carbonyl)-1,2,4-benzenetricarboxylic acid The product from Example 12A and 1,2,4,5-benzenetetracarboxylic dianhydride were processed as described in Example 1B to provide the title compound.

$^1$H NMR (DMSO-d$_6$) δ8.28–6.80 (m, 14H), 4.86–3.87 (m, 3H), 2.70–2.39 (m, 2H), 2.02–1.20 (m, 4H); MS (ESI+) 568 (M+H)$^+$.

EXAMPLE 13

5-({(4-chlorobenzyl)[(1S)-1,2,3,4-tetrahydro-1-naphthalenyl]amino}carbonyl)-1,2,4-benzenetricarboxylic acid

EXAMPLE 13A

N-(4-chlorobenzyl)-N-[(1S)-1,2,3,4-tetrahydro-1-naphthalenyl]amine

4-Chlorobenzaldehyde and (1S)-1,2,3,4-tetrahydro-1-naphthalenylamine were processed as described in Example 1A to provide the title compound.

$^1$H NMR (CDCl$_3$) δ7.68–6.95 (m, 8H), 4.18 (m, 1H), 3.80 (m, 2H), 2.95–2.61 (m, 2H), 2.20–2.05 (m, 3H), 1.70 (m, 1H); MS (ESI+) 272 (M+H)$^+$.

EXAMPLE 13B 5-({(4-chlorobenzyl)[(1S)-1,2,3,4-tetrahydro-1-naphthalenyl]amino}carbonyl)-1,2,4-benzenetricarboxylic acid The product from Example 13A and 1,2,4,5-benzenetetracarboxylic dianhydride were processed as described in Example 1B to provide the title compound.

$^1$H NMR (DMSO-d$_6$) δ8.30–7.00 (m, 10H), 5.00–3.70 (m, 3H), 2.70–2.55 (m, 2H), 2.02–1.40 (m, 4H); MS (ESI+) 508 (M+H)$^+$.

EXAMPLE 14

5-({(4-bromobenzyl)[(1S)-1,2,3,4-tetrahydro-1-naphthalenyl]amino}carbonyl)-1,2,4-benzenetricarboxylic acid

EXAMPLE 14A

N-(4-bromobenzyl)-N-[(1S)-1,2,3,4-tetrahydro-1-naphthalenyl]amine

4-Bromobenzaldehyde and (1S)-1,2,3,4-tetrahydro-1-naphthalenylamine were processed as described in Example 1A to provide the title compound.

$^1$H NMR (CDCl$_3$) δ7.60–7.0 (m, 8H), 4.10 (m, 1H), 3.78 (m, 2H), 2.95–2.61 (m, 2H), 2.20–2.05 (m, 3H), 1.70 (m, 1H); MS (ESI+) 316 (M+H)$^+$.

EXAMPLE 14B 5-({(4-bromobenzyl)[(1S)-1,2,3,4-tetrahydro-1-naphthalenyl]amino}carbonyl)-1,2,4-benzenetricarboxylic acid The product from Example 14A and 1,2,4,5-benzenetetracarboxylic dianhydride were processed as described in Example 1B to provide the title compound.

$^1$H NMR (DMSO-d$_6$) δ8.29–7.00 (m, 10H), 5.00–3.70 (m, 3H), 2.70–2.55 (m, 2H), 2.02–1.35 (m, 4H); MS (ESI+) 552 (M+H)$^+$.

EXAMPLE 15

5-({(3-bromobenzyl)[(1S)-1,2,3,4-tetrahydro-1-naphthalenyl]amino}carbonyl)-1,2,4-benzenetricarboxylic acid

EXAMPLE 15A

N-(3-bromobenzyl)-N-[(1S)-1,2,3,4-tetrahydro-1-naphthalenyl]amine

3-Bromobenzaldehyde and (1S)-1,2,3,4-tetrahydro-1-naphthalenylamine were processed as described in Example 1A to provide the title compound.

$^1$H NMR (CDCl$_3$) δ7.70–7.05 (m, 8H), 4.10 (m, 1H), 3.80 (m, 2H), 2.95–2.61 (m, 2H), 2.20–2.05 (m, 3H), 1.70 (m, 1H); MS (ESI+) 316 (M+H)$^+$.

EXAMPLE 15B 5-({(3-bromobenzyl)[(1S)-1,2,3,4-tetrahydro-1-naphthalenyl]amino}carbonyl)-1,2,4-benzenetricarboxylic acid The product from Example 15A and 1,2,4,5-benzenetetracarboxylic dianhydride were processed as described in Example 1B to provide the title compound.

$^1$H NMR (DMSO-d$_6$) δ8.29–7.00 (m, 10H), 5.00–3.70 (m, 3H), 2.78–2.55 (m, 2H), 2.05–1.37 (m, 4H); MS (ESI+) 552 (M+H)$^+$.

EXAMPLE 16

5-({(3,4-dichlorobenzyl)(1S)-1,2,3,4-tetrahydro-1-naphthalenyl]amino}carbonyl)-1,2,4-benzenetricarboxylic acid

EXAMPLE 16A

N-(3,4-dichlorobenzyl)-N-[(1S)-1,2,3,4-tetrahydro-1-naphthalenyl]amine 3,4-Dichlorobenzaldehyde and (1S)-1,2,3,4-tetrahydro-1-naphthalenylamine were processed as described in Example 1A to provide the title compound.

$^1$H NMR (CDCl$_3$) δ7.68–7.10 (m, 7H), 4.20 (t, J=6 Hz, 1H), 3.80 (m, 2H), 2.95–2.63 (m, 2H), 2.20–2.05 (m, 3H), 1.73 (m, 1H); MS (ESI+) 306 (M+H)$^+$.

EXAMPLE 16B 5-({(3,4-dichlorobenzyl)[(1S)-1,2,3,4-tetrahydro-1-naphthalenyl]amino}carbonyl)-1,2,4-benzenetricarboxylic acid The product from Example 16A and 1,2,4,5-benzenetetracarboxylic dianhydride were processed as described in Example 1B to provide the title compound.

$^1$H NMR (DMSO-d$_6$) δ8.29–7.00 (m, 9H), 5.00–3.80 (m, 3H), 2.72–2.55 (m, 2H), 2.10–1.37 (m, 4H); MS (ESI+) 542 (M+H)$^+$.

EXAMPLE 17

5-({(4-cyanobenzyl)[(1S)-1,2,3,4-tetrahydro-1-naphthalenyl]amino}carbonyl)-1,2,4-benzenetricarboxylic acid

EXAMPLE 17A

4-{[[(1S)-1,2,3,4-tetrahydro-1-naphthalenylamino]methyl}benzonitrile

4-Formylbenzonitrile and (1S)-1,2,3,4-tetrahydro-1-naphthalenylamine were processed as described in Example 1A to provide the title compound.

$^1$H NMR (CDCl$_3$) δ7.78–7.10 (m, 8H), 4.12 (t, J=6 Hz, 1H), 3.90 (m, 2H), 2.95–2.67 (m, 2H), 2.20–2.05 (m, 3H), 1.70 (m, 1H); MS (ESI+) 262 (M+H)$^+$.

EXAMPLE 17B 5-({(4-cyanobenzyl)[(1S)-1,2,3,4-tetrahydro-1-naphthalenyl]amino}carbonyl)-1,2,4-benzenetricarboxylic acid The product from Example 17A and 1,2,4,5-benzenetetracarboxylic dianhydride were processed as described in Example 1B to provide the title compound.

$^1$H NMR (DMSO-d$_6$) δ8.29–7.00 (m, 100H), 5.05–3.94 (m, 3H), 2.72–2.55 (m, 2H), 2.10–1.40 (m, 4H); MS (ESI+) 499 (M+H)$^+$.

EXAMPLE 18

5-({(4-chloro-3-nitrobenzyl)[(1S)-1,2,3,4-tetrahydro-1-naphthalenyl]amino}carbonyl)-1,2,4-benzenetricarboxylic acid

EXAMPLE 18A

N-(4-chloro-3-nitrobenzyl)-N-[(1S)-1,2,3,4-tetrahydro-1-naphthalenyl]amine

4-Chloro-3-nitrobenzaldehyde and (1S)-1,2,3,4-tetrahydro-1-naphthalenylamine were processed as described in Example 1A to provide the title compound.

¹H NMR (CDCl₃) δ8.06 (s, 1H), 7.90 (m, 1H), 7.61–7.50 (m, 2H), 7.28–7.10 (m, 3H), 4.21 (broad s, 1H), 3.90 (m, 2H), 2.95–2.67 (m, 2H), 2.20–2.05 (m, 3H), 1.72 (m, 1H); MS (ESI+) 317 (M+H)⁺.

EXAMPLE 18B 5-({(4-chloro-3-nitrobenzyl)[(1S)-1,2,3,4-tetrahydro-1-naphthalenyl]amino}carbonyl)-1,2,4-benzenetricarboxylic acid The product from Example 18A and 1,2,4,5-benzenetetracarboxylic dianhydride were processed as described in Example 1B to provide the title compound.

¹H NMR (DMSO-d₆) δ8.29–6.87 (m, 9H), 5.00–4.00 (m, 3H), 2.80–2.55 (m, 2H), 2.10–1.40 (m, 4H); MS (ESI+) 553 (M+H)⁺.

EXAMPLE 19

5-({[(4'-fluoro[1,1'-biphenyl]-3-yl)methyl][(1S)-1,2,3,4-tetrahydro-1-naphthalenyl]amino}carbonyl)-1,2,4-benzenetricarboxylic acid

EXAMPLE 19A

N-[(4'-fluoro[1,1'-biphenyl]-3-yl)methyl]-N-[(1S)-1,2,3,4-tetrahydro-1-naphthalenyl]amine 4'-Fluoro[1,1'-biphenyl]-3-carbaldehyde and (1S)-1,2,3,4-tetrahydro-1-naphthalenylamine were processed as described in Example 1A to provide the title compound.

EXAMPLE 19B 5-({[(4'-fluoro[1,1'-biphenyl]-3-yl)methyl][(1S)-1,2,3,4-tetrahydro-1-naphthalenyl]amino}carbonyl)-1,2,4-benzenetricarboxylic acid The product from Example 19A and 1,2,4,5-benzenetetracarboxylic dianhydride were processed as described in Example 1B to provide the title compound.

¹H NMR (DMSO-d₆) δ8.50–7.00 (m, 14H), 5.05–4.63 (m, 1H), 4.40–3.96 (m, 2H), 2.70–2.55 (m, 2H), 2.17–1.37 (m, 4H) MS (ESI+) 568 (M+H)⁺.

EXAMPLE 20

5-({[4-(dimethylamino)benzyl][(1S)-1,2,3,4-tetrahydro-1-naphthalenyl]amino}carbonyl)-1,2,4-benzenetricarboxylic acid

EXAMPLE 20A

N-[4-(dimethylamino)benzyl]-N-[(1S)-1,2,3,4-tetrahydro-1-naphthalenyl]amine 4-(Dimethylamino)benzaldehyde and (1S)-1,2,3,4-tetrahydro-1-naphthalenylamine were processed as described in Example 1A to provide the title compound.

¹H NMR (CDCl₃) δ7.35–7.03 (m, 6H), 6.72 (m, 2H), 3.88–3.70 (m, 3H), 2.91 (s, 6H), 2.78 (m, 2H), 2.08–1.69 (m, 4H), 1.50 (broad s, 1H); MS (ESI+) 281 (M+H)⁺.

EXAMPLE 20B 5-({[4-(dimethylamino)benzyl][(1S)-1,2,3,4-tetrahydro-1-naphthalenyl]amino}carbonyl)-1,2,4-benzenetricarboxylic acid The product from Example 20A and 1,2,4,5-benzenetetracarboxylic dianhydride were processed as described in Example 1B to provide the title compound.

¹H NMR (DMSO-d₆) δ8.25–6.60 (m, 10H), 5.00–3.70 (m, 3H), 3.00 and 2.87 (2s, 6H), 2.70–2.55 (m, 2H), 2.20–1.38 (m, 4H); MS (ESI+) 517 (M+H)⁺.

EXAMPLE 21

5-({(3-chlorobenzyl)[(1S)-1,2,3,4-tetrahydro-1-naphthalenyl]amino}carbonyl)-1,2,4-benzenetricarboxylic acid

EXAMPLE 21A

N-(3-chlorobenzyl)-N-[(1S)-1,2,3,4-tetrahydro-1-naphthalenyl]amine

3-Chlorobenzaldehyde and (1S)-1,2,3,4-tetrahydro-1-naphthalenylamine were processed as described in Example 1A to provide the title compound.

¹H NMR (CDCl₃) δ7.60–7.03 (m, 8H), 4.18 (t, J=6 Hz, 1H), 3.75 (m, 2H), 2.95–2.62 (m, 2H), 2.20–2.05 (m, 3H), 1.70 (m, 1H); MS (ESI+) 272 (M+H)⁺.

EXAMPLE 21B 5-({(3-chlorobenzyl)[(1S)-1,2,3,4-tetrahydro-1-naphthalenyl]amino}carbonyl)-1,2,4-benzenetricarboxylic acid The product from Example 21A and 1,2,4,5-benzenetetracarboxylic dianhydride were processed as described in Example 1B to provide the title compound.

¹H NMR (DMSO-d₆) δ8.28–7.00 (m, 10H), 5.02–3.82 (m, 3H), 2.70–2.55 (m, 2H), 2.20–1.40 (m, 4H); MS (ESI+) 508 (M+H)⁺.

EXAMPLE 22

5-({(3-cyanobenzyl)[(1S)-1,2,3,4-tetrahydro-1-naphthalenyl]amino}carbonyl)-1,2,4-benzenetricarboxylic acid

EXAMPLE 22A

3-{[(1S)-1,2,3,4-tetrahydro-1-naphthalenylamino]methyl}benzonitrile

3-Formylbenzonitrile and (1S)-1,2,3,4-tetrahydro-1-naphthalenylamine were processed as described in Example 1A to provide the title compound.

¹H NMR (CDCl₃) δ8.02 (d, J=7.5 Hz,1H), 7.80 (s, 1H), 7.65–7.10 (m, 6H), 4.18 (broad s, 1H), 3.90 (m, 2H), 2.95–2.62 (m, 2H), 2.20–2.05 (m, 3H), 1.80–1.52 (m, 2H); MS (ESI+) 263 (M+H)⁺.

EXAMPLE 22B 5-({(3-cyanobenzyl)[(1S)-1,2,3,4-tetrahydro-1-naphthalenyl]amino}carbonyl)-1,2,4-benzenetricarboxylic acid The product from Example 22A and 1,2,4,5-benzenetetracarboxylic dianhydride were processed as described in Example 1B to provide the title compound.

¹H NMR (DMSO-d₆) δ8.30–7.00 (m, 10H), 5.02–3.91 (m, 3H), 2.70–2.55 (m, 2H), 2.20–1.40 (m, 4H); MS (ESI+) 499 (M+H)⁺.

EXAMPLE 23

5-({[4-(1-pyrrolidinyl)benzyl][(1S)-1,2,3,4-tetrahydro-1-naphthalenyl]amino}carbonyl)-1,2,4-benzenetricarboxylic acid

EXAMPLE 23A

N-[4-(1-pyrrolidinyl)benzyl]-N-[(S1)-1,2,3,4-tetrahydro-1-naphthalenyl]amine 4-(1-Pyrrolidinyl)benzaldehyde and (1S)-1,2,3,4-tetrahydro-1-naphthalenylamine were processed as described in Example 1A to provide the title compound.

$^1$H NMR (CDCl$_3$) δ7.58–7.05 (m, 6H), 6.49 (m, 2H), 4.12 (t, J=6 Hz, 1H), 3.75 (m, 2H), 3.30–3.10 (m, 5H), 2.95–2.61 (m, 2H), 2.18–1.90 (m, 6H), 1.72 (m, 1H); MS (ESI+) 307 (M+H)$^+$.

EXAMPLE 23B 5-({[4-(1-pyrrolidinyl)benzyl][(1S)-1,2,3,4-tetrahydro-1-naphthalenyl]amino}carbonyl)-1,2,4-benzenetricarboxylic acid The product from Example 23A and 1,2,4,5-benzenetetracarboxylic dianhydride were processed as described in Example 1B to provide the title compound.

$^1$H NMR (DMSO-d$_6$) δ8.26–6.30 (m, 10H), 5.00–3.91 (m, 3H), 3.27–3.10 (m, 4H), 2.70–2.55 (m, 2H), 2.20–1.32 (m, 8H); MS (ESI+) 543 (M+H)$^+$.

EXAMPLE 24

5-[((1S)-1,2,3,4-tetrahydro-1-naphthalenyl{[4'-(trifluoromethyl)[1,1'-biphenyl]-4-yl]methyl}amino)carbonyl]-1,2,4-benzenetricarboxylic acid

EXAMPLE 24A

N-[(1S)-1,2,3,4-tetrahydro-1-naphthalenyl]-N-{[4'-(trifluoromethyl)[1,1'-biphenyl]-4-yl]methyl}amine 4'-(Trifluoromethyl)[1,1'-biphenyl]-4-carbaldehyde and (1S)-1,2,3,4-tetrahydro-1-naphthalenylamine were processed as described in Example 1A to provide the title compound.

$^1$H NMR (CDCl$_3$) δ7.72–7.08 (m, 12H), 4.22 (broad s, 1H), 3.85 (broad s, 2H), 2.95–2.60 (m, 2H), 2.15 (m, 3H), 1.70 (m, 1H); MS (ESI+) 382 (M+H)$^+$.

EXAMPLE 24B

5-[((1S)-1,2,3,4-tetrahydro-1-naphthalenyl{[4'-(trifluoromethyl)[1,1'-biphenyl]-4-yl]methyl}amino)carbonyl]-1,2,4-benzenetricarboxylic acid The product from Example 24A and 1,2,4,5-benzenetetracarboxylic dianhydride were processed as described in Example 1B to provide the title compound.

$^1$H NMR (DMSO-d$_6$) δ8.30–7.00 (m, 14H), 5.10–3.91 (m, 3H), 2.78–2.55 (m, 2H), 2.23–1.40 (m, 4H); MS (ESI+) 618 (M+H)$^+$.

EXAMPLE 25

5-({[4-(3-pyridinyl)benzyl]-N-[(1S)-1,2,3,4-tetrahydro-1-naphthalenyl]amino}carbonyl)-1,2,4-benzenetricarboxylic acid

EXAMPLE 25A

N-[4-(3-pyridinyl)benzyl]-N-[(1S)-1,2,3,4-tetrahydro-1-naphthalenyl]amine 4-(3-Pyridinyl)benzaldehyde and (1S)-1,2,3,4-tetrahydro-1-naphthalenylamine were processed as described in Example 1A to provide the title compound.

$^1$H NMR (CDCl$_3$) δ8.35 (d, J=1.5 Hz, 1H), 8.09 (m, 1H), 7.86 (m, 1H), 7.60–7.08 (m, 9H), 4.05–3.70 (m, 3H), 2.80 (m, 2H), 2.10–1.70 (m, 4H); MS (ESI+) 315 (M+H)$^+$.

EXAMPLE 25B 5-({[4-(3-pyridinyl)benzyl][(1S)-1,2,3,4-tetrahydro-1-naphthalenyl]amino}carbonyl)-1,2,4-benzenetricarboxylic acid The product from Example 25A and 1,2,4,5-benzenetetracarboxylic dianhydride were processed as described in Example 1B to provide the title compound.

$^1$H NMR (DMSO-d$_6$) δ9.01–7.03 (m, 14H), 5.10–3.70 (m, 3H), 2.75–2.55 (m, 2H), 2.30–1.40 (m, 4H); MS (ESI+) 551 (M+H)$^+$.

EXAMPLE 26

5-({([1,1'-biphenyl]-2-ylmethyl)[(1S)-1,2,3,4-tetrahydro-1-naphthalenyl]amino}carbonyl)-1,2,4-benzenetricarboxylic acid

EXAMPLE 26A

N-([1,1'-biphenyl]-2-ylmethyl)-N-[(1S)-1,2,3,4-tetrahydro-1-naphthalenyl]amine

[1,1'-Biphenyl]-2-carbaldehyde and (1S)-1,2,3,4-tetrahydro-1-naphthalenylamine were processed as described in Example 1A to provide the title compound.

EXAMPLE 26B 5-({([1,1'-biphenyl]-2-ylmethyl)[(1S)-1,2,3,4-tetrahydro-1-naphthalenyl]amino}carbonyl)-1,2,4-benzenetricarboxylic acid The product from Example 26A and 1,2,4,5-benzenetetracarboxylic dianhydride were processed as described in Example 1B to provide the title compound.

$^1$H NMR (DMSO-d$_6$) δ8.30–6.80 (m, 15H), 4.82–3.80 (m, 3H), 2.75–2.45 (m, 2H), 2.05–1.33 (m, 4H); MS (ESI+) 550 (M+H)$^+$.

EXAMPLE 27

5-({([1,1'-biphenyl]-3-ylmethyl)[(1S)-1,2,3,4-tetrahydro-1-naphthalenyl]amino}carbonyl)-1,2,4-benzenetricarboxylic acid

EXAMPLE 27A

N-([1,1'-biphenyl]-3-ylmethyl)-N-[(1S)-1,2,3,4-tetrahydro-1-naphthalenyl]amine

[1,1'-Biphenyl]-3-carbaldehyde and (1S)-1,2,3,4-tetrahydro-1-naphthalenylamine were processed as described in Example 1A to provide the title compound.

EXAMPLE 27B 5-({([1,1'-biphenyl-3-ylmethyl)[(1S)-1,2,3,4-tetrahydro-1-naphthalenyl]amino}carbonyl)-1,2,4-benzenetricarboxylic acid The product from Example 27A and 1,2,4,5-benzenetetracarboxylic dianhydride were processed as described in Example 1B to provide the title compound.

$^1$H NMR (DMSO-d$_6$) δ8.38–6.90 (m, 15H), 4.90–4.64 (m, 4H), 4.27–4.18 (m, 1H), 4.00–3.93 (m, 1H), 2.90–2.55 (m, 2H), 2.20–1.4, (m, 4H); MS (ESI+) 550 (M+H)$^+$.

EXAMPLE 28

5-({[(2-methyl[1,1'-biphenyl]-3-yl)methyl][(1S)-1,2,3,4-tetrahydro-1-naphthalenyl]amino}carbonyl)-1,2,4-benzenetricarboxylic acid

EXAMPLE 28A

N-[(2-methyl 1,1'-biphenyl]-3-yl)methyl]-N-[(1S)-1,2,3,4-tetrahydro-1-naphthalenyl]amine 2-Methyl[1,1'-biphenyl]-3-carbaldehyde and (1S)-1,2,3,4-tetrahydro-1-naphthalenylamine were processed as described in Example 1A to provide the title compound.

¹H NMR (CDCl₃) δ7.44–7.06 (m, 12H), 4.02–3.85 (m, 3H), 2.90–2.69 (m, 2H), 2.28 (s, 3H), 2.10–1.70 (m, 4H); MS (DCI+) 238 (M+H)⁺.

EXAMPLE 28B 5-({[(2-methyl[1,1'-biphenyl]-3-yl)methyl][(1S)-1,2, 3,4-tetrahydro-1-naphthalenyl]amino}carbonyl)-1,2, 4-benzenetricarboxylic acid The product from Example 28A and 1,2,4,5-benzenetetracarboxylic dianhydride were processed as described in Example 1B to provide the title compound.

¹H NMR (DMSO-d₆) δ8.70–6.95 (m, 14H), 4.96 (d, 1H), 4.72 (m, 1H), 4.00–3.73 (m, 1H), 3.19 (s, 3H), 2.63–2.38 (m, 2H), 2.00–1.20 (m, 4H); MS (ESI+) 564 (M+H)⁺.

EXAMPLE 29

5-[((1S)-1,2,3,4-tetrahydro-1-naphthalenyl{[4'-(trifluoromethyl)[1,1'-biphenyl]-3-yl]methyl}amino) carbonyl]-1,2,4-benzenetricarboxylic acid

EXAMPLE 29A

N-[(1S)-1,2,3,4-tetrahydro-1-naphthalenyl]-N-{[4'-(trifluoromethyl)[1,1'-biphenyl]-3-yl]methyl}amine 4'-(Trifluoromethyl)[1,1'-biphenyl]-3-carbaldehyde and (1S)-1,2,3,4-tetrahydro-1-naphthalenylamine were processed as described in Example 1A to provide the title compound.

¹H NMR (CDCl₃) δ7.60–7.51 (m, 3H), 7.44–7.35 (m, 4H), 7.16–7.07 (m, 5H), 4.01 (d, 1H, J=13.5 Hz) 3.91 (d, 1H, J=13.5 Hz), 3.86 (t, 1H, J=5 Hz), 2.90–2.67 (m, 2H), 2.10–1.90 (m, 3H), 1.82–1.70 (m, 1H); MS (DCI+) 332 (M+H)⁺.

EXAMPLE 29B

5-[((1S)-1,2,3,4-tetrahydro-1-naphthalenyl{[4'-(trifluoromethyl)[1,1'-biphenyl]-3-yl]methyl}amino) carbonyl]-1,2,4-benzenetricarboxylic acid The product from Example 29A and 1,2,4,5-benzenetetracarboxylic dianhydride were processed as described in Example 1B to provide the title compound.

¹H NMR (DMSO-d₆) δ8.74–7.00 (m, 14H), 5.04–4.86 (m, 1H), 4.80–4.65 (m, 1H), 3.96–3.83 (m, 1H), 2.70–2.37 (m, 2H), 2.08–1.13 (m, 4H); MS (ESI+) 618 (M+H)⁺.

EXAMPLE 30

5-({(cyclohexylmethyl)[(1S)-1,2,3,4-tetrahydro-1-naphthalenyl]amino}carbonyl)-1,2,4-benzenetricarboxylic acid

EXAMPLE 30A

N-(cyclohexylmethyl)-N-[(1S)-1,2,3,4-tetrahydro-1-naphthalenyl]amine

Cyclohexanecarbaldehyde and (1S)-1,2,3,4-tetrahydro-1-naphthalenylamine were processed as described in Example 1A to provide the title compound.

¹H NMR (300 MHz, DMSO-d₆) δ8.8–9.1 (bs, 2H), 7.60–7.67 (m, 1H), 7.15–7.35 (m, 3H), 4.45–4.55 (m, 1H), 2.55–2.9 (m,4H), 1.55–2.15 (m, 10H), 0.8–1.3 (m, 5H); MS (ESI+) 244 (M+H)⁺.

EXAMPLE 30B 5-({(cyclohexylmethyl)[(1S)-1,2,3,4-tetrahydro-1-naphthalenyl]amino}carbonyl)-1,2,4-benzenetricarboxylic acid The product from Example 30A and 1,2,4,5-benzenetetracarboxylic dianhydride were processed as described in Example 1B to provide the title compound.

¹H NMR (300 MHz, DMSO-d₆) δ7.0–8.3 (m, 6H), 4.4–4.65 (m, 1H), 2.4–2.85 (m, 3H), 0.5–2.3 (m, 16H); MS (ESI+) 480 (M+H)⁺.

EXAMPLE 31

5-({(2-phenylpropyl)[(1S)-1,2,3,4-tetrahydro-1-naphthalenyl]amino}carbonyl)-1,2,4-benzenetricarboxylic acid

EXAMPLE 31A

N-(2-phenylpropyl)-N-[(1S)-1,2,3,4-tetrahydro-1-naphthalenyl]amine

Hydratropaldehyde and (1S)-1,2,3,4-tetrahydro-1-naphthalenylamine were processed as described in Example 1A to provide the title compound.

¹H NMR (300 MHz, DMSO-d₆) δ8.4–9.3 (m, 2H), 7.15–7.7 (m, 9H), 4.37–4.6 (m, 1H), 2.9–3.4 (m, 3H+H₂O), 2.6–2.9 (m, 2H), 1.4–2.15 (m, 4H), 1.25–1.35 (m, 3H); (M+H)⁺.

EXAMPLE 31B 5-({(2-phenylpropyl)[(1S)-1,2,3,4-tetrahydro-1-naphthalenyl]amino}carbonyl)-1,2,4-benzenetricarboxylic acid The product from Example 31A and 1,2,4,5-benzenetetracarboxylic dianhydride were processed as described in Example 11B to provide the title compound.

¹H NMR (300 MHz, CD₃OD) δ6.95–8.5 (m, 11H), 4.35–4.7 (m, 1H), 3.5–3.7 (m, 1H), 2.45–3.2 (m, 3H), 1.0–2.1 (m, 8H); MS (ESI+) 502 (M+H)⁺.

EXAMPLE 32

5-({(2-phenylethyl)[(1S)-1,2,3,4-tetrahydro-1-naphthalenyl]amino}carbonyl)-1,2,4-benzenetricarboxylic acid

EXAMPLE 32A

N-(2-phenylethyl)-N-[(1S)-1,2,3,4-tetrahydro-1-naphthalenyl]amine

Phenylacetaldehyde and (1S)-1,2,3,4-tetrahydro-1-naphthalenylamine were processed as described in Example 1A to provide the title compound.

¹H NMR (300 MHz, DMSO-d₆) δ9.0–9.3 (m, 2H), 7.15–7.65 (m, 9H), 4.45–4.55 (m, 1H), 2.65–3.25 (m, 6H), 1.65–2.25 (m, 4H); MS (ESI+) 252 (M+H)⁺.

EXAMPLE 32B 5-({(2-phenylethyl)[(1S)-1,2,3,4-tetrahydro-1-naphthalenyl]amino}carbonyl)-1,2,4-benzenetricarboxylic acid The product from Example 32A and 1,2,4,5-benzenetetracarboxylic dianhydride were processed as described in Example 1B to provide the title compound.

¹H NMR (300 MHz, CD₃OD) δ8.47 (m, 1H), 7.0–7.9 (m, 10H), 4.55–4.65 (m, 1H), 3.35–3.75 (m, 1H), 1.4–3.25 (m, 9H); MS (ESI+) 488 (M+H)⁺.

EXAMPLE 33

5-({benzyl[(1S)-1,2,3,4-tetrahydro-1-naphthalenyl]amino}carbonyl)-1,2,4-benzenetricarboxylic acid

EXAMPLE 33A

N-benzyl-N-[(1S)-1,2,3,4-tetrahydro-1-naphthalenyl]amine

Benzaldehyde and (1S)-1,2,3,4-tetrahydro-1-naphthalenylamine were processed as described in Example 1A to provide the title compound.

¹H NMR (300 MHz, DMSO-d₆) δ9.3–9.6 (m, 2H), 7.15–7.65 (m, 9H), 4.35–4.5 (m, 1H), 4.13–4.23 (m, 2H), 2.65–2.95 (m, 2H), 1.65–2.3 (m, 4H); MS (ESI+) 238 (M+H)⁺.

EXAMPLE 33B 5-({benzyl[(1S)-1,2,3,4-tetrahydro-1-naphthalenyl]amino}carbonyl)-1,2,4-benzenetricarboxylic acid The product from Example 33A and 1,2,4,5-benzenetetracarboxylic dianhydride were processed as described in Example 1B to provide the title compound.

¹H NMR (300 MHz, DMSO-d₆) δ7.0–8.4 (m, 11H), 3.3–5.5 (m, 3H), 2.5–2.7 (m, 2H), 1.3–2.2 (m, 4H); MS (ESI+) 474 (M+H)⁺.

EXAMPLE 34

5-({(3-methoxybenzyl)[(1S)-1,2,3,4-tetrahydro-1-naphthalenyl]amino}carbonyl)-1,2,4-benzenetricarboxylic acid

EXAMPLE 34A

N-(3-methoxybenzyl)-N-[(1S)-1,2,3,4-tetrahydro-1-naphthalenyl]amine

3-Methoxybenzaldehyde and (1S)-1,2,3,4-tetrahydro-1-naphthalenylamine were processed as described in Example 1A to provide the title compound.

¹H NMR (300 MHz, DMSO-d₆) δ9.3–9.5 (m, 2H), 6.95–7.57 (m, 8H), 4.35–4.45 (m, 1H), 4.07–4.15 (m, 2H), 3.78 (s, 3H), 2.6–2.95 (m, 2H), 1.65–2.3 (m, 4H); MS (ESI+) 268 (M+H)⁺.

EXAMPLE 34B 5-({(3-methoxybenzyl)[(1S)-1,2,3,4-tetrahydro-1-naphthalenyl]amino}carbonyl)-1,2,4-benzenetricarboxylic acid The product from Example 34A and 1,2,4,5-benzenetetracarboxylic dianhydride were processed as described in Example 1B to provide the title compound.

¹H NMR (300 MHz, DMSO-d₆) δ6.6–8.3 (m, 10H), 4.05–5.5 (m, 3H), 3.65–3.85 (m, 3H), 2.5–2.7 (m, 2H), 1.2–2.2 (4H); MS (ESI+) 504 (M+H)⁺.

EXAMPLE 35

5-[((1S)-1,2,3,4-tetrahydro-1-naphthalenyl{3-[3-(trifluoromethyl)phenoxy]benzyl}amino)carbonyl]-1,2,4-benzenetricarboxylic acid

EXAMPLE 35A

N-[(1S)-1,2,3,4-tetrahydro-1-naphthalenyl]-N-{3-[3-(trifluoromethyl)phenoxy]benzyl}amine 3-[3-(Trifluoromethyl)phenoxy]benzaldehyde and (1S)-1,2,3,4-tetrahydro-1-naphthalenylamine were processed as described in Example 1A to provide the title compound.

¹H NMR (300 MHz, CDCl₃) δ6.85–7.5 (m, 12H), 3.8–3.97 (m, 3H), 2.65–2.95 (m, 2H), 1.6–2.1 (m, 5H); MS (ESI+) 398 (M+H)⁺.

EXAMPLE 35B

5-[((1S)-1,2,3,4-tetrahydro-1-naphthalenyl{3-[3-(trifluoromethyl)phenoxy]benzyl}amino)carbonyl]-1,2,4-benzenetricarboxylic acid The product from Example 35A and 1,2,4,5-benzenetetracarboxylic dianhydride were processed as described in Example 1B to provide the title compound.

¹H NMR (300 MHz, DMSO-d₆) d 13.9 (bs, 1H), 6.65–8.3 (m, 14H), 3.9–5.65 (m, 3H), 2.5–2.7 (m, 2H), 1.3–2.1 (m, 4H); MS (ESI+) 634 (M+H)⁺.

EXAMPLE 36

5-({(3-phenoxybenzyl)[(1S)-1,2,3,4-tetrahydro-1-naphthalenyl]amino}carbonyl)-1,2,4-benzenetricarboxylic acid

EXAMPLE 36A

N-(3-phenoxybenzyl)-N-[(1S)-1,2,3,4-tetrahydro-1-naphthalenyl]amine

3-Phenoxybenzaldehyde and (1S)-1,2,3,4-tetrahydro-1-naphthalenylamine were processed as described in Example 1A to provide the title compound.

¹H NMR (300 MHz, CDCl₃) δ6.8–7.53 (13H), 3.77–4.1 (m, 3H), 2.6–2.95 (m, 2H), 1.4–2.2 (m, 5H); MS (ESI+) 330 (M+H)⁺.

EXAMPLE 36B 5-({(3-phenoxybenzyl)[(1S)-1,2,3,4-tetrahydro-1-naphthalenyl]amino}carbonyl)-1,2,4-benzenetricarboxylic acid The product from Example 36A and 1,2,4,5-benzenetetracarboxylic dianhydride were processed as described in Example 1B to provide the title compound.

¹H NMR (300 MHz, DMSO-d₆) δ6.5–8.3 (m, 15H), 3.8–5.6 (m, 3H), 2.5–2.7 (m, 2H), 1.6–2.1 (m, 4H); MS (ESI+) 566 (M+H)⁺.

EXAMPLE 37

5-({[3-(4-methoxyphenoxy)benzyl][(1S)-1,2,3,4-tetrahydro-1-naphthalenyl]amino}carbonyl)-1,2,4-benzenetricarboxylic acid

EXAMPLE 37A

N-[3-(4-methoxyphenoxy)benzyl]-N-[(1S)-1,2,3,4-tetrahydro-1-naphthalenyl]amine 3-(4-Methoxyphenoxy)benzaldehyde and (1S)-1,2,3,4-tetrahydro-1-naphthalenylamine were processed as described in Example 1A to provide the title compound.

¹H NMR (300 MHz, CDCl₃) δ6.8–7.53 (12H), 3.77–4.1 (m, 6H), 2.6–2.95 (m, 2H), 1.4–2.2 (m, 5H); MS (ESI+) 360 (M+H)⁺.

EXAMPLE 37B 5-({[3-(4-methoxyphenoxy)benzyl][(1S)-1,2,3,4-tetrahydro-1-naphthalenyl]amino}carbonyl)-1,2,4-benzenetricarboxylic acid The product from Example 37A and 1,2,4,5-benzenetetracarboxylic dianhydride were processed as described in Example 1B to provide the title compound.

$^1$H NMR (300 MHz, DMSO-d$_6$) δ6.5–8.3 (m, 14H), 3.8–5.6 (m, 3H), 3.7–3.8 (m, 3H), 2.5–2.7 (m, 2H), 1.6–2.1 (m, 4H); MS (ESI+) 596 (M+H)$^+$.

EXAMPLE 38

5-({[3-(3,4-dichlorophenoxy)benzyl][(1S)-1,2,3,4-tetrahydro-1-naphthalenyl]amino}carbonyl)-1,2,4-benzenetricarboxylic acid

EXAMPLE 38A

N-[3-(3,4-dichlorophenoxy)benzyl]-N-[(1S)-1,2,3,4-tetrahydro-1-naphthalenyl]amine 3-(3,4-Dichlorophenoxy)benzaldehyde and (1S)-1,2,3,4-tetrahydro-1-naphthalenylamine were processed as described in Example 1A to provide the title compound.
$^1$H NMR (300 MHz, CDCl$_3$) δ6.8–7.4 (m, 1H), 3.75–3.97 (m, 3H), 2.65–2.9 (m, 2H), 1.4–2.1 (m, 5H); MS (ESI+) 398 (M+H)$^+$.

EXAMPLE 38B 5-({[3-(3,4-dichlorophenoxy)benzyl][(1S)-1,2,3,4-tetrahydro-1-naphthalenyl]amino}carbonyl)-1,2,4-benzenetricarboxylic acid The product from Example 38A and 1,2,4,5-benzenetetracarboxylic dianhydride were processed as described in Example 1B to provide the title compound.
$^1$H NMR (300 MHz, DMSO-d$_6$) δ13.9 (bs, 1H), 6.65–8.3 (m, 13H), 3.85–5.65 (m, 3H), 2.5–2.7 (m, 2H), 1.3–2.2 (m, 4H); MS (ESI+) 634 (M+H)$^+$.

EXAMPLE 39

5-({[3-(4-chlorophenoxy)benzyl][(1S)-1,2,3,4-tetrahydro-1-naphthalenyl]amino}carbonyl)-1,2,4-benzenetricarboxylic acid

EXAMPLE 39A

N-[3-(4-chlorophenoxy)benzyl]-N-[(1S)-1,2,3,4-tetrahydro-1-naphthalenyl]amine 3-(4-Chlorophenoxy)benzaldehyde and (1S)-1,2,3,4-tetrahydro-1-naphthalenylamine were processed as described in Example 1A to provide the title compound.
$^1$H NMR (300 MHz, CDCl$_3$) δ6.85–7.37 (m, 12H), 3.75–3.95 (m, 3H), 2.65–2.9 (m, 2H), 1.4–2.1 (m, 5H); MS (ESI+) 364 (M+H)$^+$.

EXAMPLE 39B 5-({[3-(4-chlorophenoxy)benzyl][(1S)-1,2,3,4-tetrahydro-1-naphthalenyl]amino}carbonyl)-1,2,4-benzenetricarboxylic acid The product from Example 39A and 1,2,4,5-benzenetetracarboxylic dianhydride were processed as described in Example 1B to provide the title compound.
$^1$H NMR (300 MHz, DMSO-d$_6$) δ13.9 (bs, 1H), 6.6–8.3 (m, 14H), 3.9–5.65 (m, 3H), 2.5–2.7 (m, 2H), 1.3–2.2 (m, 4H); MS (ESI+) 600 (M+H)$^+$.

EXAMPLE 40

5-({[3-(4-tert-butylphenoxy)benzyl][(1S)-1,2,3,4-tetrahydro-1-naphthalenyl]amino}carbonyl)-1,2,4-benzenetricarboxylic acid

EXAMPLE 40A

N-[3-(4-tert-butylphenoxy)benzyl]-N-[(1S)-1,2,3,4-tetrahydro-1-naphthalenyl]amine 3-(4-tert-Butylphenoxy)benzaldehyde and (1S)-1,2,3,4-tetrahydro-1-naphthalenylamine were processed as described in Example 1A to provide the title compound.
$^1$H NMR (300 MHz, CDCl$_3$) δ6.85–7.37 (m, 12H), 3.75–3.95 (m, 3H), 2.65–2.9 (m, 2H), 1.45–2.15 (m, 5H), 1.32 (s, 9H); MS (ESI+) 386 (M+H)$^+$.

EXAMPLE 40B 5-({[3-(4-tert-butylphenoxy)benzyl][(1S)-1,2,3,4-tetrahydro-1-naphthalenyl]amino}carbonyl)-1,2,4-benzenetricarboxylic acid The product from Example 40A and 1,2,4,5-benzenetetracarboxylic dianhydride were processed as described in Example 1B to provide the title compound.
$^1$H NMR (300 MHz, DMSO-d$_6$) δ6.65–8.3 (m, 14H), 3.75–5.6 (m, 3H), 2.5–2.7 (m, 2H), 1.35–2.1 (m, 4H), 1.25–1.35 (m, 9H); MS (ESI+) 622 (M+H)$^+$.

EXAMPLE 41

5-({[3-(4-methylphenoxy)benzyl][(1S)-1,2,3,4-tetrahydro-1-naphthalenyl]amino}carbonyl)-1,2,4-benzenetricarboxylic acid

EXAMPLE 41A

N-[3-(4-methylphenoxy)benzyl]-N-[(1S)-1,2,3,4-tetrahydro-1-naphthalenyl]amine 3-(4-Methylphenoxy)benzaldehyde and (1S)-1,2,3,4-tetrahydro-1-naphthalenylamine were processed as described in Example 1A to provide the title compound.
$^1$H NMR (300 MHz, CDCl$_3$) δ6.82–7.47 (m, 12H), 3.77–3.95 (m, 3H), 2.65–2.9 (m, 2H), 2.35 (s, 3H), 1.4–2.1 (m, 5H); MS (ESI+) 344 (M+H)$^+$.

EXAMPLE 41B 5-({[3-(4-methylphenoxy)benzyl][(1S)-1,2,3,4-tetrahydro-1-naphthalenyl]amino}carbonyl)-1,2,4-benzenetricarboxylic acid The product from Example 41A and 1,2,4,5-benzenetetracarboxylic dianhydride were processed as described in Example 1B to provide the title compound.
$^1$H NMR (300 MHz, DMSO-d$_6$) δ13.9 (bs, 1H), 6.55–8.3 (m, 14H), 3.35–5.6 (m, 3H), 2.55–2.7 (m, 2H), 2.25–2.35 (m, 3H), 1.3–2.1 (m, 4H); MS (ESI+) 580 (M+H)$^+$.

EXAMPLE 42

5-({[3-(3.5-dichlorophenoxy)benzyl][(1S)-1,2,3,4-tetrahydro-1-naphthalenyl]amino}carbonyl)-1,2,4-benzenetricarboxylic acid

EXAMPLE 42A

N-[3-(3,5-dichlorophenoxy)benzyl]-N-[(1S)-1,2,3,4-tetrahydro-1-naphthalenyl]amine 3-(3,5-Dichlorophenoxy)benzaldehyde and (1S)-1,2,3,4-tetrahydro-1-naphthalenylamine were processed as described in Example 1A to provide the title compound.
MS (ESI+) 398 (M+H)$^+$.

EXAMPLE 42B 5-({[3-(3,5-dichlorophenoxy)benzyl][(1S)-1,2,3,4-tetrahydro-1-naphthalenyl]amino}carbonyl)-1,2,4-benzenetricarboxylic acid The product from Example 42A and 1,2,4,5-benzenetetracarboxylic dianhydride were processed as described in Example 1B to provide the title compound.

¹H NMR (300 MHz, DMSO-d₆) δ13.9 (bs, 1H), 6.75–8.3 (m, 13H), 3.9–5.65 (m, 3H), 2.55–2.7 (m, 2H), 1.3–2.15 (m, 4H); MS (ESI+) 634 (M+H)⁺.

EXAMPLE 43

5-({(3-benzylbenzyl)[(1S)-1,2,3,4-tetrahydro-1-naphthalenyl]amino}carbonyl)-1,2,4-benzenetricarboxylic acid

EXAMPLE 43A

N-(3-benzylbenzyl)-N-[(1S)-1,2,3,4-tetrahydro-1-naphthalenyl]amine

The product from Example 45C (759 mg, 2.21 mmol) in triethylsilane (5 mL) was treated with trifluoroacetic acid (5 mL, xs). After stirring for 30 minutes at room temperature, the reaction mixture was diluted with ethyl acetate and basified with concentrated NH₄OH. The separated organic phase was washed with brine, dried (Na₂SO₄), filtered and the filtrate concentrated under reduced pressure to provide the title compound as an oil (715 mg).

¹H NMR (300 MHz, CDCl₃) δ7.0–7.35 (m, 13H), 3.75–4.0 (m, 5H), 2.6–2.9 (m, 2H), 1.4–2.1 (m, 5H), 0.85–1.0 (m, EtSiH), 0.45–0.65 (m, EtSiH); MS (DCI/NH₃) 328 (M+H)⁺.

EXAMPLE 43B 5-({(3-benzylbenzyl)[(1S)-1,2,3,4-tetrahydro-1-naphthalenyl]amino}carbonyl)-1,2,4-benzenetricarboxylic acid The product from Example 43A and 1,2,4,5-benzenetetracarboxylic dianhydride were processed as described in Example 1B to provide the title compound.

¹H NMR (300 MHz, DMSO-d₆) δ6.75–8.3 (m, 15H), 3.7–5.5 (m, 5H), 2.5–2.65 (m, 2H), 1.25–2.1 (m, 4H); MS (ESI+) 564 (M+H)⁺.

EXAMPLE 44

5-({(9H-fluoren-2-ylmethyl)[(1S)-1,2,3,4-tetrahydro-1-naphthalenyl]amino}carbonyl)-1,2,4-benzenetricarboxylic acid

EXAMPLE 44A

N-(9H-fluoren-2-ylmethyl)-N-[(1S)-1,2,3,4-tetrahydro-1-naphthalenyl]amine

The product from Example 46C was processed as described in Example 43A to provide the title compound.

¹H NMR (300 MHz, CDCl₃) δ7.05–7.85 (m, 11H), 3.85–4.07 (m, 5H), 2.67–2.93 (m, 2H), 1.4–2.15 (m, 5H); MS (DCI/NH₃) 326 (M+H)⁺.

EXAMPLE 44B 5-({(9H-fluoren-2-ylmethyl)[(1S)-1,2,3,4-tetrahydro-1-naphthalenyl]amino}carbonyl)-1,2,4-benzenetricarboxylic acid The product from Example 44A and 1,2,4,5-benzenetetracarboxylic dianhydride were processed as described in Example 1B to provide the title compound.

¹H NMR (300 MHz, DMSO-d₆) δ13.9 (bs, 1H), 7.0–8.3 (m, 13H), 3.4–5.6 (5H), 2.5–2.7 (2H), 1.3–2.2 (4H); MS (ESI+) 562 (M+H)⁺.

EXAMPLE 45

5-({{3-[hydroxy(phenyl)methyl]benzyl}[(1S)-1,2,3,4-tetrahydro-1-naphthalenyl]amino}carbonyl)-1,2,4-benzenetricarboxylic acid

EXAMPLE 45A

[3-(hydroxymethyl)phenyl](phenyl)methanone 3-benzoylbenzoic acid (6.26 g, 27.7 mmol) was carefully added in several portions to borane-N,N-diethylaniline complex (7.38 mL, 41.5 mmol) in anhydrous THF (60 mL) at ambient temperature. After 15 minutes, the reaction mixture was heated at reflux for 5 hours and then cooled to ambient temperature. The reaction mixture was diluted with diethyl ether, quenched with 1N HCl and the separated aqueous phase was extracted with diethyl ether. The organic layers were combined, washed with 1N HCl, brine, dried (Na₂SO₄), filtered and the filtrate concentrated under reduced pressure. The residue was purified by flash chromatography (silica gel, 40% ethyl acetate/hexanes) to provide a mixture of the title compound and the diol, [3-(hydroxymethyl)phenyl](phenyl)methanol, as a colorless oil (3.59 g).

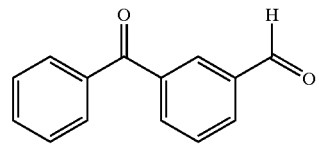

EXAMPLE 45B 3-benzoylbenzaldehyde

The mixture from Example 45A (3.59 g) and celite (diatomaceous earth) in anhydrous CH₂Cl₂ (100 mL) were treated with and pyridinium chlorochromate (12.6 g, 58.6 mmol). After stirring for 18 hours, the reaction mixture was filtered and the filtrate concentrated under reduced pressure. The residue was taken up in ethyl acetate, washed with 1N HCl, saturated NaHCO₃, brine, dried (Na₂SO₄), filtered and the filtrate concentrated under reduced pressure. The residue was purified by flash chromatography (silca gel, 30% ethyl acetate/hexanes) to provide the title compound as a colorless oil (2.05 g, 35% yield).

¹H NMR (300 MHz, CDCl₃) δ10.1(s, 1H), 8.25–8.3 (m, 1H), 8.05–8.15 (m 2H), 7.75–7.85 (m, 2H), 7.6–7.72 (m, 2H), 7.47–7.55 (m, 2H); MS (DCI/NH₃) 228 (M+NH₄)⁺.

EXAMPLE 45C phenyl(3-{[(1S)-1,2,3,4-tetrahydro-1-naphthalenylamino]methyl}phenyl)methanol The product from Example 45B (2.04 g, 9.70 mmol) in absolute ethanol (25 mL) was treated with (1S)-1,2,3,4-tetrahydro-1-naphthalenylamine (1.39 mL, 9.70 mmol). After 3 hours, the mixture was treated with sodium borohydride and the reaction mixture was allowed to stir at room temperature for 16 hours. The reaction mixture was quenched with 1N NaOH, diluted with ethyl acetate and the separated aqueous phase was extracted with ethyl acetate. The organic layers were combined, washed with water, brine, dried (Na₂SO₄), filtered and the filtrate concentrated under reduced pressure. The residue was purified by flash chromatography (silica gel, 7% methanol/CH$_2$Cl$_2$) to provide the title compound as a colorless oil (2.85 g, 86% yield).

$^1$H NMR (300 MHz, CDCl$_3$) δ7.05–7.5 (m, 13H), 5.85 (s, 1H), 3.8–3.95 (m, 3H), 2.65–2.9 (m, 2H), 1.5–2.1 (m, 6H); MS (DCI/NH$_3$) 344 (M+H)$^+$.

EXAMPLE 45D 5-({{3-[hydroxy(phenyl)methyl]benzyl}[(1S)-1,2,3,4-tetrahydro-1-naphthalenyl]amino}carbonyl)-1,2,4-benzenetricarboxylic acid The product from Example 45C and 1,2,4,5-benzenetetracarboxylic dianhydride were processed as described in Example 1B to provide the title compound.

$^1$H NMR (300 MHz, DMSO-d$_6$) δ13.85 (bs, 1H), 6.8–8.3 (m, 15H), 5.55–5.75 (m, 1H), 3.6–5.3 (m, 3H), 2.5–2.6 (m, 2H), 1.2–2.05 (m, 5H); MS (ESI-) 578 (M–H)$^-$.

EXAMPLE 46

5-({[(9-hydroxy-9H-fluoren-2-yl)methyl][(1S)-1,2,3,4-tetrahydro-1-naphthalenyl]amino}carbonyl)-1,2,4-benzenetricarboxylic acid

EXAMPLE 46A 2-(hydroxymethyl)-9H-fluoren-9-one

9-Oxo-9H-fluorene-2-carboxylic acid, purchased from Aldrich, was processed as described in Example 45A to provide the title compound.

EXAMPLE 46B 9-oxo-9H-fluorene-2-carbaldehyde

The product from Example 46A was processed as described in Example 45B to provide the title compound.

EXAMPLE 46C

2-{[(1S)-1,2,3,4-tetrahydro-1-naphthalenylamino]methyl}-9H-fluoren-9-ol

The product from Example 46B and (1S)-1,2,3,4-tetrahydro-1-naphthalenylamine were processed as described in Example 45C to provide the title compound.

$^1$H NMR (300 MHz, CDCl$_3$) δ7.05–7.73 (m, 11H), 5.57 (s, 1H), 3.84–4.03 (m, 3H), 2.67–2.91 (m, 2H), 1.6–2.1 (m, 6H); MS (DCI/NH$_3$) 342 (M+H)$^+$.

EXAMPLE 46D 5-({[(9-hydroxy-9H-fluoren-2-yl)methyl][(1S)-1,2,3,4-tetrahydro-1-naphthalenyl]amino}carbonyl)-1,2,4-benzenetricarboxylic acid The product from Example 46C and 1,2,4,5-benzenetetracarboxylic dianhydride were processed as described in Example 1B to provide the title compound.

$^1$H NMR (300 MHz, DMSO-d$_6$) δ7.0–8.3 (m, 13H), 3.85–5.65 (m, 4H), 2.55–2.7 (m, 2H), 1.25–2.2 (m, 5H); MS (ESI-) 576 (M–H)$^-$.

EXAMPLE 47

5-({(3-benzoylbenzyl)[(1S)-1,2,3,4-tetrahydro-1-naphthalenyl]amino}carbonyl)-1,2,4-benzenetricarboxylic acid

EXAMPLE 47A phenyl(3-{[(1S)-1,2,3,4-tetrahydro-1-naphthalenylamino]methyl}phenyl)methanone The product from Example 45C (319 mg, 0.84 mmol) and triethylamine (468 µL, 3.36 mmol) in DMSO (10 mL) were treated with sulfur trioxide pyridine complex (535 mg, 3.36 mmol). After stirring for 2 hours at room temperature, the reaction mixture was partitioned between water and diethyl ether. The aqueous phase was extracted with diethyl ether. The organic extracts were combined, washed with brine, dried (Na$_2$SO$_4$), filtered, and the filtrate concentrated under reduced pressure. The residue was purified by flash chromatography (silica gel, 20% ethyl acetate/hexanes) to provide a colorless oil (106 mg, 37% yield).

$^1$H NMR (300 MHz, CDCl$_3$) δ7.05–7.85 (m, 13H), 3.85–4.05 (m, 3H), 2.65–2.9 (m, 2H), 1.6–2.2 (m, 5H); MS (DCI/NH$_3$) 342 (M+H)$^+$.

EXAMPLE 47B 5-({(3-benzoylbenzyl)[(1S)-1,2,3,4-tetrahydro-1-naphthalenyl]amino}carbonyl)-1,2,4-benzenetricarboxylic acid The product from Example 47A and 1,2,4,5-benzenetetracarboxylic dianhydride were processed as described in Example 1B to provide the title compound.

$^1$H NMR (300 MHz, DMSO-d$_6$) δ7.0–8.3 (m, 15H), 4.0–5.7 (m, 3H), 2.55–2.8 (m, 2H), 1.3–2.2 (m, 4H); MS (ESI-) 576 (M–H)$^-$.

EXAMPLE 48

5-({[3-(4-nitrophenoxy)benzyl][(1S)-1,2,3,4-tetrahydro-1-naphthalenyl]amino}carbonyl)-1,2,4-benzenetricarboxylic acid

EXAMPLE 48A 3-(4-Nitrophenoxy)benzaldehyde

3-Hydroxybenzaldehyde (1.15 g, 9.4 mmol), 1-fluoro-4-nitrobenzene (1.0 mL, 9.4 mmol) and K$_2$CO$_3$ (2.61 g, 19 mmol) were combined in DMF (20 mL) and heated at 80° C. After 6 hours, the reaction mixture was cooled to room temperature and partitioned between water and diethyl ether. The separated aqueous phase was extracted with diethyl ether. The organic layers were combined, washed with 1N NaOH, brine, dried (MgSO$_4$), filtered and the filtrate concentrated under reduced pressure to provide the title compound as a yellow solid (1.98 g).

$^1$H NMR (300 MHz, CDCl$_3$) δ10.0 (s, 1H), 8.2–8.27 (m, 2H), 7.75–7.78 (m, 1H), 7.55–7.65 (m, 2H), 7.35–7.4 (m, 1H), 7.05–7.1 (m, 2H); MS (DCI/$_3$) 261 (M+NH$_4$)$^+$.

EXAMPLE 48B

N-[3-(4-nitrophenoxy)benzyl]-N-[(1S)-1,2,3,4-tetrahydro-1-naphthalenyl]amine

The product from Example 48A and (1S)-1,2,3,4-tetrahydro-1-naphthalenylamine were processed as described in Example 1A to provide the title compound.

$^1$H NMR (300 MHz, CDCl$_3$) δ6.95–8.3 (m, 12H), 3.82–4.02 (m, 3H), 2.65–2.9 (m, 2H), 1.4–2.2 (m, 5H); MS (DCI/NH$_3$) 375 (M+H)$^+$.

EXAMPLE 48C 5-({[3-(4-nitrophenoxy)benzyl][(1S)-1,2,3,4-tetrahydro-1-naphthalenyl]amino}carbonyl)-1,2,4-benzenetricarboxylic acid The product from Example 48B and 1,2,4,5-benzenetetracarboxylic dianhydride were processed as described in Example 1B to provide the title compound.

$^1$H NMR (300 MHz, DMSO-d$_6$) δ6.75–8.3 (m, 14H), 3.85–5.7 (m, 3H), 2.5–2.75 (m, 2H), 1.3–2.2 (m, 4H); MS (ESI+) 611 (M+H)$^+$.

EXAMPLE 49

5-({[(9-oxo-9H-fluoren-2-yl)methyl][(1S)-1,2,3,4-tetrahydro-1-naphthalenyl]amino}carbonyl)-1,2,4-benzenetricarboxylic acid

EXAMPLE 49A

2-{[(1S)-1,2,3,4-tetrahydro-1-naphthalenylamino]methyl}-9H-fluoren-9-one

The product from Example 46C and sulfur trioxide pyridine were processed as described in Example 47A to provide the title compound.

EXAMPLE 49B 5-({[(9-oxo-9H-fluoren-2-yl)methyl][(1S)-1,2,3,4-tetrahydro-1-naphthalenyl]amino}carbonyl)-1,2,4-benzenetricarboxylic acid The product from Example 49A and 1,2,4,5-benzenetetracarboxylic dianhydride were processed as described in Example 1B to provide the title compound.

$^1$H NMR (300 MHz, DMSO-d$_6$) δ7.0–8.35 (m, 13H), 3.9–5.6 (m,3H), 2.55–2.75 (m, 2H), 1.35–2.2 (m, 4H); MS (ESI–) 574 (M–H)$^-$.

EXAMPLE 50

5-({[3-(4-cyanophenoxy)benzyl][(1S)-1,2,3,4-tetrahydro-1-naphthalenyl]amino}carbonyl)-1,2,4-benzenetricarboxylic acid

EXAMPLE 50A 4-(3-Formylphenoxy)benzonitrile

4-Fluorobenzonitrile and 3-hydroxybenzaldehyde were processed as described in Example 48A to provide the title compound.

EXAMPLE 50B 4-(3-{[(1S)-1,2,3,4-tetrahydro-1-naphthalenylamino]methyl}phenoxy)benzonitrile The product from Example 50A and (1S)-1,2,3,4-tetrahydro-1-naphthalenylamine were processed as described in Example 1A to provide the title compound.

$^1$H NMR (300 MHz, CDCl$_3$) δ6.9–7.65 (m, 12H), 3.8–4.0 (m, 3H), 2.65–2.9 (m, 2H), 1.3–2.2 (m, 5H); MS (DCI/NH$_3$) 355 (M+H)$^+$.

EXAMPLE 50C 5-({[3-(4-cyanophenoxy)benzyl][(1S)-1,2,3,4-tetrahydro-1-naphthalenyl]amino}carbonyl)-1,2,4-benzenetricarboxylic acid The product from Example 50B and 1,2,4,5-benzenetetracarboxylic dianhydride were processed as described in Example 1B to provide the title compound.

$^1$H NMR (300 MHz, DMSO-d$_6$) δ13.9 (bs, 1H), 6.7–8.3 (m, 14H), 3.9–5.7 (m, (m, 3H), 2.55–2.75 (m, 2H), 1.3–2.2 (m, 4H); MS (ESI–) 589 (M–H)$^-$.

EXAMPLE 51

5-({[3-(benzyloxy)benzyl][(1S)-1,2,3,4-tetrahydro-1-naphthalenyl]amino}carbonyl)-1,2,4-benzenetricarboxylic acid

EXAMPLE 51A

N-[3-(benzyloxy)benzyl]-N-[(1S)-1,2,3,4-tetrahydro-1-naphthalenyl]amine 3-(Benzyloxy)benzaldehyde and (1S)-1,2,3,4-tetrahydro-1-naphthalenylamine were processed as described in Example 1A to provide the title compound.

$^1$H NMR (300 MHz, DMSO-d$_6$) δ9.35–9.65 (m, 2H), 7.03–7.58 (m, 13H), 5.13 (s, 2H), 4.35–4.45 (m, 1H), 4.1–4.18 (m, 2H), 2.65–2.93 (m, 2H), 1.65–2.3 (m, 4H); MS (DCI/NH$_3$) 344 (M+H)$^+$.

EXAMPLE 51B 5-({[3-(benzyloxy)benzyl][(1S)-1,2,3,4-tetrahydro-1-naphthalenyl]amino}carbonyl)-1,2,4-benzenetricarboxylic acid The product from Example 51A and 1,2,4,5-benzenetetracarboxylic dianhydride were processed as described in Example 1B to provide the title compound.

$^1$H NMR (300 MHz, DMSO-d$_6$) δ6.55–8.3 (m, 15H), 3.75–5.55 (m, 5H), 2.5–2.7 (m, 2H), 1.3–2.1 (m, 4H); MS (ESI–) 578 (M–H)$^-$.

EXAMPLE 52

5-({(4-phenoxybutyl)[(1S)-1,2,3,4-tetrahydro-1-naphthalenyl]amino}carbonyl)-1,2,4-benzenetricarboxylic acid

EXAMPLE 52A 4-phenoxy-N-[(1S)-1,2,3,4-tetrahydro-1-naphthalenyl]butanamide

4-Phenoxybutanoic acid (1.05 g, 5.8 mmol, Lancaster) and triethylamine (2.4 mL, 17.4 mmol) in anhydrous CH$_2$Cl$_2$ (25 mL) were treated with pivaloyl chloride (0.75 mL, 6.1 mmol) at 0° C. After stirring for 1 hour, the reaction mixture was treated with (1S)-1,2,3,4-tetrahydro-1-naphthalenylamine (1.0 mL, 6.9 mmol) and the reaction mixture was allowed to warm to room temperature and stir for 16 hours. The reaction mixture was diluted with CH$_2$Cl$_2$, washed with 1N HCl, saturated NaHCO$_3$, brine, dried (Na$_2$SO$_4$), filtered and the filtrate concentrated under reduced pressure. The residue was purified by flash chromatography (silica gel, 40% ethyl acetate/hexanes) to provide the title compound as a colorless oil (2.07 g).

EXAMPLE 52B

N-(4-phenoxybutyl)-N-[(1S)-1,2,3,4-tetrahydro-1-naphthalenyl]amine

The product from Example 52A (2.07 g) in THF (20 mL) was treated with borane-tetrahydrofuran complex (12 mL, 12 mmol) and heated at reflux for 1.5 hours. The mixture was allowed to cool to room temperature and quenched with 1N NaOH. The mixture was stirred 30 for minutes and diluted with diethyl ether. The separated organic phase was washed with brine, dried (Na$_2$SO$_4$), filtered and the filtrate concentrated. The residue was purified by flash chromatography (silica gel, 30% ethyl acetate/hexanes) to provide the title compound as a pale brown oil (0.48 g, 28% yield).

$^1$H NMR (300 MHz, CDCl$_3$) δ6.75–7.55 (m, 9H), 3.8–4.05 (m, 3H), 2.65–2.9 (m, 4H), 1.6–2.1 (m, 9H); MS (DCI/NH$_3$) 296 (M+H)$^+$.

EXAMPLE 52C 5-({(4-phenoxybutyl)[(1S)-1,2,3,4-tetrahydro-1-naphthalenyl]amino}carbonyl)-12,4-benzenetricarboxylic acid The product from Example 52B and 1,2,4,5-benzenetetracarboxylic dianhydride were processed as described in Example 1B to provide the title compound.

$^1$H NMR (300 MHz, DMSO-d$_6$) δ13.7 (bs, 1H), 6.65–8.3 (m, 1H), 2.6–5.6 (m, (m, 7H), 1.2–2.2 (m, 8H); MS (ESI–) 530 (M–H)$^-$.

EXAMPLE 53

5-({(3-nitrobenzyl)[(1S)-1,2,3,4-tetrahydro-1-naphthalenyl]amino}carbonyl)-1,2,4-benzenetricarboxylic acid

EXAMPLE 53A

N-(3-nitrobenzyl)-N-[(1S)-1,2,3,4-tetrahydro-1-naphthalenyl]amine

3-Nitrobenzaldehyde and (1S)-1,2,3,4-tetrahydro-1-naphthalenylamine were processed as described in Example 1A to provide the title compound.

$^1$H NMR (300 MHz, CDCl$_3$) δ8.28–8.31 (m, 1H), 8.08–8.13 (m, 1H), 7.73–7.8 (m, 1H), 7.35–7.53 (m, 2H), 7.05–7.23 (m, 3H), 3.8–4.08 (m, 2H), 3.78–3.85 (m, 1H), 2.65–2.9 (m, 2H), 1.65–2.1 (m, 4H); MS (DCI/NH$_3$) 283 (M+H)$^+$.

EXAMPLE 53B 5-({(3-nitrobenzyl)[(1S)-1,2,3,4-tetrahydro-1-naphthalenyl]amino}carbonyl)-1,2,4-benzenetricarboxylic acid The product from Example 53A and 1,2,4,5-benzenetetracarboxylic dianhydride were processed as described in Example 1B to provide the title compound.

$^1$H NMR (300 MHz, DMSO-d$_6$) δ6.85–8.4 (m, 10H), 4.1–5.85 (m, 3H), 2.55–2.75 (m, 2H), 1.35–2.25 (m, 4H); MS (ESI–) 517 (M–H)$^-$.

EXAMPLE 54

5-({[3-(cyclohexyloxy)benzyl][(1S)-1,2,3,4-tetrahydro-1-naphthalenyl]amino}carbonyl)-1,2,4-benzenetricarboxylic acid

EXAMPLE 54A 3-(cyclohexyloxy)benzaldehyde

3-Hydroxybenzaldehyde, purchased from Acros, and cyclohexanol were processed under Mitsunobu conditions, as described in Saccomano, et al., J. Med. Chem. 34, (1991) 291–298, to provide the title compound.

EXAMPLE 54B

N-[3-(cyclohexyloxy)benzyl]-N-[(1S)-1,2,3,4-tetrahydro-1-naphthalenyl]amine

The product from Example 54A and (1S)-1,2,3,4-tetrahydro-1-naphthalenylamine were processed as described in Example 1A to provide the title compound.

$^1$H NMR (300 MHz, CDCl$_3$) δ6.7–7.4 (m, 8H+Ph$_3$PO), 4.1–4.23 (m, 1H), 3.77–3.95 (m, 3H), 2.65–2.9 (m, 2H), 1.35–2.1 (m, 15H); MS (DC/NH$_3$) 336 (M+H)$^+$.

EXAMPLE 54C 5-({[3-(cyclohexyloxy)benzyl][(1S)-1,2,3,4-tetrahydro-1-naphthalenyl]amino}carbonyl)-1,2,4-benzenetricarboxylic acid The product from Example 54B and 1,2,4,5-benzenetetracarboxylic dianhydride were processed as described in Example 1B to provide the title compound.

$^1$H NMR (300 MHz, DMSO-d$_6$) δ6.45–8.3 (m, 10H), 3.7–5.5 (m, 4H), 2.55–2.7 (m, 2H), 1.15–2.2 (m, 14H); MS (ESI+) 572 (M+H)$^+$.

EXAMPLE 55

5({{3-[exo-bicyclo[2.2.1]hept-2-yloxy]benzyl}[(1S)-1,2,3,4-tetrahydro-1-naphthalenyl]amino}carbonyl)-1,2,4-benzenetricarboxylic acid

EXAMPLE 55A 3-(exo-bicyclo[2.2.1]hept-2-yloxy)benzaldehyde

3-Hydroxybenzaldehyde, purchased from Acros, and endo-bicyclo[2.2.1]heptan-2-ol, purchased from Aldrich, were processed under Mitsunobu conditions, as described in Saccomano, et al., J. Med. Chem. 34, (1991) 291–298, to provide the title compound.

EXAMPLE 55B

N-[3-(exo-bicyclo[2.2.11]hept-2-yloxy)benzyl]-N-[(1S)-1,2,3,4-tetrahydro-1-naphthalenyl]amine The product from Example 55A and (1S)-1,2,3,4-tetrahydro-1-naphthalenylamine were processed as described in Example 1A to provide the title compound.

$^1$H NMR (300 MHz, CDCl$_3$) δ6.7–7.4 (m, 8H+Ph$_3$PO), 4.15–4.2 (m, 1H), 3.74–3.95 (m, 3H), 2.65–2.9 (m, 2H), 2.43–2.48 (m, 1H), 2.28–2.35 (m, 1H), 1.1–2.1 (m, 13H); MS (DCI/NH$_3$) 348 (M+H)$^+$.

EXAMPLE 55C 5-({{3-[exo-bicyclo[2.2.1]hept-2-yloxy]benzyl}[(1S)-1,2,3,4-tetrahydro-1-naphthalenyl]amino}carbonyl)-1,2,4-benzenetricarboxylic acid The product from Example 55B and 1,2,4,5-benzenetetracarboxylic dianhydride were processed as described in Example 1B to provide the title compound.

$^1$H NMR (300 MHz, DMSO-d$_6$) δ6.4–8.3 (m, 10H), 3.7–5.5 (m, 4H), 2.55–2.7 (m, 2H), 1.0–2.4 (m, 14H); MS (ESI+) 584 (M+H)$^+$.

EXAMPLE 56

5-({[spiro[1,3-benzodioxol-5-yl-2,1'-cyclohexane]methyl][(1S)-1,2,3,4-tetrahydro-1-naphthalenyl]amino}carbonyl)-1,2,4-benzenetricarboxylic acid

EXAMPLE 56A spiro[5-bromo-1,3-benzodioxole-2,1'-cyclohexane]

A vigorously stirred solution of spiro[1,3-benzodioxole-2,1'-cyclohexane] (2.49 g, 13.1 mmol), prepared according to Boeckmann, J. and Schill, G., Chem Ber. 110 (1977) 703, in CHCl$_3$ (100 mL) and saturated NaHCO$_3$ (100 mL) was treated with bromine (0.67 mL, 13.1 mmol) in CHCl$_3$ (10 mL) dropwise. After stirring for 3 hours, the organic phase was separated and washed with 10% Na$_2$S$_2$O$_5$ solution, water, brine, dried (Na$_2$SO$_4$), filtered and the filtrate concentrated under reduced pressure. The residue was purified by flash chromatography (silica gel, eluting with hexanes) to provide the title compound as a white solid (1.98 g).

EXAMPLE 56B spiro[5-formyl-1,3-benzodioxole-2,1'-cyclohexane]

The product from Example 56A (1.17 g, 4.35 mmol) in THF (40 mL) was treated with tert-butyllithium (5.80 mL of a 1.5 M solution in pentane, 8.70 mmol) dropwise at −78° C. After 15 minutes, the reaction mixture was treated with DMF (3.37 mL, 43.5 mmol) and stirred at −78° C. for 2 hours. The reaction mixture was diluted with diethyl ether and quenched with 1N HCl. The separated organic phase was washed with 1N NaOH, water, brine, dried (Na$_2$SO$_4$), filtered and the filtrate concentrated under reduced pressure. The residue was purified by flash chromatography (silica gel, 2% ethyl acetate/hexanes) to provide the title compound as a colorless oil (415 mg, 15% yield).

$^1$H NMR (300 MHz, CDCl$_3$) δ9.78 (s, 1H), 7.36 (dd, 1H), 7.23 (d, 1H), 6.84 (d, 1H), 1.9–1.97 (m, 4H), 1.7–1.8 (m, 4H), 1.47–1.57 (m, 2H); MS (DCI/NH$_3$) 219 (M+H)$^+$, 236 (M+NH$_4$)$^+$.

EXAMPLE 56C

N-[spiro[1,3-benzodioxol-5-yl-2,1'-cyclohexane]methyl]-N-[(1S)-1,2,3,4-tetrahydro-1-naphthalenyl]amine The product from Example 56B and (1S)-1,2,3,4-tetrahydro-1-naphthalenylamine were processed as described in Example 1A to provide the title compound.

$^1$H NMR (300 MHz, CDCl$_3$) δ6.65–7.42 (m, 7H), 3.7–3.88 (m, 3H), 2.65–2.9 (m, 2H), 1.4–2.1 (m, 15H); MS (DCI/NH$_3$) 350 (M+H)$^+$.

EXAMPLE 56D 5-({[spiro[1,3-benzodioxol-5-yl-2,1'-cyclohexanelmethyl][(1S)-1,2,3,4-tetrahydro-1-naphthalenyl]amino}carbonyl)-1,2,4-benzenetricarboxylic acid The product from Example 56C and 1,2,4,5-benzenetetracarboxylic dianhydride were processed as described in Example 11B to provide the title compound.

$^1$H NMR (300 MHz, DMSO-d$_6$) δ6.25–8.45 (m, 9H), 3.7–5.6 (m, 3H), 2.55–2.75 (m, 2H), 1.3–2.2 (m, 14H); MS (ESI+) 586 (M+H)$^+$.

EXAMPLE 57

5-({[3-(4-fluorophenoxy)benzyl][(1S)-1,2,3,4-tetrahydro-1-naphthalenyl]amino}carbonyl)-1,2,4-benzenetricarboxylic acid

EXAMPLE 57A

N-[3-(4-fluorophenoxy)benzyl]-N-[(1S)-1,2,3,4-tetrahydro-1-naphthalenyl]amine 3-(4-Fluorophenoxy)benzaldehyde, prepared as described in Tanaka, et al., J. Med. Chem., 41 (1998) 4408–4420, and (1S)-1,2,3,4-tetrahydro-1-naphthalenylamine were processed as described in Example 1A to provide the title compound.

$^1$H NMR (300 MHz, CDCl$_3$) δ6.8–7.35 (m, 12H), 3.75–3.95 (m, 3H), 2.65–2.9 (m, 2H), 1.4–2.1 (m, 5H); MS (DC/NH$_3$) 348 (M+H)$^+$.

EXAMPLE 57B 5-({[3-(4-fluorophenoxy)benzyl][(1S)-1,2,3,4-tetrahydro-1-naphthalenyl]amino}carbonyl)-1,2,4-benzenetricarboxylic acid The product from Example 57A and 1,2,4,5-benzenetetracarboxylic dianhydride were processed as described in Example 1B to provide the title compound.

$^1$H NMR (300 MHz, DMSO-d$_6$) δ6.5–8.45 (m, 14H), 3.7–5.6 (m, 3H), 2.55–2.75 (m, 2H), 1.3–2.15 (m, 4H); MS (ESI+) 584 (M+H)$^+$.

EXAMPLE 58

5-({[3-(allyloxy)benzyl][(1S)-1,2,3,4-tetrahydro-1-naphthalenyl]amino}carbonyl)-1,2,4-benzenetricarboxylic acid

EXAMPLE 58A 3-(allyloxy)benzaldehyde

3-Hydroxybenzaldehyde (1.00 g, 8.19 mmol) and allyl bromide (0.780 mL, 9.01 mmol) in N,N-dimethylacetamide (35 mL) was treated with Cs$_2$CO$_3$ (4.01 g, 12.3 mmol) and allowed to stir at room temperature for 12 hours. The reaction mixture was diluted with diethyl ether (150 mL), washed with 1N HCl, saturated NaHCO$_3$, brine, dried (MgSO$_4$), filtered and the filtrate concentrated. The residue was purified by flash chromatography (silica gel, using 7% ethyl acetate/hexanes as eluent) to provide the title compound as a clear oil (1.19 g, 89%).

$^1$H NMR (CDCl$_3$, 300 MHz) δ4.82 (m, 2H), 5.25–5.5.50 (m, 2H), 6.03 (m, 1H), 7.18–7.52 (m, 4H), 9.95 (s, 1H); MS (DCI+) 163 (M+H)$^+$.

EXAMPLE 58B

N-[3-(allyloxy)benzyl]-N-[(1S)-1,2,3,4-tetrahydro-1-naphthalenyl]amine

The product from Example 58A and (1S)-1,2,3,4-tetrahydro-1-naphthalenylamine were processed as described in Example 1A to provide the title compound.

$^1$H NMR (CDCl$_3$, 300 MHz) δ1.42–2.05 (m, 4H), 2.79 (m, 2H), 3.78–3.95 (m, 3H), 4.50 (d, 2H), 5.26 (m, 1H), 5.42 (m, 1H), 6.05 (m, 1H), 6.78–7.37 (m, 8H); MS (DCI+) 294 (M+H)$^+$.

EXAMPLE 58C 5-({[3-(allyloxy)benzyl][(1S)-1,2,3,4-tetrahydro-1-nanhthalenyl]amino}carbonyl)-1,2,4-benzenetricarboxylic acid The product from Example 58B and 1,2,4,5-benzenetetracarboxylic dianhydride were processed as described in Example 1B to provide the title compound.

$^1$H NMR (DMSO-d$_6$, 400 MHz) δ1.18–2.17 (m, 4H), 2.55–2.70 (m, 2H), 3.65–5.02 (m, 5H), 5.22–5.50 (m, 2H), 6.05 (m, 1H), 6.55–8.30 (m, 10H); HRMS (FAB) calculated for C$_{30}$H$_{28}$NO$_8$ 530.1815 (M+H)$^+$. Found 530.1811 (M+H)$^+$.

EXAMPLE 59

5-({[3-(2-cyclohexen-1-yloxy)benzyl][(1S)-1,2,3,4-tetrahydro-1-naphthalenyl]amino}carbonyl)-1,2,4-benzenetricarboxylic acid

EXAMPLE 59A 3-(2-cyclohexen-1-yloxy)benzaldehyde

3-Bromo-1-cyclohexene and 3-hydroxybenzaldehyde were processed as described in Example 58A to provide the title compound.

$^1$H NMR (CDCl$_3$, 300 MHz) δ1.62–2.20 (m, 6H), 4.87 (m, 1H), 5.91 (m, 1H), 6.02 (m 1H), 7.18–7.45 (m, 4H), 9.98 (s, 1H); MS (DCI+) 203 (M+H)$^+$.

EXAMPLE 59B

N-[3-(2-cyclohexen-1-yloxy)benzyl]-N-[(1S)-1,2,3,4-tetrahydro-1-naphthalenyl]amine The product from Example 59A and (1S)-1,2,3,4-tetrahydro-1-naphthalenylamine were processed as described in Example 1A to provide the title compound.

$^1$H NMR (CDCl$_3$, 300 MHz) δ1.41–2.22 (m, 10H), 2.65–2.91 (m, 2H), 3.78–3.95 (m, 3H), 4.80 (m, 1H), 5.86–6.02 (m, 2H), 6.78–7.42 (m, 8H); MS (DCI+) 334 (M+H)$^+$.

EXAMPLE 59C 5-({[3-(2-cyclohexen-1-yloxy)benzyl][(1S)-1,2,3,4-tetrahydro-1-naphthalenyl]amino}carbonyl)-1,2,4-benzenetricarboxylic acid The product from Example 59B and 1,2,4,5-benzenetetracarboxylic dianhydride were processed as described in Example 1B to provide the title compound.

$^1$H NMR (DMSO-d$_6$, 400 MHz) δ1.22–2.15 (m, 10H), 2.50–2.68 (m, 2H), 3.83–4.28 (m, 2H), 4.65–4.95 (m, 2H), 5.23–6.05 (m, 2H), 6.45–8.25 (m, 10H); HRMS (FAB): calculatedd for C$_{33}$H$_{32}$NO$_8$ 570.2128 (M+H)$^+$. Found 570.2123 (M+H)$^+$.

EXAMPLE 60

5-({[3,5-bis(trifluoromethyl)benzyl][(1S)-1,2,3,4-tetrahydro-1-naphthalenyl]amino}carbonyl)-1,2,4-benzenetricarboxylic acid

EXAMPLE 60A

N-[3,5-bis(trifluoromethyl)benzyl]-N-[(1S)-1,2,3,4-tetrahydro-1-naphthalenyl]amine 3,5-bis(Trifluoromethyl)benzaldehyde and (1S)-1,2,3,4-tetrahydro-1-naphthalenylamine were processed as described in Example 1A to provide the title compound.

$^1$H NMR (CDCl$_3$, 300 MHz) δ1.67–2.11 (m, 4H), 2.64–2.91 (m, 2H), 3.82 (t, 1H), 3.96–4.02 (m, 2H), 7.05–7.92 (m, 7H); MS (ESI+) 374 (M+H)$^+$.

EXAMPLE 60B 5-({[3,5-bis(trifluoromethyl)benzyl][(1S)-1,2,3,4-tetrahydro-1-naphthalenyl]amino}carbonyl)-1,2,4-benzenetricarboxylic acid The product from Example 60A and 1,2,4,5-benzenetetracarboxylic dianhydride were processed as described in Example 1B to provide the title compound.

$^1$H NMR (DMSO-d$_6$, 400 MHz) δ1.47–2.15 (m, 4H), 2.52–2.80 (m, 2H), 4.23–5.82 (m, 3H), 6.73–8.32 (m, 9H); HRMS (FAB): calculated for C$_{29}$H$_{22}$NO$_7$F$_6$ 610.1300 (M+H)$^+$. Found 610.1287 (M+H)$^+$.

EXAMPLE 61

5-({(1S)-1,2,3,4-tetrahydro-1-naphthalenyl[3-(trifluoromethyl)benzyl]amino}carbonyl)-1,2,4-benzenetricarboxylic acid

EXAMPLE 61A

N-[(1S)-1,2,3,4-tetrahydro-1-naphthalenyl]-N-[3-(trifluoromethyl)benzyl]amine 3-(Trifluoromethyl)benzaldehyde and (1S)-1,2,3,4-tetrahydro-1-naphthalenylamine were processed as described in Example 1A to provide the title compound.

$^1$H NMR (CDCl$_3$, 300 MHz) δ1.71–2.10 (m, 4H), 2.63–2.90 (m, 2H), 3.80–4.01 (m, 3H), 7.08–7.75 (m, 8H); MS (ESI+) 306 (M+H)$^+$.

EXAMPLE 61B 5-({(1S)-1,2,3,4-tetrahydro-1-naphthalenyl[3-(trifluoromethyl)benzyl]amino}carbonyl)-1,2,4-benzenetricarboxylic acid The product from Example 61A and 1,2,4,5-benzenetetracarboxylic dianhydride were processed as described in Example 1B to provide the title compound.

$^1$H NMR (DMSO-d$_6$, 400 MHz) δ1.40–2.15 (m, 4H), 2.55–2.65 (m, 2H), 4.05–5.68 (m, 3H), 6.95–8.38 (m, 10H); HRMS (FAB): calculated for C$_{28}$H$_{23}$NO$_7$F$_3$ 542.1427 (M+H)$^+$. Found 542.1439 (M+H)$^+$.

EXAMPLE 62

5-({(3,5-difluorobenzyl)[(1S)-1,2,3,4-tetrahydro-1-naphthalenyl]amino}carbonyl)-1,2,4-benzenetricarboxylic acid

EXAMPLE 62A

N-(3,5-difluorobenzyl)-N-[(1S)-1,2,3,4-tetrahydro-1-naphthalenyl]amine 3,5-Difluorobenzaldehyde and (1S)-1,2,3,4-tetrahydro-1-naphthalenylamine were processed as described in Example 1A to provide the title compound.

$^1$H NMR (CDCl$_3$, 300 MHz) δ1.72–2.25 (m, 4H), 2.72–2.93 (m, 2H), 3.80–4.01 (m, 3H), 6.63–7.44 (m, 7H); MS (ESI+) 274 (M+H)$^+$.

EXAMPLE 62B 5-({(3,5-difluorobenzyl)[(1S)-1,2,3,4-tetrahydro-1-naphthalenyl]amino}carbonyl)-1,2,4-benzenetricarboxylic acid The product from Example 62A and 1,2,4,5-benzenetetracarboxylic dianhydride were processed as described in Example 1B to provide the title compound.

$^1$NMR (DMSO-d$_6$, 400 MHz) δ1.45–2.08 (m, 4H), 2.53–2.80 (m, 2H), 3.88–5.65 (m, 3H), 6.75–8.33 (m, 9H); HRMS (FAB): calculated for C$_{27}$H$_{22}$NO$_7$F$_2$ 510.1364 (M+H)$^+$. Found 510.1368 (M+H)$^+$.

EXAMPLE 63

5-({[4-fluoro-3-(trifluoromethyl)benzyl][(1S)-1,2,3,4-tetrahydro-1-naphthalenyl]amino}carbonyl)-1,2,4-benzenetricarboxylic acid

EXAMPLE 63A

N-[4-fluoro-3-(trifluoromethyl)benzyl]-N-[(1S)-1,2,3,4-tetrahydro-1-naphthalenyl]amine 4-Fluoro-3-(trifluoromethyl)benzaldehyde and (1S)-1,2,3,4-tetrahydro-1-naphthalenylamine were processed as described in Example 1A to provide the title compound.

¹H NMR (CDCl₃, 300 MHz) δ1.65–2.11 (m, 4H), 2.71–2.92 (m, 2H), 3.82–3.98 (m, 3H), 7.11–7.75 (m, 7H); MS (ESI+) 324 (M+H)⁺.

EXAMPLE 63B 5-({[4-fluoro-3-(trifluoromethyl)benzyl][(1S)-1,23,4-tetrahydro-1-naphthalenyl]amino}carbonyl)-1,2,4-benzenetricarboxylic acid The product from Example 63A and 1,2,4,5-benzenetetracarboxylic dianhydride were processed as described in Example 1B to provide the title compound.

¹H NMR (DMSO-d₆, 400 MHz) δ1.42–2.15 (m, 4H), 2.55–2.80 (m, 2H), 4.08–5.75 (m, 3H), 6.87–8.42 (m, 9H); HRMS (FAB): calculated for $C_{28}H_{22}NO_7F_4$ 560.1332 (M+H)⁺. Found 560.1326 (M+H)⁺.

EXAMPLE 64

5-({(3,5-dibromobenzyl)[(1S)-1,2,3,4-tetrahydro-1-naphthalenyl]amino}carbonyl)-1,2,4-benzenetricarboxylic acid

EXAMPLE 64A

N-(3,5-dibromobenzyl)-N-[(1S)-1,2,3,4-tetrahydro-1-naphthalenyl]amine 3,5-Dibromobenzaldehyde and (1S)-1,2,3,4-tetrahydro-1-naphthalenylamine were processed as described in Example 1A to provide the title compound.

¹H NMR (CDCl₃, 300 MHz) δ1.70–2.07 (m, 4H), 2.66–2.95 (m, 2H), 3.79–3.94 (m, 3H), 7.02–7.62 (m, 7H); MS (ESI+) 396 (M+H)⁺.

EXAMPLE 64B 5-({(3,5-dibromobenzyl)[(1S)-1,2,3,4-tetrahydro-1-naphthalenyl]amino}carbonyl)-1,2,4-benzenetricarboxylic acid The product from Example 64A and 1,2,4,5-benzenetetracarboxylic dianhydride were processed as described in Example 1B to provide the title compound.

¹H NMR (DMSO-d₆, 400 MHz) δ1.40–2.18 (m, 4H), 2.53–2.80 (m, 2H), 3.93–5.68 (m, 3H), 6.87–8.32 (m, 9H); HRMS (FAB): calculated for $C_{27}H_{22}NO_7Br_2$ 629.9763 (M+H)⁺. Found 629.9766 (M+H)⁺.

EXAMPLE 65

5-({[3-fluoro-5-(trifluoromethyl)benzyl][(1S)-1,2,3,4-tetrahydro-1-naphthalenyl]amino}carbonyl)-1,2,4-benzenetricarboxylic acid

EXAMPLE 65A

N-[3-fluoro-5-(trifluoromethyl)benzyl]-N-[(1S)-1,2,3,4-tetrahydro-1-naphthalenyl]amine 3-Fluoro-5-(trifluoromethyl)benzaldehyde and (1S)-1,2,3,4-tetrahydro-1-naphthalenylamine were processed as described in Example 1A to provide the title compound.

¹H NMR (CDCl₃, 300 MHz) δ1.68–2.04 (m, 4H), 2.72–2.91 (m, 2H), 3.85 (t, 1H), 3.91–4.04 (m, 2H), 7.02–7.44 (m, 7H); MS (ESI+) 324 (M+H)⁺.

EXAMPLE 65B 5-({[3-fluoro-5-(trifluoromethyl)benzyl][(1S)-1,2,3,4-tetrahydro-1-naphthalenyl]amino}carbonyl)-1,2,4-benzenetricarboxylic acid The product from Example 65A and 1,2,4,5-benzenetetracarboxylic dianhydride were processed as described in Example 1B to provide the title compound.

¹H NMR (DMSO-d₆, 400 MHz) δ1.40–2.25 (m, 4H), 2.50–2.85 (m, 2H), 3.98–5.78 (m, 3H), 6.85–8.35 (m, 9H); HRMS (FAB): calculated for $C_{28}H_{22}NO_7F_4$ 560.1332 (M+H)⁺. Found 560.1326 (M+H)⁺.

EXAMPLE 66

5-({(3,5-dimethoxybenzyl)[(1S)-1,2,3,4-tetrahydro-1-naphthalenyl]amino}carbonyl)-1,2,4-benzenetricarboxylic acid

EXAMPLE 66A

N-(3,5-dimethoxybenzyl)-N-[(1S)-1,2,3,4-tetrahydro-1-naphthalenyl]amine 3,5-Dimethoxybenzaldehyde and (1S)-1,2,3,4-tetrahydro-1-naphthalenylamine were processed as described in Example 1A to provide the title compound.

¹H NMR (CDCl₃, 400 MHz) δ1.75 (m, 1H), 1.81–1.90 (m, 2H), 2.03 (m, 1H), 2.65–2.91 (m, 2H), 3.79–3.89 (m, 9H), 6.39 (t, 1H), 6.60 (m, 2H), 7.04–7.18 (m, 3H), 7.18 (m, 1H); MS (ESI+) 298 (M+H)⁺.

EXAMPLE 66B 5-({(3,5-dimethoxybenzyl)[(1S)-1,2,3,4-tetrahydro-1-naphthalenyl]amino}carbonyl)-1,2,4-benzenetricarboxylic acid The product from Example 66A and 1,2,4,5-benzenetetracarboxylic dianhydride were processed as described in Example 1B to provide the title compound.

¹H NMR (DMSO-d₆, 400 MHz) δ1.35–2.15 (m, 4H), 2.55–2.70 (m, 2H), 3.63–3.73 (m, 6H), 4.05–5.50 (m, 3H), 6.17–8.28 (m, 9H); HRMS (FAB): calculated for $C_{29}H_{28}NO_9$ 534.1764 (M+H)⁺. Found 534.1758 (M+H)⁺.

EXAMPLE 67

5-({(2,3-dichlorobenzyl)[(1S)-1,2,3,4-tetrahydro-1-naphthalenyl]amino}carbonyl)-1,2,4-benzenetricarboxylic acid

EXAMPLE 67A

N-(2,3-dichlorobenzyl)-N-[(1S)-1,2,3,4-tetrahydro-1-naphthalenyl]amine 2,3-Dichlorobenzaldehyde and (1S)-1,2,3,4-tetrahydro-1-naphthalenylamine were processed as described in Example 1A to provide the title compound.

¹H NMR (CDCl₃, 300 MHz) δ1.72–2.11 (m, 4H), 2.66–2.92 (m, 2H), 3.82 (t, 1H), 3.94–4.06 (m, 2H), 7.04–7.45 (m, 7H); MS (ESI+) 306 (M+H)⁺.

EXAMPLE 67B 5-({(2,3-dichlorobenzyl)[(1S)-1,2,3,4-tetrahydro-1-naphthalenyl]amino}carbonyl)-1,2,4-benzenetricarboxylic acid The product from Example 67A and 1,2,4,5-benzenetetracarboxylic dianhydride were processed as described in Example 1B to provide the title compound.

¹H NMR (DMSO-d₆, 400 MHz) δ1.45–2.25 (m, 4H), 2.51–2.70 (m, 2H), 3.95–5.77 (m, 3H), 7.05–8.32 (m, 9H); HRMS (FAB): calculated for $C_{27}H_{22}NO_7Cl_2$ 542.0773 (M+H)⁺. Found 542.0770 (M+H)⁺.

EXAMPLE 68

5-({(2,4-dichlorobenzyl)[(1S)-1,2,3,4-tetrahydro-1-naphthalenyl]amino}carbonyl)-1,2,4-benzenetricarboxylic acid

EXAMPLE 68A

N-(2,4-dichlorobenzyl)-N-[(1S)-1,2,3,4-tetrahydro-1-naphthalenyl]amine 2,4-Dichlorobenzaldehyde and (1S)-1,2,3,4-tetrahydro-1-naphthalenylamine were processed as described in Example 1A to provide the title compound.

$^1$H NMR (CDCl$_3$, 300 MHz) δ1.64–2.10 (m, 4H), 2.65–2.90 (m, 2H), 3.79 (t, 1H), 3.85–4.02 (m, 2H), 7.03–7.48 (m, 7H); MS (ESI+) 306 (M+H)$^+$.

EXAMPLE 68B 5-({(2,4-dichlorobenzyl)[(1S-1,2,3,4-tetrahydro-1-naphthalenyl]amino}carbonyl)-1,2,4-benzenetricarboxylic acid The product from Example 68A and 1,2,4,5-benzenetetracarboxylic dianhydride were processed as described in Example 1B to provide the title compound.

$^1$H NMR (DMSO-d$_6$, 400 MHz) δ1.40–2.25 (m, 4H), 2.53–2.70 (m, 2H), 3.95–5.75 (m, 3H), 7.05–8.32 (m, 9H); HRMS (FAB): calculated for C$_{27}$H$_{22}$NO$_7$Cl$_2$ 542.0773 (M+H)$^+$. Found 542.0767 (M+H)$^+$.

EXAMPLE 69

5-({(3,5-dimethylbenzyl)[(1S)-1,2,3,4-tetrahydro-1-naphthalenyl]amino}carbonyl)-1,2,4-benzenetricarboxylic acid

EXAMPLE 69A

N-(3,5-dimethylbenzyl)-N-[(1S)-1,2,3,4-tetrahydro-1-naphthalenyl]amine 3,5-Dimethylbenzaldehyde and (1S)-1,2,3,4-tetrahydro-1-naphthalenylamine were processed as described in Example 1A to provide the title compound.

$^1$H NMR (CDCl$_3$, 300 MHz) δ1.62–2.08 (m, 4H), 2.30 (s, 6H), 2.83–2.95 (m, 2H), 3.71–3.90 (m, 3H), 6.93–7.18 (m, 7H); MS (ESI+) 266 (M+H)$^+$.

EXAMPLE 69B 5-({(3,5-dimethylbenzyl)[(1S)-1,2,3,4-tetrahydro-1-naphthalenyl]amino}carbonyl)-1,2,4-benzenetricarboxylic acid The product from Example 69A and 1,2,4,5-benzenetetracarboxylic dianhydride were processed as described in Example 1B to provide the title compound.

$^1$H NMR (DMSO-d$_6$, 400 MHz) δ1.85–2.05 (m, 4H), 2.15–2.23 (m, 6H), 2.50–2.75 (m, 2H), 3.75–5.83 (m, 3H), 6.50–8.30 (m, 9H); HRMS (FAB): calculated for C$_{29}$H$_{28}$NO$_7$ 502.1866 (M+H)$^+$, Found 502.1874 (M+H)$^+$.

EXAMPLE 70

5-[((1S)-1,2,3,4-tetrahydro-1-naphthalenyl{3-[(trifluoromethyl)sulfanyl]benzyl}amino)carbonyl]-1,2,4-benzenetricarboxylic acid

EXAMPLE 70A

N-[(1S)-1,2,3,4-tetrahydro-1-naphthalenyl]-N-{3-[(trifluoromethyl)sulfanyl]benzyl}amine 3-[(Trifluoromethyl)sulfanyl]benzaldehyde and (1S)-1,2,3,4-tetrahydro-1-naphthalenylamine were processed as described in Example 1A to provide the title compound.

$^1$H NMR (CDCl$_3$, 300 MHz) δ1.65–2.04 (m, 4H), 2.63–2.90 (m, 2H), 3.80 (t, 1H), 3.84–4.02 (m, 2H), 7.03–7.78 (m, 8H); MS (ESI+) 338 (M+H)$^+$.

EXAMPLE 70B

5-[((1S)-1,2,3,4-tetrahydro-1-naphthalenyl{3-[(trifluoromethyl)sulfanyl]benzyl}amino)carbonyl]-1,2,4-benzenetricarboxylic acid The product from Example 70A and 1,2,4,5-benzenetetracarboxylic dianhydride were processed as described in Example 1B to provide the title compound.

$^1$H NMR (DMSO-d$_6$, 400 MHz) δ1.40–2.15 (m, 4H), 2.52–2.80 (m, 2H), 3.95–5.65 (m, 3H), 6.95–8.15 (m, 10H); HRMS (FAB): calculated for C$_{28}$H$_{23}$NO$_7$F$_3$S 574.1147 (M+H)$^+$. Found 574.1128 (M+H)$^+$.

EXAMPLE 71

5-({[3-(phenylsulfanyl)benzyl][(1S)-1,2,3,4-tetrahydro-1-naphthalenyl]amino}carbonyl)-1,2,4-benzenetricarboxylic acid

EXAMPLE 71A 3-(phenylsulfanyl)benzaldehyde 2-(3-Bromophenyl)-1,3-dioxolane (1.00 mL, 6.61 mmol) in THF (10 mL) was treated with 1.6M n-BuLi in hexanes (4.34 mL, 6.94 mmol) at −78° C. After stirring for 10 minutes, the mixture was treated with diphenyl disulfide (1.44 g, 6.61 mmol) and the reaction mixture was stirred overnight without replenishing the cooling bath. The reaction mixture was quenched with 20 mL of water and extracted with diethyl ether (3×50 mL.) The organic layers were combined, dried over MgSO$_4$, filtered and the filtrate concentrated. The crude oil was stirred in 25 mL of a 5:1 solution of CH$_3$CN/1N HCl overnight. The reaction mixture was diluted with 50 mL of brine and extracted with diethyl ether (3×50 mL.) The organic layers were combined, dried over MgSO$_4$, filtered and the filtrate concentrated to provide the title compound which was used without further purification.

EXAMPLE 71B

N-[3-(phenylsulfanyl)benzyl]-N-[(1S)-1,2,3,4-tetrahydro-1-naphthalenyl]amine

The product from Example 71A and (1S)-1,2,3,4-tetrahydro-1-naphthalenylamine were processed as described in Example 1A to provide the title compound as a clear oil. (1.06 g, 46%).

$^1$H NMR (CDCl$_3$, 300 MHz) δ1.75–2.04 (m, 4H), 2.61–2.83 (m, 2H), 3.72–3.97 (m, 3H), 7.02–7.41 (m, 13H); MS (ESI+) 346 (M+H)$^+$.

EXAMPLE 71C 5-({[3-(phenylsulfanyl)benzyl][(1S)-1,2,3,4-tetrahydro-1-naphthalenyl]amino}carbonyl)-1,2,4-benzenetricarboxylic acid The product from Example 71B and 1,2,4,5-benzenetetracarboxylic dianhydride were processed as described in Example 11B to provide the title compound.

$^1$H NMR (DMSO-d$_6$, 400 MHz) δ1.35–2.05 (m, 4H), 2.53–2.65 (m, 2H), 3.80–5.55 (m, 3H), 6.85–8.37 (m, 15H);

HRMS (FAB): calculated for $C_{33}H_{28}NO_7S$ 582.1586 (M+H)⁺. Found 582.1575 (M+H)⁺.

EXAMPLE 72

5-({{3-[(4-methoxyphenyl)sulfanyl]benzyl}[(1S)-1,2,3,4-tetrahydro-1-naphthalenyl]amino}carbonyl)-1,2,4-benzenetricarboxylic acid

EXAMPLE 72A

3-[(4-methoxyphenyl)sulfanyl]benzaldehyde 2-(3-Bromophenyl)-1,3-dioxolane and bis(4-methoxyphenyl) disulfide were processed as described in Example 71A to provide the title compound.

EXAMPLE 72B

N-{3-[(4-methoxyphenyl)sulfanyl]benzyl}-N-[(1S)-1,2,3,4-tetrahydro-1-naphthalenyl]amine The product from Example 72A and (1S)-1,2,3,4-tetrahydro-1-naphthalenylamine were processed as described in Example 1A to provide the title compound.

$^1$H NMR (CDCl$_3$, 300 MHz) δ1.62–2.04 (m, 4H), 2.62–2.84 (m, 6H), 6.90–7.43 (m, 12H); MS (ESI+) 376 (M+H)⁺.

EXAMPLE 72C 5-({{3-[(4-methoxyphenyl)sulfanyl]benzyl}[(1S)-1,2,3,4-tetrahydro-1-naphthalenyl]amino}carbonyl)-1,2,4-benzenetricarboxylic acid The product from Example 72B and 1,2,4,5-benzenetetracarboxylic dianhydride were processed as described in Example 1B to provide the title compound.

$^1$H NMR (DMSO-d$_6$, 400 MHz) δ1.40–2.03 (m, 4H), 2.43–2.65 (m, 2H), 3.86–5.52 (m, 6H), 6.71–8.31 (m, 14H); HRMS (FAB): calculated for $C_{34}H_{30}NO_8S$ 611.1614 (M+H)⁺. Found 611.1628. (M+H)⁺.

EXAMPLE 73

5-({{3-[(4-nitrophenyl)sulfanyl]benzyl}[(1S)-1,2,3,4-tetrahydro-1-naphthalenyl]amino}carbonyl)-1,2,4-benzenetricarboxylic acid

EXAMPLE 73A

3-[(4-nitrophenyl)sulfanyl]benzaldehyde 2-(3-Bromophenyl)-1,3-dioxolane and bis(4-nitrophenyl) disulfide were processed as described in Example 71A to provide the title compound.

EXAMPLE 73B

N-{3-[(4-nitrophenyl)sulfanyl]benzyl}-N-[(1S)-1,2,3,4-tetrahydro-1-naphthalenyl]amine The product from Example 73A and (1S)-1,2,3,4-tetrahydro-1-naphthalenylamine were processed as described in Example 1A to provide the title compound.

$^1$H NMR (CDCl$_3$, 300 MHz) δ1.62–2.02 (m, 4H), 2.82–2.91 (m, 2H), 3.81 (t, 1H), 3.84–4.00 (m, 2H), 7.06–8.09 (m, 12H); MS (ESI+) 391 (M+H)⁺.

EXAMPLE 73C 5-({{3-[(4-nitrophenyl)sulfanyl]benzyl}[(1S)-1,2,3,4-tetrahydro-1-naphthalenyl]amino}carbonyl)-1,2,4-benzenetricarboxylic acid The product from Example 73B and 1,2,4,5-benzenetetracarboxylic dianhydride were processed as described in Example 1B to provide the title compound.

$^1$H NMR (DMSO-d$_6$, 400 MHz) δ1.60–2.08 (m, 4H), 2.41–2.69 (m, 2H), 3.98–5.63 (m, 3H), 7.02–8.39 (m, 14H); HRMS (FAB): calculated for $C_{33}H_{27}N_2O_9S$ 627.1437 (M+H)⁺. Found 627.1451 (M+H)⁺.

EXAMPLE 74

5-({[3-(methylsulfanyl)benzyl][(1S)-1,2,3,4-tetrahydro-1-naphthalenyl]amino}carbonyl)-1,2,4-benzenetricarboxylic acid

EXAMPLE 74A 3-(methylsulfanyl)benzaldehyde 2-(3-Bromophenyl)-1,3-dioxolane and dimethyl disulfide were processed as described in Example 71A to provide the title compound.

EXAMPLE 74B

N-[3-(methylsulfanyl)benzyl]-N-[(1S)-1,2,3,4-tetrahydro-1-naphthalenyl]amine

The product from Example 74A and (1S)-1,2,3,4-tetrahydro-1-naphthalenylamine were processed as described in Example 1A to provide the title compound.

$^1$H NMR (CDCl$_3$, 300 MHz) δ1.61–2.04 (m, 4H), 2.45 (s, 3H), 2.65–2.82 (m, 2H), 3.79–3.97 (m, 2H), 7.02–7.39 (m, 8H); MS (ESI+) 284 (M+H)⁺.

EXAMPLE 74C 5-({[3-(methylsulfanyl)benzyl][(1S)-1,2,3,4-tetrahydro-1-naphthalenyl amino}carbonyl)-1,2,4-benzenetricarboxylic acid The product from Example 74B and 1,2,4,5-benzenetetracarboxylic dianhydride were processed as described in Example 1B to provide the title compound.

$^1$H NMR (DMSO-d$_6$, 400 MHz) δ1.45–2.09 (m, 4H), 2.50–2.68 (m, 2H), 3.87–5.50 (m, 3H), 6.81–8.27 (m, 10H); HRMS (FAB): calculated for $C_{28}H_{26}NO_7S$ 520.1430 (M+H)⁺. Found 5420.1409 (M+H)⁺.

EXAMPLE 75

5-({{3-[(4-chlorophenyl)sulfanyl]benzyl}[(1S)-1,2,3,4-tetrahydro-1-naphthalenyl]amino}carbonyl)-1,2,4-benzenetricarboxylic acid

EXAMPLE 75A

3-[(4-chlorophenyl)sulfanyl]benzaldehyde 2-(3-Bromophenyl)-1,3-dioxolane and bis(4-chlorophenyl) disulfide were processed as described in Example 71A to provide the title compound.

EXAMPLE 75B

N-{3-[(4-chlorophenyl)sulfanyl]benzyl}-N-[(1S)-1,2,3,4-tetrahydro-1-naphthalenyl]amine The product from Example 75A and (1S)-1,2,3,4-tetrahydro-1-naphthalenylamine were processed as described in Example 1A to provide the title compound.

$^1$H NMR (CDCl$_3$, 300 MHz) δ1.65–2.07 (m, 4H), 2.69–2.83 (m, 2H), 3.75–3.96 (m, 3H), 7.02–7.41 (m, 12H); MS (ESI+) 380 (M+H)⁺.

EXAMPLE 75C 5-({{3-[(4-chlorophenyl)sulfanyl]benzyl}[(1S)-1,2,
3,4-tetrahydro-1-naphthalenyl]amino}carbonyl)-1,2,
4-benzenetricarboxylic acid The product from Example 75B and 1,2,4,5-benzenetetracarboxylic dianhydride were processed as described in Example 1B to provide the title compound.

$^1$H NMR (DMSO-d$_6$, 400 MHz) δ1.42–1.99 (m, 4H), 2.50–2.64 (m, 2H), 3.90–5.53 (m, 3H), 6.91–8.28 (m, 14H); HRMS (FAB): calculated for $C_{33}H_{27}NO_7ClS$ 616.1197 (M+H)$^+$. Found 616.1181 (M+H)$^+$.

EXAMPLE 76

5-({{3-[(methoxyimino)methyl]benzyl}[(1S)-1,2,3,
4-tetrahydro-1-naphthalenyl]amino}carbonyl)-1,2,4-
benzenetricarboxylic acid

EXAMPLE 76A methyl 3-formylbenzoate

3-Formylbenzoic acid (3.11 g, 20.7 mmol, Aldrich) in 10:1 methanol:water (110 mL) was treated with $Cs_2CO_3$ (3.11 g, 10.4 mmol). After stirring 18 hours, the solvent was evaporated under reduced pressure and the residue was dried under reduced pressure at 60° C. The residue was suspended in DMF (40 mL) and treated with iodomethane (2.58 mL, 41.4 mmol). After stirring at ambient temperature 2 hours, the mixture was poured into water and extracted with diethyl ether. The ether extracts were combined, washed with water, saturated NaHCO$_3$, dried (MgSO$_4$), filtered and the filtrate concentrated under reduced pressure to provide the title compound as a white solid (2.81 g).

$^1$H NMR (300 MHz, CDCl$_3$) δ10.09 (s, 1H), 8.52–8.55 (m, 1H), 8.28–8.33 (m, 1H), 8.05–8.12 (m, 1H), 7.6–7.67 (m, 1H), 3.98 (s, 3H); MS (DCI/NH$_3$) 182 (M+NH$_4$)$^+$.

EXAMPLE 76B methyl 3-{[(1S)-1,2,3,4-tetrahydro-1-
naphthalenylamino]methyl}benzoate The product from Example 76A (2.80 g, 17.1 mmol) in methanol (75 mL) was treated with (1S)-1,2,3,4-tetrahydro-1-naphthalenylamine (2.45 mL, 17.1 mmol, Lancaster). After stirring for 18 hours, the mixture was treated with sodium borohydride and the mixture was allowed to stir an additional 4 hours. The volatiles were evaporated under reduced pressure and the residue was dissolved in diethyl ether and quenched with 1N NaOH solution. The separated organic phase was washed with water, brine, dried (Na$_2$SO$_4$), filtered and the filtrate concentrated under reduced pressure to provide the title compound as a colorless oil (4.99 g).

$^1$H NMR (300 MHz, CDCl$_3$) δ8.05–8.08 (m, 1H), 7.9–7.95 (m, 1H), 7.6–7.6 (m, 1H), 7.3–7.45 (m, 2H), 7.05–7.2 (m, 3H), 3.78–4.03 (m, 6H), 2.65–2.9 (m, 2H), 1.65–2.1 (m, 4H); MS (DCI/NH$_3$) 296 (M+H)$^+$.

EXAMPLE 76C (3-{[(1S)-1,2,3,4-tetrahydro-1-naphthalenylamino]
methyl}phenyl)methanol The product from Example 76B (4.99 g, 16.9 mmol) in anhydrous THF (100 mL) was treated with lithium aluminum hydride (16.9 mL, 16.9 mmol, 1M solution in THF) and heated at reflux for 1.5 hours. The reaction mixture was cooled to 0° C. and quenched by careful addition of Na$_2$SO$_4$·10H$_2$O. The mixture was stirred for 30 minutes and then treated with MgSO$_4$, filtered through celite and the filtrate was concentrated under reduced pressure to provide the title compound as a colorless oil (4.23 g).

$^1$H NMR (300 MHz, CDCl$_3$) δ7.05–7.45 (m, 8H), 4.7 (s, 2H), 3.68–4.0 (m, 3H), 2.65–2.9 (m, 2H), 1.4–2.1 (m, 6H); MS (DCI/NH$_3$) 268 (M+H)$^+$.

EXAMPLE 76D 5-({[3-(hydroxymethyl)benzyl][(1S)-1,2,3,4-
tetrahydro-1-naphthalenyl]amino}carbonyl)-1,2,4-
benzenetricarboxylic acid The product from Example 76C (1.27 g, 4.75 mmol) and diisopropylethylamine (2.41 mL, 14.2 mmol) in anhydrous THF (40 mL) was treated with 1,2,4,5-benzenetetracarboxylic dianhydride (3.11 g, 14.2 mmol) in one portion at −78° C. The mixture was allowed to gradually warm to room temperature over 16 hours. The mixture was treated with 1M LiOH solution (40 mL) and stirred vigorously 24 hours. The mixture was acidified and extracted with ethyl acetate. The organic extracts were combined, washed with 1N HCl, brine, dried (Na$_2$SO$_4$), filtered and the filtrate concentrated under reduced pressure. The residue was purified by flash chromatography (silica gel, 100:1:1 ethyl acetate:formic acid:water) to provide the title compound as a white solid (2.31 g).

EXAMPLE 76E 5-({(3-formylbenzyl)[(1S)-1,2,3,4-tetrahydro-1-
naphthalenyl]amino}carbonyl)-1,2,4-
benzenetricarboxylic acid The product from Example 76D (2.3 g, 4.6 mmol) and triethylamine (4.48 mL, 32.1 mmol) in DMSO (25 mL) was treated with sulfur trioxide pyridine complex (2.92 g, 18.4 mmol). After 5 hours, the mixture was partitioned between ethyl acetate and 1N HCl. The separated organic phase was washed with 1N HCl, brine, and concentrated under reduced pressure. The residue was dissolved in THF (30 mL) and saturated aqueous Na$_2$CO$_3$ solution (30 mL) was added. After stirring vigorously for 1 hour, the separated aqueous layer was acidified and extracted with ethyl acetate. The organic extracts were combined, washed with brine, dried (Na$_2$SO$_4$), filtered and the filtrate concentrated under reduced pressure to provide the title compound as a pale yellow solid (1.73 g).

EXAMPLE 76F 5-({{3-[(methoxyimino)methyl]benzyl}[(1S)-1,2,3,
4-tetrahydro-1-naphthalenyl]amino}carbonyl)-1,2,4-
benzenetricarboxylic acid The product from Example 76E (132 mg, 0.26 mmol) in pyridine (5 mL) was treated with O-methylhydroxylamine hydrochloride (26 mg, 0.32 mmol). After stirring for 1 hour at room temperature, the volatiles were evaporated under reduced pressure. The residue was dissolved in ethyl acetate and washed with 1N HCl, water, brine, dried (Na$_2$SO$_4$), filtered and the filtrate concentrated under reduced pressure. The residue was purified by flash chromatography (silica gel, 100:1:1 ethyl acetate:formic acid:water) to provide the title compound as a white solid (43 mg, 31%).

¹H NMR (300 MHz, DMSO-d₆) δ7.0–8.35 (m, 11H), 3.8–5.6 (m, 6H), 2.55–2.75 (m, 2H), 1.3–2.1 (4H); MS (ESI–) 529 (M–H)⁻.

EXAMPLE 77

5-({{3-[(E)-(tert-butoxyimino)methyl]benzyl}[(1S)-1,2,3,4-tetrahydro-1-naphthalenyl]amino}carbonyl)-1,2,4-benzenetricarboxylic acid The product from Example 76E and O-(tert-butyl) hydroxylamine were processed as described in Example 76F to provide the title compound.

¹H NMR (300 MHz, DMSO-d₆) δ7.0–8.3 (m, 1H), 3.85–5.6 (m, 3H), 2.55–2.7 (m, 2H), 1.35–2.1 (4H), 1.3 (s, 9H); MS (ESI+) 573 (M+H)⁺.

EXAMPLE 78

5-({{3-[(isopropoxyimino)methyl]benzyl}[(1S)-1,2,3,4-tetrahydro-1-naphthalenyl]amino}carbonyl)-1,2,4-benzenetricarboxylic acid The product from Example 76E and O-isopropylhydroxylamine were processed as described in Example 76F to provide the title compound.

¹H NMR (300 MHz, DMSO-d₆) δ7.0–8.3 (m, 11H), 3.8–5.6 (m, 5H), 2.55–2.7 (m, 2H), 1.3–2.15 (m, 5H), 0.92, (d, 6H); MS (ESI+) 573 (M+H)⁺.

EXAMPLE 79

5-{[(1S)-1,2,3,4-tetrahydro-1-naphthalenyl(3-{[(tetrahydro-2H-pyran-2-yloxy)imino]methyl}benzyl)amino]carbonyl}-1,2,4-benzenetricarboxylic acid The product from Example 76E and O-tetrahydro-2H-pyran-2-ylhydroxylamine were processed as described in Example 76F to provide the title compound.

¹H NMR (300 MHz, DMSO-d₆) δ7.0–8.35 (m, 11H), 3.4–5.6 (m, 6H), 2.55–2.75 (m, 2H), 1.3–2.1 (m, 10H); MS (ESI–) 599 (M–H)⁻.

EXAMPLE 80

5-({{3-[(phenoxyimino)methyl]benzyl}[(1S)-1,2,3,4-tetrahydro-1-napphthalenyl]amino}carbonyl)-1,2,4-benzenetricarboxylic acid The product from Example 76E and O-phenylhydroxylamine were processed as described in Example 76F to provide the title compound.

¹H NMR (300 MHz, DMSO-d₆) δ7.0–8.7 (m, 16H), 3.9–5.7 (m, 3H), 2.55–2.75 (m, 2H), 1.35–2.15 (m, 4H); MS (ESI–) 591 (M–H)⁻.

EXAMPLE 81

5-({(3-{[(benzyloxy)imino]methyl}benzyl)[(1S)-1,2,3,4-tetrahydro-1-naphthalenyl]amino}carbonyl)-1,2,4-benzenetricarboxylic acid The product from Example 76E and O-benzylhydroxylamine were processed as described in Example 76F to provide the title compound.

¹H NMR (300 MHz, DMSO-d₆) δ7.0–8.3 (m, 16H), 3.85–5.6 (m, 5H), 2.55–2.75 (m, 2H), 1.3–2.15 (m, 4H); MS (ESI–) 605 (M–H)⁻.

EXAMPLE 82

5-({[3-({[(4-nitrobenzyl)oxy]imino}methyl)benzyl][(1S)-1,2,3,4-tetrahydro-1-naphthalenyl]amino}carbonyl)-1,2,4-benzenetricarboxylic acid The product from Example 76E and O-(4-nitrobenzyl)hydroxylamine were processed as described in Example 76F to provide the title compound.

¹H NMR (300 MHz, DMSO-d₆) δ7.0–8.4 (m, 15H), 3.85–5.6 (m, 5H), 2.5–2.7 (m, 2H), 1.3–2.1 (m, 4H); MS (ESI–) 650 (M–H)⁻.

EXAMPLE 83

5-({[3-({[(2,3,4,5,6-pentafluorobenzyl)oxy]imino}methyl)benzyl][(1S)-1,2,3,4-tetrahydro-1-naphthalenyl]amino}carbonyl)-1,2,4-benzenetricarboxylic acid The product from Example 76E and O-(2,3,4,5,6-pentafluorobenzyl)hydroxylamine were processed as described in Example 76F to provide the title compound.

¹H NMR (300 MHz, DMSO-d₆) δ7.0–8.3 (m, 11H), 3.8–5.7 (m, 5H), 2.5–2.7 (m, 2H), 1.35–2.2 (m, 4H); MS (ESI+) 697 (M+H)⁺.

EXAMPLE 84

5-({{[5-(ethoxycarbonyl)-2-thienyl]methyl}[(1S)-1,2,3,4-tetrahydro-1-naphthalenyl]amino}carbonyl)-1,2,4-benzenetricarboxylic acid

EXAMPLE 84A methyl 5-formyl-2-thiophenecarboxylate

5-Formyl-2-thiophenecarboxylic acid, purchased from Lancaster, was processed as described in Example 76A to provide the title compound.

EXAMPLE 84B ethyl 5-{[(1S)-1,2,3,4-tetrahydro-1-naphthalenylamino]methyl}-2-thiophenecarboxylate The product from Example 84A in ethanol and (1S)-1,2,3,4-tetrahydro-1-naphthalenylamine were processed as described in Example 76B to provide the title compound.

¹H NMR (DMSO-d₆) δ7.65 (d,1H); 7.45 (m, 1H); 7.15 (m, 2H); 7.05 (m, 2H); 4.25 (q, 2H); 4.0 (d, 2H); 3.7 (m, 1H); 2.55–2.8 (m, 2H); 1.55–2.0 (m, 4H); 1.28 (t, 3H); MS (ESI+) 316 (M+H)⁺.

EXAMPLE 84C 5-({{[5-(ethoxycarbonyl)-2-thienyl]methyl}[(1S)-1,2,3,4-tetrahydro-1-naphthalenyl]amino}carbonyl)-1,2,4-benzenetricarboxylic acid The product from Example 84B and 1,2,4,5-benzenetetracarboxylic dianhydride were processed as described in Example 1B to provide the title compound.

¹H NMR (DMSO-d₆) δ6.99–8.3 (m, 8H); 4.25 (q, 2H); 4.1–4.99 (m, 3H); 2.6–2.8 (m, 2H); 1.7–1.85 (m, 2H); 1.4–1.55 (m, 2H); 1.3 (t, 3H); MS (ESI–) 550 (M–H)—, (ESI+) 552 (M+H)⁺.

EXAMPLE 85

5-({[(5'-fluoro-2'-methoxy[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol), 5-fluoro-2-methoxyphenylboronic acid (68 mg, 0.4 mmol)

and tetrakis(triphenylphosphine)palladium(0) (17 mg, 0.015 mmol) in THF (10 ml) were treated with 3M aqueous sodium carbonate (0.4 mL) and heated at reflux for 16 hours. After cooling to room temperature, the reaction mixture was diluted with water, acidified with 1N hydrochloric acid and extracted with diethyl ether. The organic layers were combined, dried with magnesium sulfate, filtered and the filtrate concentrated. The residue was purified by a Prep Nova Pak (HRC18) column using 0.1% trifluoroacetic acid:acetonitrile (10:90 to 95:5) as eluant to provide the title compound (50 mg).

$^1$H NMR (DMSO-d$_6$) δ8.27–6.96 (m, 13H), 5.00–3.82 (m, 3H), 3.75, 3.70 (2 s, 3H), 2.74–2.53 (m, 2H), 2.20–1.39 (m, 4H); MS (ESI+) 598 (M+H)$^+$.

EXAMPLE 86

5-({[(5'-chloro-2'-methoxy[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 5-chloro-2-methoxyphenylboronic acid were processed as described in Example 85 to provide the title compound.

$^1$H NMR (DMSO-d$_6$) 8.28–7.03 (m, 13H), 5.00–3.80 (m, 3H), 3.76 and 3.50 (2s, 3H), 2.75–2.55 (m, 2H), 2.10–1.33 (m, 4H); MS (ESI+) 614 (M+H)$^+$.

EXAMPLE 87

5-({[(3',5'-dichloro[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 3,5-dichlorophenylboronic acid were processed as described in Example 85 to provide the title compound.

$^1$H NMR (DMSO-d$_6$) δ8.28–7.03 (m, 13H), 5.10–3.80 (m, 3H), 2.75–2.55 (m, 2H), 2.05–1.33 (m, 4H); MS (ESI+) 618 (M+H)$^+$.

EXAMPLE 88

5-({[(2'-methoxy[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 2-methoxyphenylboronic acid were processed as described in Example 85 to provide the title compound.

$^1$H NMR (DMSO-d$_6$) δ8.28–6.95 (m, 14H), 5.04–3.80 (m, 3H), 3.76 and 3.72 (2s, 3H), 2.70–2.55 (m, 2H), 2.20–1.35 (m, 4H); MS (ESI+) 580 (M+H)$^+$.

EXAMPLE 89

5-({[(2'-chloro[1,1'-biphenyl]-3-yl)methyl][(1S)-1,2,3,4-tetrahydro-1-naphthalenyl]amino]carbonyl)-1,2,4-benzenetricarboxylic acid The product from Example 15B (165 mg, 0.3 mmol) and 2-chlorophenylboronic acid were processed as described in Example 85 to provide the title compound.

$^1$H NMR (DMSO-d$_6$) 8.28–7.00 (m, 14H), 5.04–3.90 (m, 3H), 2.76–2.55 (m, 2H), 2.20–1.35 (m, 4H); MS (ESI+) 584 (M+H)$^+$.

EXAMPLE 90

5-([(2',5'-dimethoxy[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 2,5-dimethoxyphenylboronic acid were processed as described in Example 85 to provide the title compound.

$^1$H NMR (DMSO-d$_6$) δ8.28–6.75 (m, 13H), 5.00–3.80 (m, 3H), 3.72, 3.68 and 3.63 (3s, 6H), 2.70–2.55 (m, 2H), 2.10–1.40 (m, 4H); MS (ESI+) 610 (M+H)$^+$.

EXAMPLE 91

5-{[(3'-chloro[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 3-chlorophenylboronic acid were processed as described in Example 85 to provide the title compound.

$^1$H NMR (DMSO-d$_6$) δ8.65–7.00 (m, 14H), 5.00–4.90 (m, 1H), 4.78–4.67 (m, 1H), 4.00–3.80 (m, 1H), 2.65–2.37 (m, 2H), 2.00–1.40 (m, 4H); MS (ESI+) 584 (M+H)$^+$.

EXAMPLE 92

5-({[(3',4'-dichloro[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 3,4-dichlorophenylboronic acid were processed as described in Example 85 to provide the title compound.

$^1$H NMR (DMSO-d$_6$) δ8.70–7.00 (m, 13H), 5.02–4.66 (m, 2H), 3.94–3.88 (m, 1H), 2.64–2.38 (m, 2H), 2.00–1.35 (m, 4H); MS (ESI+) 618 (M+H)$^+$.

EXAMPLE 93

5-({[(3'-chloro-4'-fluoro[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 3-chloro-4-fluorophenylboronic acid were processed as described in Example 85 to provide the title compound.

$^1$H NMR (DMSO-d$_6$) δ8.71–6.99 (m, 13H), 5.04–4.67 (m, 2H), 3.82–3.93 (m, 1H), 2.62–2.36 (m, 2H), 2.05–1.22 (m, 4H); MS (ESI+) 602 (M+H)$^+$.

EXAMPLE 94

5-({[3'-nitro[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 3-nitrophenylboronic acid were processed as described in Example 85 to provide the title compound.

$^1$H NMR (DMSO-d$_6$) δ8.75–7.00 (m, 14H), 5.05–4.85 (m, 1H), 4.70–4.80 (m, 1H), 3.90–4.00 (m, 1H), 2.70–2.34 (m, 2H), 2.10–1.20 (m, 4H); MS (ESI+) 595 (M+H)$^+$.

EXAMPLE 95

5-({[(3'-methoxy[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 3-methoxyphenylboronic acid were processed as described in Example 85 to provide the title compound.

$^1$H NMR (DMSO-d$_6$) δ8.70–6.85 (m, 14H), 5.00–4.92 (t, 1H), 4.66–4.80 (m, 1H), 4.00–3.70 (m, 4H), 2.69–2.40 (m, 2H), 2.04–1.23. (m, 4H); MS (ESI+)580 (M+H)$^+$.

EXAMPLE 96

5-({(1S)-1,2,3,4-tetrahydro-1-naphthalenyl[3-(3-thienyl)benzyl]amino}carbonyl)-1,2,4-benzenetricarboxylic acid The product from Example 15B (165 mg, 0.3 mmol) and 3-(3-thienyl)phenylboronic acid were processed as described in Example 85 to provide the title compound.

$^1$H NMR (DMSO-d$_6$) δ8.32–6.95 (m, 13H), 5.55–4.60 (m, 2H), 4.41–4.22 (m, 1H), 2.70–2.50 (m, 2H), 2.18–1.39 (m, 4H); MS (ESI+) 556 (M+H)$^+$.

EXAMPLE 97

5-({[(4'-chloro[1,1'-biphenyl]-3-yl)methyl][(1S)-1,2,3,4-tetrahydro-1-naphthalenyl]amino}carbonyl)-1,2,4-benzenetricarboxylic acid The product from Example 15B (165 mg, 0.3 mmol) and 4-chlorophenylboronic acid were processed as described in Example 85 to provide the title compound.

$^1$H NMR (DMSO-d$_6$) δ8.34–6.99 (m, 14H)5.62–4.60 (m, 2H), 4.33 (dd, 1H), 4.00 (br s, 3H), 2.75–2.50 (m, 2H), 2.20–1.12 (m, 4H); MS (ESI+) 584 (M+H)$^+$.

EXAMPLE 98

5-({(1S)-1,2,3,4-tetrahydro-1-naphthalenyl[3-(2-thienyl)benzyl]amino}carbonyl)-1,2,4-benzenetricarboxylic acid The product from Example 15B (165 mg, 0.3 mmol) and 3-(2-thienyl)phenylboronic acid were processed as described in Example 85 to provide the title compound.

$^1$H NMR (DMSO-d$_6$) δ8.29–6.96 (m, 13H), 5.57–4.62 (m, 2H), 4.40–3.93 (m, 1H), 2.74–2.55 (m, 2H), 2.20–1.40 (m, 4H); MS (ESI+) 556 (M+H)$^+$.

EXAMPLE 99

5-({(1S)-1,2,3,4-tetrahydro-1-naphthalenyl[(3',4',5'-trimethoxy[1,1'-biphenyl]-3-yl)methyl]amino}carbonyl)-1,2,4-benzenetricarboxylic acid The product from Example 15B (165 mg, 0.3 mmol) and 3,4,5-trimethoxyphenylboronic acid were processed as described in Example 85 to provide the title compound.

$^1$H NMR (DMSO-d$_6$) δ8.27–6.73 (m, 12H), 5.61–4.62 (m, 2H), 4.40–3.95 (m, 1H), 3.85 (s, 6H), 3.68 (s, 3H), 2.75–2.57 (m, 2H), 2.22–1.40 (m, 4H); MS (ESI+) 640 (M+H)$^+$.

EXAMPLE 100

2-1(methylamino)carbonyl]-5-({(3-phenoxybenzyl)[(1S)-1,2,3,4-tetrahydro-1-naphthalenyl]amino}carbonyl)terephthalic acid and 4-[(methylamino)carbonyl]-6-({(3-phenoxybenzyl)[(1S)-1,2,3,4-tetrahydro-1-naphthalenyl]amino}carbonyl)isophthalic Acid 1,2,4,5-Benzenetetracarboxylic dianhydride (1.1 g, 5 mmol) in THF (25 mL) was treated with diisopropylethyl amine (1.6 mL, 9.2 mmol) dropwise at −78° C. and then treated with N-(3-phenoxybenzyl)-N-[(1S)-1,2,3,4-tetrahydro-1-naphthalenyl]amine (9 mL, 4.5 mmol, 0.5M solution in ClCH$_2$CH$_2$Cl) dropwise. After allowing the reaction mixture to gradually warm to room temperature overnight, the mixture was recooled to −78° C. and treated with methylamine (2.5 mL, 5 mmol, 2M in MeOH) dropwise. The reaction mixture was again allowed to slowly warm to room temperature. The organics were removed under reduced pressure and the residue was dissolved in ethyl acetate (25 mL). The ethyl acetate solution was washed with 1N HCl (2×5 mL), brine (5 mL), dried over Na$_2$SO$_4$, filtered and the filtrate concentrated under reduced pressure. The residue was purified by flash chromatographed (silica gel, 5:95 MeOH:CH$_2$Cl$_2$ to 1:9 MeOH:CH$_2$Cl$_2$) to provide a solid. The solid was further purified by RP-HPLC to provide the title compound as an off-white solid (319 mg, 12%).

$^1$H NMR (300 MHz, DMSO-d$_6$) δ8.34, 8.15, 7.95, and 7.89 (4 s, 2H); 6.66–7.73 (m, 13H); 4.91 and 5.58 (2 m, 1H); 3.91 and 4.68 (2 m, 2H); 3.80 and 4.13 (2 br d, 3H); 2.59 (m, 2H); 1.39–2.06 (m, 4H); HRMS (FAB) calculated for C$_{34}$H$_{31}$N$_2$O$_7$ 579.2131 (M+H)$^+$. Found: 579.2159 (M+H)$^+$.

EXAMPLE 101

2-[(cyanoamino)carbonyl]-5-({(3-phenoxybenzyl)[(1S)-1,2,3,4-tetrahydro-1-naphthalenyl]amino}carbonyl)terephthalic acid and 4-[(cyanoamino)carbonyl]-6-({(3-phenoxybenzyl)[(1S)-1,2,3,4-tetrahydro-1-naphthalenyl]amino}carbonyl)isophthalic acid 1,2,4,5-Benzenetetracarboxylic dianhydride (1 mmol), diisopropylethyl amine, N-(3-phenoxybenzyl)-N-[(1S)-1,2,3,4-tetrahydro-1-naphthalenyl]amine and cyanamide were processed as described in Example 100 to provide the title compounds as a white solid (52 mg, 9% yield).

$^1$H NMR (500 MHz, d$_6$-DMSO) δ8.16 and 8.25 (2 s, 2H); 6.92–7.59 (m, 13H); 4.67 and 5.53 (2 br t, 1H); 4.19 and 4.82 (2 m, 2H); 2.62 (m, 2H); 1.34–2.09 (m, 4H); MS (ESI−) (M−H) 588.

EXAMPLE 102

2-(aminocarbonyl)-5-({(3-phenoxybenzyl)[(1S)-1,2,3,4-tetrahydro-1-naphthalenyl]amino}carbonyl)terephthalic acid and 4-(aminocarbonyl)-6-({(3-phenoxybenzyl)[(1S)-1,2,3,4-tetrahydro-1-naphthalenyl]amino}carbonyl)isophthalic acid 1,2,4,5-Benzenetetracarboxylic dianhydride (1 mmol), diisopropylethyl amine, N-(3-phenoxybenzyl)-N-[(1S)-1,2,3,4-tetrahydro-1-naphthalenyl]amine and ammonium hydroxide were processed as described in Example 100 to provide the title compounds as a white solid (120 mg, 21% yield).

$^1$H NMR (500 MHz, d$_6$-DMSO) δ8.31, 8.22, 8.01, and 7.95 (4 s, 2H); 6.69–7.66 (m, 13H); 4.66 and 5.49 (2 m, 1H); 4.27 and 4.83 (2 m, 2H); 2.62 (m, 2H); 1.37–2.13 (m, 4H); HRMS (FAB) calculated for C$_{33}$H$_{29}$N$_2$O$_7$ 565.1975 (M+H)$^+$. Found: 565.1973 (M+H)$^+$.

EXAMPLE 103

2-(methoxycarbonyl)-5-({(3-phenoxybenzyl)[(1S)-1,2,3,4-tetrahydro-1-naphthalenyl]amino}carbonyl)terephthalic acid and 4-(methoxycarbonyl)-6-({(3-phenoxybenzyl)[(1S)-1,2,3,4-tetrahydro-1-naphthalenyl]amino}carbonyl)isophthalic acid 1,2,4,5-Benzenetetracarboxylic dianhydride (13.8 mmol), diisopropylethyl amine, N-(3-phenoxybenzyl)-N-[(1S)-1,2,3,4-tetrahydro-1-naphthalenyl]amine and methanol were processed as described in Example 100. The residue was purified by flash chromatography (silica gel, 95:5 CH$_2$Cl$_2$:methanol to 8:2 CH$_2$Cl$_2$:methanol) to provide the title compounds as an off-white solid (120 mg, 21% yield).

¹H NMR (500 MHz, d₆-DMSO) δ8.23 and 8.33 (2s, 1H); 6.58–7.53 (m, 14H); 4.65 and 5.59 (2 br t, 1H); 4.17 and 4.81 (2m, 2H); 3.68, 3.71, and 3.73 (3s, 3H); 2.53 (m, 2H); 1.39–2.02 (m, 4H); MS (ESI+) m/z (M+H)⁺580.

EXAMPLE 104

2-hydroxy-5-({(3-phenoxybenzyl)[(1S)-1,2,3,4-tetrahydro-1-naphthalenyl]amino}carbonyl)terephthalic acid and 4-hydroxy-6-({(3-phenoxybenzyl)[(1S)-1,2,3,4-tetrahydro-1-naphthalenyl]amino}carbonyl)isophthalic acid

EXAMPLE 104A 6-(acetyloxy)-1,3-dioxo-1,3-dihydro-2-benzofuran-5-carboxylic acid 4-Hydroxy-benzene-1,2,5-tricarboxylic acid (4.1 g, 18.1 mmol), prepared according to J. Am. Chem. Soc. (1949) 71, 11, was treated with acetic anhydride (50 mL) and heated at reflux for 5 hours. The mixture was allowed to cool to room temperature and then concentrated under reduced pressure. The orange-pink residue was washed with diethyl ether (3×30 mL) and dried under reduced pressure at room temperature overnight to provide the title compound (1.71 g, 38%).

EXAMPLE 104B 2-(acetyloxy)-5-({[3-(4-chlorophenoxy)benzyl][(1S)-1,2,3,4-tetrahydro-1-naphthalenyl]amino}carbonyl)terephthalic acid and 4-(acetyloxy)-6-({[3-(4-chlorophenoxy)benzyl][(1S)-1,2,3,4-tetrahydro-1-naphthalenyl]amino}carbonyl)isophthalic acid The product from Example 104A (1.7 g, 6.8 mmol) and diisopropylethyl amine (4 mL, 23 mmol) in THF (60 mL) were treated with N-(3-phenoxybenzyl)-N-[(1S)-1,2,3,4-tetrahydro-1-naphthalenyl]amine (14 mL, 0.5M solution in ClCH₂CH₂Cl, 7 mmol). After stirring at room temperature overnight, the organic solvents were removed under reduced pressure and the residue partitioned between ethyl acetate (100 mL) and 1N HCl (20 mL). The phases were separated and the organic layer was washed with 1N HCl (20 mL), water (20 mL), brine (20 mL), dried over Na₂SO₄, filtered and the filtrate concentrated under reduced pressure. The residue was purified by flash chromatography (silica gel, 6:4 hexanes/ethyl acetate, then 9:1 CH₂Cl₂:methanol) to provide the title compound as a pale beige foamy solid (0.97 g, 25%).

¹H NMR (500 MHz, DMSO-d₆) δ8.50, 8.43, 8.31, 7.75, 7.64, 7.55 (6 s, 2H); 6.56–7.43 (m, 13H); 5.60 and 4.66 (2 m, 11H); 4.79 and 4.15 (2 m, 2H); 2.61 (m, 2H); 2.28, 2.26, 2.07 (3 s, 3H); 1.44–2.09 (m, 4H); MS (ESI+) 580 (M+H)⁺.

EXAMPLE 104C 2-hydroxy-5-({(3-phenoxybenzyl)[(1S)-1,2,3,4-tetrahydro-1-naphthalenyl]amino carbonyl)terephthalic acid and 4-hydroxy-6-({(3-phenoxybenzyl)[(1S)-1,2,3,4-tetrahydro-1-naphthalenyl]amino}carbonyl)isophthalic acid The products from Example 104B (0.97 g, 1.68 mmol) in methanol (60 mL) were treated with NaHCO₃ (3.9 g, 46.4 mmol) in water (30 mL) and the mixture was stirred at room temperature for 24 hours. The methanol was removed under reduced pressure and the remaining aqueous solution was acidified to pH 1 with 1N HCl. The acidified solution was extracted with ethyl acetate (5×15 mL). The organic extracts were combined, washed with brine (10 mL), dried over Na₂SO₄, filtered and the filtrate concentrated under reduced pressure. The residue was purified by flash chromatography (silica gel, 9:1 CH₂Cl₂:methanol to 8:2 CH₂Cl₂:methanol) to provide the title compounds as a foamy white solid (208 mg, 23%).

¹H NMR (500 MHz, DMSO-d₆) δ8.36, 8.31, 7.79, 7.39 (4 s, 2H); 6.45–7.44 (m, 13); 4.83 (m, 2H); 4.72 (m, 1H); 2.60 (m, 2H); 1.43–2.07 (m, 4H); HRMS (FAB) calculated for C₃₂H₂₈NO₇ 538.1866 (M+H)⁺. Found: 538.1862 (M+H)⁺.

EXAMPLE 105

2-({(3-phenoxybenzyl)[(1S)-1,2,3,4-tetrahydro-1-naphthalenyl]amino}carbonyl)-5-sulfoterephthalic acid and 4-({(3-phenoxybenzyl)[(1S)-1,2,3,4-tetrahydro-1-naphthalenyl]amino}carbonyl)-6-sulfoisophthalic acid

EXAMPLE 105A 1,3-dioxo-6-sulfo-1,3-dihydro-2-benzofuran-5-carboxylic acid

5-Sulfo-1,2,4-benzenetricarboxylic acid (9.63 g, 33.2 mmol), prepared according to J. Am. Chem. Soc. (1949) 71, 11, was treated with acetic anhydride (150 mL) and refluxed for 5 hours. After cooling to room temperature, the acetic anhydride was removed under reduced pressure. The residue was washed with diethyl ether (3×30 mL) and then dried under reduced pressure at room temperature to provide the title compound as a tan solid.

EXAMPLE 105B 2-({(3-phenoxybenzyl)[(1S)-1,2,3,4-tetrahydro-1-naphthalenyl]amino}carbonyl)-5-sulfoterephthalic acid and 4-({(32-phenoxybenzyl)[(1S)-1,2,3,4-tetrahydro-1-naphthalenyl]amino}carbonyl)-6-sulfoisophthalic acid The product from Example 105A (2 g, 7.35 mmol) and diisopropylethyl amine (2.5 mL, 14.6 mmol) in THF (40 mL) were treated with N-(3-phenoxybenzyl)-N-[(1S)-1,2,3,4-tetrahydro-1-naphthalenyl]amine (10 mL, 0.5M solution in ClCH₂CH₂Cl, 5 mmol). After stirring at room temperature overnight, the organics were removed under reduced pressure and the residue was dissolved in ethyl acetate. The ethyl acetate solution was washed with 1N HCl, brine, dried over Na₂SO₄, filtered and the filtrate concentrated under reduced pressure. The residue was purified by several rounds of flash chromatography followed by a Prep Nova Pak (HRC18) column using 0.1% trifluoroacetic acid:acetonitrile (10:90 to 95:5) as eluant to provide the title compounds.

¹H NMR (500 MHz, DMSO-d₆) δ8.36, 8.31, 8.15, and 7.71 (4s, 2H); 6.77–7.94 (m, 13H); 4.77 and 5.41 (2m, 1H); 4.16 and 4.79 (2m, 2H); 2.60 (m, 2H); 1.33–1.98 (m, 4H); MS (EST) 600 (M–H)⁻.

EXAMPLE 106

5-({[3-(4-pyridinyloxy)benzyl][(1S)-1,2,3,4-tetrahydro-1-naphthalenyl]amino}carbonyl)-1,2,4-benzenetricarboxylic acid

EXAMPLE 106A

N-[3-(4-pyridinyloxy)benzyl]-N-[(1S)-1,2,3,4-tetrahydro-1-naphthalenyl]amine 3-(4-Pyridinyloxy)benzaldehyde (0.85 g, 4.27 mmol), prepared according to J. Chem. Soc. Perkin Trans 2 (1987)

1867, and (1S)-1,2,3,4-tetrahydro-1-naphthalenylamine (0.63 g, 4.29 mmol) were combined in ethanol (10 mL), briefly heated and the solvent removed under reduced pressure. This process was repeated twice more. The residual oil was dissolved in ethanol (5 mL) and stirred with sodium borohydride (0.16 g, 4.23 mmol) overnight at room temperature. The reaction mixture was quenched with water (10 mL) and diluted with diethyl ether (50 mL). The diethyl ether was washed with saturated NaHCO$_3$ solution (3×10 mL), brine (10 mL), dried over Na$_2$SO$_4$, filtered and the filtrate concentrated under reduced pressure to provide the title compound as a thick orange liquid (1.19 g, 85% yield).

$^1$H NMR (300 MHz, CDCl$_3$) δ8.52 and 8.46 (2 dd, 2H), 6.91–7.38 (m, 8H); 6.71 and 6.86 (2 dd, 2H), 3.82 (m, 3H), 2.78 (m, 2H), 2.03 and 1.77 (2m, 2H), 1.92 (q, 2H); MS (ESI+) 331 (M+H)$^+$.

EXAMPLE 106B 5-({[3-(4-pyridinyloxy)benzyl][(1S)-1,2,3,4-tetrahydro-1-naphthalenyl]amino}carbonyl)-1,2,4-benzenetricarboxylic acid The product from Example 106A (1.17 g), diisopropylethyl amine (2.5 mL, 14.4 mmol) and 1,2,4,5-benzenetetracarboxylic dianhydride (0.78 g, 3.58 mmol) in THF (30 mL) were processed as described in Example 1B. The reaction mixture was treated with saturated Na$_2$CO$_3$ solution (30 mL), and stirred vigorously at room temperature for 1 hour. The layers were separated and the aqueous layer was acidified with 1N HCl. The acidified aqueous layer was evaporated under reduced pressure to afford off-white plates. Soxhlet extraction (ethanol) of the crude solid, followed by RP-HPLC, provided the title compound (20 mg).

$^1$H NMR (500 MHz, DMSO-d$_6$) δ8.63 and 8.68 (2m, 2H); 8.18 and 8.26 (2s, 2H); 7.44 and 7.52 (2m, 2H); 6.46–7.82 (m, 8H); 4.68 and 5.37 (2m, 1H); 4.14 and 4.88 (2m, 2H); 2.61 (m, 2H); 1.37–2.12 (m, 4H); MS (ESI+) 567 (M+H)$^+$.

EXAMPLE 107

5-({[3-(2-pyrimidinyloxy)benzyl][(1S)-1,2,3,4-tetrahydro-1-naphthalenyl]amino}carbonyl)-1,2,4-benzenetricarboxylic acid

EXAMPLE 107A

N-[3-(2-pyrimidinyloxy)benzyl]-N-[(1S)-1,2,3,4-tetrahydro-1-naphthalenyl]amine 3-(2-Pyrimidinyloxy)benzaldehyde (0.67 g, 3.35 mmol) and (1S)-1,2,3,4-tetrahydro-1-naphthalenylamine (0.49 g, 3.33 mmol) were processed as described in Example 106A. The residue was purified by flash chromatography (silica gel, 6:4 ethyl acetate:hexanes to 1:1 ethyl acetate:hexanes) to provide the title compound (190 mg, 19% yield).

$^1$H NMR (300 MHz, CDCl$_3$) δ8.55 (d, 2H), 7.01–7.42 (m, 9H), 3.94 (m, 2H), 3.83 (t, 1H), 2.78 (m, 2H), 1.68–2.07 (m, 4H); MS (ESI+) 332 (M+H)$^+$.

EXAMPLE 107B 5-({[3-(2-pyrimidinyloxy)benzyl][(1S)-1,2,3,4-tetrahydro-1-naphthalenyl]amino}carbonyl)-1,2,4-benzenetricarboxylic acid The product from Example 107A, 1,2,4,5-benzenetetracarboxylic dianhydride (0.125 g, 0.57 mmol) and diisopropylethyl amine (0.4 mL, 2.3 mmol) were processed as described in Example 1B. The reaction mixture was treated with saturated Na$_2$CO$_3$ solution (30 mL) and stirred vigorously at room temperature for 1 hour. The layers were separated and the aqueous layer was acidified with 1N HCl. The acidified aqueous layer was evaporated under reduced pressure to afford a solid. Soxhlet extraction (ethanol) of the crude solid, followed by RP-HPLC, provided the title compound (4 mg).

HRMS (FAB) calculated for C$_{31}$H$_{26}$N$_3$O$_8$ 568.1720 (M+H)$^+$. Found 568.1713 (M+H)$^+$.

EXAMPLE 108

4-({[[(4-methoxyphenyl)sulfonyl]amino}carbonyl)-6-({{(3-phenoxybenzyl)[(1S)-1,2,3,4-tetrahydro-1-naphthalenyl]amino}carbonyl)isophthalic acid and 2-({[[(4-methoxyphenyl)sulfonyl]amino}carbonyl)-5-({{(3-phenoxybenzyl)[(1S)-1,2,3,4-tetrahydro-1-naphthalenyl]amino}carbonyl)terephthalic acid The product from Example 36B (114 mg, 0.2 mmol), 4-methoxybenzenesulfonamide (37 mg, 0.2 mmol), DMAP (25 mg, 0.2 mmol), and EDCI (78 mg, 0.4 mmol) were combined in THF (10 mL) at room temperature. After stirring overnight, the mixture was concentrated under reduced pressure and CH$_2$Cl$_2$ (20 mL) was added. The mixture was washed with water and the organic layer concentrated under reduced pressure. The residue was purified via HPLC to provide the title compounds. $^1$H (500 MHz; DMSO-d$_6$) δ6.4–8.6 (m, br., 20H) 5.0 (m, 1H) 4.7 (m, 1H) 4.1 (m, 1H) 3.5 (br, 3H) 1.4–2.7 (m, 6H); MS (M+H)$^+$ 735.

EXAMPLE 109

4-({[[(3-chloro-4-methylphenyl)sulfonyl]amino}carbonyl)-6-({{(3-phenoxybenzyl)[(1S)-1,2,3,4-tetrahydro-1-nanhthalenyl]amino}carbonyl)isophthalic acid and 2-({[[(3-chloro-4-methylphenyl)sulfonyl]amino}carbonyl)-5-({{(3-phenoxybenzyl)[(1S)-1,2,3,4-tetrahydro-1-naphthalenyl]amino}carbonyl)terephthalic acid 3-Chloro-4-methylbenzenesulfonamide was processed as described in Example 108 to provide the title compounds. $^1$H (500 MHz; DMSO-d$_6$) δ6.4–8.6 (m, 19H) 5.1 (m, 1H) 4.7 (m, 1H) 4.2 (m, 1H) 2.4 (br, 3H) 1.4–2.7 (m, 6H); MS (M+H)$^+$754.

EXAMPLE 110

4-({[[(2-chlorophenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[[(2-chlorophenyl)sulfonyl]amino}carbonyl)-5-({(3-phenoxybenzyl)[(1S)-1,2,3,4-tetrahydro-1-naphthalenyl]amino}carbonyl)terephthalic acid 2-Chlorobenzenesulfonamide was processed as described in Example 108 to provide the title compounds. $^1$H (500 MHz; DMSO-d$_6$) δ6.4–8.6 (m, 20H) 5.1 (m, 1H) 4.7 (m, 1H) 4.1 (m, 1H) 1.4–2.7 (m, 6H) MS (M+H)$^+$740.

EXAMPLE 111

4-({[[(3-chlorophenyl)sulfonyl]amino}carbonyl)-6-({(3-phenoxybenzyl)[(1S)-1,2,3,4-tetrahydro-1-nanhthalenyl]amino}carbonyl)isophthalic acid and 2-({[[(3-chlorophenyl)sulfonyl]amino}carbonyl)-5-({(3-phenoxybenzyl)[(1S)-1,2,3,4-tetrahydro-1-naphthalenyl]amino}carbonyl)terephthalic acid 3-Chlorobenzenesulfonamide was processed as described in Example 108 to provide the title compounds. $^1$H (500

MHz; DMSO-d$_6$) δ6.4–8.6 (m, 20H) 5.1 (m, 1H) 4.7 (m, 1H) 4.1 (m, 1H) 1.4–2.7 (m, 6H) MS (M+H)$^+$740.

EXAMPLE 112

4-({[(4-chlorophenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(4-chlorophenyl)sulfonyl]amino}carbonyl)-5-({(3-phenoxybenzyl)[(1S)-1,2,3,4-tetrahydro-1-naphthalenyl]amino}carbonyl)terephthalic acid 4-Chlorobenzenesulfonamide was processed as described in Example 108 to provide the title compounds. $^1$H (500 MHz; DMSO-d$_6$) δ6.4–8.6 (m, 20H) 5.0 (d, 1H) 4.7 (m, 1H) 4.2 (m, 1H) 1.4–2.7 (m, 6H); MS (M+H)$^+$740.

EXAMPLE 114

4-({[(4-nitrophenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(4-nitrophenyl)sulfonyl]amino}carbonyl)-5-({(3-phenoxybenzyl)[(1S)-1,2,3,4-tetrahydro-1-naphthalenyl]amino}carbonyl)terephthalic acid 4-Nitrobenzenesulfonamide was processed as described in Example 108 to provide the title compounds. $^1$H (500 MHz; DMSO-d$_6$) δ6.4–8.6 (m, 20H); 5.0 (m, 1H); 4.7 (m 1H); 4.1 (m, 1H); 1.4–2.7 (m, 6H). MS (M+H)$^+$750.

EXAMPLE 115

4-({[(4-bromophenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(4-bromophenyl)sulfonyl]amino}carbonyl)-5-({(3-phenoxybenzyl)[(1S)-1,2,3,4-tetrahydro-1-naphthalenyl]amino}carbonyl)terephthalic acid 4-Bromobenzenesulfonamide was processed as described in Example 108 to provide the title compounds. $^1$H (500 MHz; DMSO-d$_6$) δ6.4–8.6 (m, 20H); 5.0 (d, 1H); 4.7 (m, 1H); 42 (m, 1H); 1.4–2.7 (m, 6H). MS (M+H)$^+$784.

EXAMPLE 116

4-({[(3-nitrophenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(3-nitrophenyl)sulfonyl]amino}carbonyl)-5-({(3-phenoxybenzyl)[(1S)-1,2,3,4-tetrahydro-1-naphthalenyl]amino}carbonyl)terephthalic acid 3-Nitrobenzenesulfonamide was processed as described in Example 108 to provide the title compounds. $^1$H (500 MHz; DMSO-d$_6$) δ6.4–8.6 (m, 20H); 5.0 (m, 1H); 4.7 (m, 1H); 4.2 (m, 1H); 1.4–2.7 (m, 6H). MS (M+H)$^+$750.

EXAMPLE 117

4-({[(phenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(phenyl)sulfonyl]amino}carbonyl)-5-({(3-phenoxybenzyl)[(1S)-1,2,3,4-tetrahydro-1-naphthalenyl]amino}carbonyl)terephthalic acid Benzenesulfonamide was processed as described in Example 108 to provide the title compounds. $^1$H (500 MHz; DMSO-d$_6$) δ6.4–8.6 (m, 21H); 5.0 (m, 1H); 4.7 (m, 1H); 4.2 (m, 1H); 1.4–2.7 (m, 6H). MS (M+H)$^+$705.

EXAMPLE 118

4-({[(2-nitrophenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(2-nitrophenyl)sulfonyl]amino}carbonyl)-5-({(3—phenoxybenzyl)[(1S)-1,2,3,4-tetrahydro-1-naphthalenyl]amino}carbonyl)terephthalic acid 2-Nitrobenzenesulfonamide was processed as described in Example 108 to provide the title compounds. $^1$H (500 MHz; DMSO-d$_6$) δ6.4–8.6 (m, 20H); 5.0 (m, 1H); 4.7 (m, 1H); 4.2 (m, 1H); 1.4–2.7 (m, 6H). MS (M+H)$^+$750.

EXAMPLE 119

4-({[(2-methylphenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(2-methylphenyl)sulfonyl]amino}carbonyl)-5-({(3-phenoxybenzyl)[(1S)-1,2,3,4-tetrahydro-1-naphthalenyl]amino}carbonyl)terephthalic acid 2-Methylbenzenesulfonamide was processed as described in Example 108 to provide the title compounds. $^1$H (500 MHz; DMSO-d$_6$) δ6.4–8.6 (m, 20H); 5.0 (d, 1H); 4.7 (m, 1H); 4.2 (m, 1H); 2.7 (br., 3H); 1.4–2.7 (m, 6H). MS (M+H)$^+$719.

EXAMPLE 120

4-{[({4-[(2,3-dihydroxypropyl)amino]phenyl}sulfonyl]amino}carbonyl)-6-({(3-phenoxybenzyl)[(1S)-1,2,3,4-tetrahydro-1-naphthalenyl]amino}carbonyl)isophthalic acid and 2-{[(4-[(2,3-dihydroxypropyl)amino]phenyl}sulfonyl)amino]carbonyl}-5-({(3-phenoxybenzyl)[(1S)-1,2,3,4-tetrahydro-1-naphthalenyl]amino}carbonyl)terephthalic acid 4-[(2,3-Dihydroxypropyl)amino]benzenesulfonamide was processed as described in Example 108 to provide the title compounds. $^1$H (500 MHz; DMSO-d$_6$) δ6.4–8.6 (m, 20H); 5.0 (m, 1H); 4.1–4.7 (m, 8H); 1.4–2.7 (m, 6H). MS (M+H)$^+$794.

EXAMPLE 121

2-({[(4-{[(methylamino)carbonyl]amino}phenyl)sulfonyl]amino}carbonyl)-5-({(3-phenoxybenzyl)[(1S)-1,2,3,4-tetrahydro-1-naphthalenyl]amino}carbonyl)terephthalic acid and 4-({[(4-{[(methylamino)carbonyl]amino}phenyl)sulfonyl]amino}carbonyl)-6-({(3-phenoxybenzyl)[(1S)-1,2,3,4-tetrahydro-1-nanhthalenyl]amino}carbonyl)isophthalic acid 4-{[(Methylamino)carbonyl]amino}benzenesulfonamide was processed as described in Example 108 to provide the title compounds. $^1$H (500 MHz; DMSO-d$_6$) δ6.4–8.6 (m, 22H); 5.0 (m, 1H); 4.7 (m, 1H); 4.2 (m, 1H); 2.8 (m, 3H); 1.4–2.7 (m, 6H). MS (M+H)$^+$777.

EXAMPLE 122

4-[({[4-(butyrylamino)phenyl]sulfonyl}amino)carbonyl]-6-({(3-phenoxybenzyl)[(1S)-1,2,3,4-tetrahydro-1-naphthalenyl]amino}carbonyl)isophthalic acid and 2-[({[4-(butyrylamino)phenyl]sulfonyl}amino)carbonyl]-5-({(3-phenoxybenzyl)[(1S)-1,2,3,4-tetrahydro-1-naphthalenyl]amino}carbonyl)terephthalic acid N-[4-(Aminosulfonyl)phenyl]butanamide was processed as described in Example 108 to provide the title compounds.

¹H (500 MHz; DMSO-d₆) δ6.4–8.6 (m, 21H); 5.0 (m, 1H); 4.7 (m, 1H); 4.2 (m, 1H); 1.4–2.7 (m, 10H); 1.0 (m, 3H). MS (M+H)⁺790.

EXAMPLE 123

4-({[(3,4-difluorophenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(3,4-difluorophenyl)sulfonyl]amino}carbonyl)-5-({(3-phenoxybenzyl)[(1S)-1,2,3,4-tetrahydro-1-naphthalenyl]amino}carbonyl)terephthalic acid 3,4-Difluorobenzenesulfonamide was processed as described in Example 108 to provide the title compounds. ¹H (500 MHz; CD₂Cl₂) δ6.6–8.1 (m, 19H); 4.9 (d, 1H); 4.7 (m, 1H); 4.1 (m, 1H); 1.3–3.0 (m, 6H). MS (M+H)⁺741.

EXAMPLE 124

4-({[(2,5-difluorophenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(2,5-difluorophenyl)sulfonyl]amino}carbonyl)-5-({(3-phenoxybenzyl)[(1S)-1,2,3,4-tetrahydro-1-naphthalenyl]amino}carbonyl)terephthalic acid 2,5-Difluorobenzenesulfonamide was processed as described in Example 108 to provide the title compounds. ¹H (500 MHz; CD₂Cl₂) δ6.8–8.1 (m, 19H); 5.0 (d, 1H); 4.7 (m, 1H); 4.2 (m, 1H); 1.4–2.8 (m, 6H). MS (M+H)⁺741.

EXAMPLE 125

4-({[(2-methoxy-4-methylphenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(2-methoxy-4-methylphenyl)sulfonyl]amino}carbonyl)-5-({(3-phenoxybenzyl)[(1S)-1,2,3,4-tetrahydro-1-naphthalenyl]amino}carbonyl)terephthalic acid 2-Methoxy-4-methylbenzenesulfonamide was processed as described in Example 108 to provide the title compounds. ¹H (500 MHz; CD₂Cl₂) δ6.9–8.7 (m, 19H); 5.1 (m, 1H); 4.8 (m, 1H); 4.3 (m, 1H); 3.3 (br, 3H); 2.5 (m, 3H); 1.4–2.8 (m, 6H). MS (M+H)⁺749.

EXAMPLE 126

4-({[(5-methyl-2-pyridinyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(5-methyl-2-pyridinyl)sulfonyl]amino}carbonyl)-5-({(3-phenoxybenzyl)[(1S)-1,2,3,4-tetrahydro-1-naphthalenyl]amino}carbonyl)terephthalic acid 5-Methyl-2-pyridinesulfonamide was processed as described in Example 108 to provide the title compounds. ¹H (500 MHz; CD₂Cl₂) δ6.9–8.7 (m, 19H); 4.9 (m, 1H); 4.7 (m, 1H); 4.2 (m, 1H); 2.4 (m, 3H); 1.4–2.8 (m, 6H). MS (M+H)⁺720.

EXAMPLE 127

4-{[(methylsulfonyl)amino]carbonyl}-6-({(3-phenoxybenzyl)[(1S)-1,2,3,4-tetrahydro-1-naphthalenyl]amino}carbonyl)isophthalic acid and 2-{[(methylsulfonyl)amino]carbonyl}-5-({(3-phenoxybenzyl)[(1S)-1,2,3,4-tetrahydro-1-naphthalenyl]amino}carbonyl)terephthalic acid Methanesulfonamide was processed as described in Example 108 to provide the title compounds. ¹H (500 MHz; CD₂Cl₂) δ6.9–8.7 (m, 16H); 4.9 (d, 1H); 4.7 (m, 4.2 (m, 1H); 2.0 (s, 3H); 1.4–2.8 (m, 6H). MS (M+H)⁺643.

EXAMPLE 128

4-({[(5-nitro-2-thienyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(5-nitro-2-thienyl)sulfonyl]amino}carbonyl)-5-({(3-phenoxybenzyl)[(1S)-1,2,3,4-tetrahydro-1-naphthalenyl]amino}carbonyl)terephthalic acid 5-Nitro-2-thiophenesulfonamide was processed as described in Example 108 to provide the title compounds. ¹H (500 MHz; CD2Cl2) δ6.9–8.8 (m, 18H); 4.9 (m, 1H); 4.7 (m, 1H); 4.2 (m, 1H); 1.4–2.8 (m, 6H). MS (M+H)⁺756.

EXAMPLE 130

4-({[(4-methylphenyl)sulfonyl]amino}carbonyl)-6-({(3-phenoxybenzyl)[(1S)-1,2,3,4-tetrahydro-1-naphthalenyl]amino}carbonyl)isophthalic acid and 2-({[(4-methylphenyl)sulfonyl]amino}carbonyl)-5-({(3-phenoxybenzyl)[(1S)-1,2,3,4-tetrahydro-1-naphthalenyl]amino}carbonyl)terephthalic acid 4-Methylbenzenesulfonamide was processed as described in Example 108 to provide the title compounds. ¹H (500 MHz; CD₂Cl₂) δ6.9–8.6 (m, 20H); 4.9 (m, 1H); 4.7 (m, 1H); 4.1 (m, 1H); 2.4 (m, 3H); 1.4–2.8 (m, 6H). MS (M+H)⁺719.

EXAMPLE 131

4-{[(benzylsulfonyl)amino]carbonyl}-6-({(3-phenoxybenzyl)[(1S)-1,2,3,4-tetrahydro-1-naphthalenyl]amino}carbonyl)isophthalic acid and 2-{[(benzylsulfonyl)amino]carbonyl}-5-({(3-phenoxybenzyl)[(1S)-1,2,3,4-tetrahydro-1-naphthalenyl]amino}carbonyl)terephthalic acid 1-Phenylmethanesulfonamide was processed as described in Example 108 to provide the title compounds. ¹H (500 MHz; CD₂Cl₂) δ6.9–8.8 (m, 20H); 4.9 (d, 1H); 4.7 (m, 3H); 4.1 (m, 1H); 1.4–2.8 (m, 6H). MS (M+H)⁺719.

EXAMPLE 132

2-({[(2-fluorophenyl)sulfonyl]amino}carbonyl)-5-({(3-phenoxybenzyl)[(1S)-1,2,3,4-tetrahydro-1-naphthalenyl]amino}carbonyl)terephthalic acid and 4-({[(2-fluorophenyl)sulfonyl]amino}carbonyl)-6-({(3-phenoxybenzyl)[(1S)-1,2,3,4-tetrahydro-1-naphthalenyl]amino}carbonyl)isophthalic acid 2-Fluorobenzenesulfonamide was processed as described in Example 108 to provide the title compounds. ¹H (500 MHz; CD₂Cl₂) δ6.9–8.8 (m, 20H); 4.9 (m, 1H); 4.7 (m, 1H); 4.1 (m, 1H); 1.4–2.8 (m, 6H). MS (M+H)⁺723.

EXAMPLE 133

2-({[(5-chloro-2-thienyl)sulfonyl]amino}carbonyl)-5-({(3-phenoxybenzyl)[(1S)-1,2,3,4-tetrahydro-1-naphthalenyl]amino}carbonyl)terephthalic acid and 4-({[(5-chloro-2-thienyl)sulfonyl]amino}carbonyl)-6-({(3-phenoxybenzyl)[(1S)-1,2,3,4-tetrahydro-1-naphthalenyl]amino}carbonyl)isophthalic acid 5-Chloro-2-thiophenesulfonamide was processed as described in Example 108 to provide the title compounds.

¹H (500 MHz; CD₂Cl₂) δ6.9–8.8 (m, 18H); 4.9 (d, 1H) 4.7 (m, 1H); 4.2 (m, 1H); 1.4–2.8 (m, 6H). MS (M+H)⁺746.

EXAMPLE 134

2-({[(4-hydroxyphenyl)sulfonyl]amino}carbonyl)-5-({(3-phenoxybenzyl)[(1S)-1,2,3,4-tetrahydro-1-naphthalenyl]amino}carbonyl)terephthalic acid and 4-({[(4-hydroxyphenyl)sulfonyl]amino}carbonyl)-6-({(3-phenoxybenzyl)[(1S)-1,2,3,4-tetrahydro-1-naphthalenyl]amino}carbonyl)isophthalic acid 4-Hydroxybenzenesulfonamide was processed as described in Example 108 to provide the title compounds. ¹H (500 MHz; CD₂Cl₂) δ6.9–8.8 (m, 20H); 4.9 (m, 1H); 4.7 (m, 1H); 4.2 (m, 1H); 1.4–2.8 (m, 6H). MS (M+H)⁺721.

EXAMPLE 135

6-({[(3',4'-dichloro-1,1'-biphenyl-3-yl)methyl][(1S)-1,2,3,4-tetrahydro-1-naphthalenyl]amino}carbonyl)-1,3-dioxo-1,3-dihydro-2-benzothiophene-5-carboxylic acid

EXAMPLE 135A

3',4'-dichloro-1,1'-biphenyl-3-carbaldehyde

3-Bromobenzaldehyde (3.16 g, 17 mmol) and 3,4-dichloroboronic acid (4.3 g, 22 mmol) in DME (200 mL) was treated with 3M Na₂CO₃ (28 mL, 85 mmol) and tetrakis(triphenylphosphine)palladium (II) (1.0 g, 0.85 mmol). The mixture was refluxed for 15 hours, allowed to cool to ambient temperature, diluted with ethyl acetate, and washed with 1N HCl and water. The organic layer was separated, concentrated under reduced pressure, and the residue purified by column chromatography (ethylacetate:hexane, 5:95) to provide the title compound. MS (DCI/NH₃) 250 (M+H)⁺.

EXAMPLE 135B

N-[(3',4'-dichloro-1,1'-biphenyl-3-yl)methyl]-N-[(1S)-1,2,3,4-tetrahydro-1-naphthalenyl]amine The product from Example 135A (2.1 g, 8.8 mmol) and (1S)-1,2,3,4-tetrahydro-1-naphthalenamine (1.43 g, 9.7 mmol) in ethanol (100 mL) were combined and stirred for 15 hours at ambient temperature. The mixture was treated with sodium borohydride (1.7 g, 44 mmol) and stirred an additional 3 hours. The mixture was treated with 3N HCl (4 mL) and diluted with ethylacetate. The organic layer was separated and concentrated to provide the title compound. MS (DCI/NH₃) 382 (M+H)⁺.

EXAMPLE 135C 6-({[(3',4'-dichloro-1,1'-biphenyl-3-yl)methyl][(1S)-1,2,3,4-tetrahydro-1-naphthalenyl]amino}carbonyl)-1,3-dioxo-1,3-dihydro-2-benzothiophene-5-carboxylic acid 1,2,4,5-Benzenetetracarboxylic dianhydride (8.0 g, 37.5 mmol) and triethylamine (14 mL, 102 mmol) in THF (300 mL) at −78° C. was treated with the product from Example 135B (13.0 g, 34.1 mmol) in ethanol (20 mL) over the period of 10 minutes. The mixture was allowed to gradually warm to room temperature and stir over night. The mixture was concentrated under reduced pressure and the residue was dissolved in THF (200 mL) and water (30 mL). The mixture was treated with sodium sulfide (1.33 g, 17 mmol) and stirred at ambient temperature for 1.5 hours. The mixture was diluted with ethyl acetate and washed in succession with water, 1N HCl (X2), and water. The organic phase was separated and concentrated under reduced pressure to provide the title compound. MS (DCI/NH₃) 616 (M+H)⁺.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I):

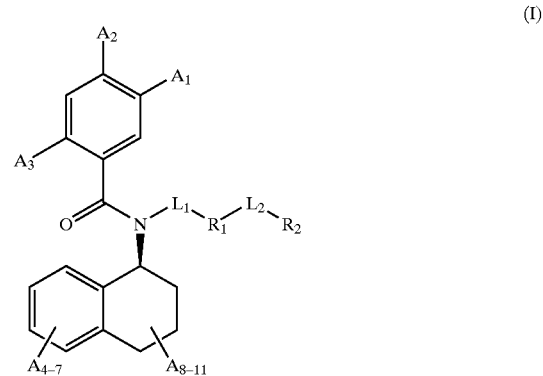

or a pharmaceutically acceptable salt thereof, wherein $A_1$ and $A_2$ are each independently selected from the group consisting of alkoxycarbonyl, alkylcarbonyloxy, carboxy, hydroxy, hydroxyalkyl, $(NR_AR_B)$carbonyl, —$NR_CS(O)_2R_D$, —$S(O)_2OH$; or $A_3$ is selected from the group consisting of alkoxycarbonyl, alkylcarbonyloxy, carboxy, hydroxy, hydroxyalkyl, $(NR_AR_B)$carbonyl, $NR_CS(O)_2R_D$, —$S(O)_2OH$;

$A_4$, $A_5$, $A_6$ and $A_7$ are each independently selected from the group consisting of hydrogen, alkoxy, alkoxycarbonyl, alkenyl, alkyl, alkylcarbonyl, alkylcarbonyloxy, alkynyl, aryl, carboxy, cyano, haloalkoxy, haloalkyl, halogen, hydroxy, hydroxyalkyl, nitro, —$NR_ER_F$ and $(NR_ER_F)$carbonyl;

$A_8$, $A_9$, $A_{10}$ and $A_{11}$ are each independently selected from the group consisting of hydrogen, alkoxy, alkoxycarbonyl, alkenyl, alkyl, alkylcarbonyl, alkylcarbonyloxy, alkynyl, aryl, carboxy, haloalkoxy, haloalkyl, halogen, hydroxy, hydroxyalkyl, —$NR_ER_F$ and $(NR_ER_F)$carbonyl and oxo;

$R_A$ and $R_B$ are each independently selected from the group consisting of hydrogen, alkyl and cyano;

$R_C$ is selected from the group consisting of hydrogen and alkyl;

$R_D$ is selected from the group consisting of alkoxy, alkyl, aryl, arylalkoxy, arylalkyl, haloalkoxy and haloalkyl;

$R_E$ and $R_F$ are each independently selected from the group consisting of hydrogen, alkyl, alkylcarbonyl, formyl, and hydroxyalkyl;

87

L$_1$ is selected from the group consisting of alkenylene, alkylene, alkynylene, —(CH$_2$)$_m$O(CH$_2$)$_n$—, —(CH$_2$)$_m$S(CH$_2$)$_n$— and —(CH$_2$)$_p$C(O)(CH$_2$)$_q$— wherein each group is drawn with the left end attached to N and the right end attached to R$_1$;

m is an integer 0–10;

n is an integer 0–10;

R$_1$ is selected from the group consisting of aryl, cycloalkenyl, and cycloalkyl;

L$_2$ is absent or selected from the group consisting of a covalent bond, alkenylene, alkylene, alkynylene, —(CH$_2$)$_p$O(CH$_2$)$_q$—, —(CH$_2$)$_p$S(CH$_2$)$_q$—, —(CH$_2$)$_p$C(O)(CH$_2$)$_q$—, —(CH$_2$)$_p$C(OH)(CH$_2$)$_q$— and —(CH$_2$)$_p$CH=NO(CH$_2$)$_q$— wherein each group is drawn with the left end attached to R$_1$ and the right end attached to R$_2$;

p is an integer 0–10;

q is an integer 0–10; and

R$_2$ is absent or selected from the group consisting of aryl, cycloalkenyl, and cycloalkyl.

2. A compound according to claim 1 wherein

A$_1$ and A$_2$ are each independently selected from the group consisting of alkoxycarbonyl, carboxy, hydroxy, (NR$_A$R$_B$)carbonyl, —NR$_C$S(O)$_2$R$_D$, and —S(O)$_2$OH;

A$_3$ is carboxy;

A$_4$, A$_5$, A$_6$, A$_7$, A$_8$, A$_9$, A$_{10}$ and A$_{11}$ are each hydrogen;

R$_A$ and R$_B$ are each independently selected from the group consisting of hydrogen, alkyl and cyano;

L$_1$ is selected from the group consisting of alkylene and —(CH$_2$)$_m$O(CH$_2$)$_n$—;

R$_1$ is selected from the group consisting of aryl, and cycloalkyl;

L$_2$ is absent or selected from the group consisting of a covalent bond, alkylene, —(CH$_2$)$_p$O(CH$_2$)$_q$—, —(CH$_2$)$_p$C(O)(CH$_2$)$_q$—, —(CH$_2$)$_p$C(OH)(CH$_2$)$_q$—, —(CH$_2$)$_p$S(CH$_2$)$_q$—, and —(CH$_2$)$_p$CH=NO(CH$_2$)$_q$—;

p is 0;

q is an integer 0–1; and

R$_2$ is absent or selected from the group consisting of aryl, and cycloalkenyl, cycloalkyl.

3. A compound according to claim 1 wherein

L$_1$ is alkylene;

R$_1$ is aryl;

L$_2$ is absent; and

R$_2$ is absent.

4. A compound according to claim 1 wherein

L$_1$ is alkylene;

R$_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, and —CH=NOR$_{EE}$;

L$_2$ is absent; and

R$_2$ is absent.

88

5. A compound according to claim 1 wherein

A$_1$, A$_2$ and A$_3$ are each carboxy;

A$_4$, A$_5$, A$_6$, A$_7$, A$_8$, A$_9$, A$_{10}$ and A$_{11}$ are each hydrogen;

L$_1$ is alkylene wherein said alkylene is selected from the group consisting of —CH$_2$—, —CH$_2$CH$_2$— and —CH$_2$CH(CH$_3$)—;

R$_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$;

L$_2$ is absent; and

R$_2$ is absent.

6. A compound according to claim 5 selected from the group consisting of 5-({(4-chlorobenzyl)[(1S)-1,2,3,4-tetrahydro-1-naphthalenyl]amino}carbonyl)-1,2,4-benzenetricarboxylic acid;

5-({(4-bromobenzyl)[(1S)-1,2,3,4-tetrahydro-1-naphthalenyl]amino}carbonyl)-1,2,4-benzenetricarboxylic acid;

5-({(3-bromobenzyl)[(1S)-1,2,3,4-tetrahydro-1-naphthalenyl]amino}carbonyl)-1,2,4-benzenetricarboxylic acid;

5-({(3,4-dichlorobenzyl)[(1S)-1,2,3,4-tetrahydro-1-naphthalenyl]amino}carbonyl)-1,2,4-benzenetricarboxylic acid;

5-({(4-cyanobenzyl)[(1S)-1,2,3,4-tetrahydro-1-naphthalenyl]amino}carbonyl)-1,2,4-benzenetricarboxylic acid;

5-({(4-chloro-3-nitrobenzyl)[(1S)-1,2,3,4-tetrahydro-1-naphthalenyl]amino}carbonyl)-1,2,4-benzenetricarboxylic acid;

5-({[4-(dimethylamino)benzyl][(1S)-1,2,3,4-tetrahydro-1-naphthalenyl]amino}carbonyl)-1,2,4-benzenetricarboxylic acid;

5-({(3-chlorobenzyl)[(1S)-1,2,3,4-tetrahydro-1-naphthalenyl]amino}carbonyl)-1,2,4-benzenetricarboxylic acid;

5-({(3-cyanobenzyl)[(1S)-1,2,3,4-tetrahydro-1-naphthalenyl]amino}carbonyl)-1,2,4-benzenetricarboxylic acid;

5-({(2-phenylpropyl)[(1S)-1,2,3,4-tetrahydro-1-naphthalenyl]amino}carbonyl)-1,2,4-benzenetricarboxylic acid;

5-({(2-phenylethyl)[(1S)-1,2,3,4-tetrahydro-1-naphthalenyl]amino}carbonyl)-1,2,4-benzenetricarboxylic acid;

5-({benzyl[(1S)-1,2,3,4-tetrahydro-1-naphthalenyl]amino}carbonyl)-1,2,4-benzenetricarboxylic acid;

5-({(3-methoxybenzyl)[(1S)-1,2,3,4-tetrahydro-1-naphthalenyl]amino}carbonyl)-1,2,4-benzenetricarboxylic acid;

5-({(3-nitrobenzyl)[(1S)-1,2,3,4-tetrahydro-1-naphthalenyl]amino}carbonyl)-1,2,4-benzenetricarboxylic acid;

5-({[spiro[1,3-benzodioxol-5-yl-2,1'-cyclohexane]methyl][(1S)-1,2,3,4-tetrahydro-1-naphthalenyl]amino}carbonyl)-1,2,4-benzenetricarboxylic acid;

5-({[3-(allyloxy)benzyl][(1S)-1,2,3,4-tetrahydro-1-naphthalenyl]amino}carbonyl)-1,2,4-benzenctricarboxylic acid;

5-({[3,5-bis(trifluoromethyl)benzyl][(1S)-1,2,3,4-tetrahydro-1-naphthalenyl]amino}carbonyl)-1,2,4-benzenetricarboxylic acid;

5-({(1S)-1,2,3,4-tetrahydro-1-naphthalenyl[3-(trifluoromethyl)benzyl]amino}carbonyl)-1,2,4-benzenetricarboxylic acid;

5-({(3,5-difluorobenzyl)[(1S)-1,2,3,4-tetrahydro-1-naphthalenyl]amino}carbonyl)-1,2,4-benzenetricarboxylic acid;

-({[4-fluoro-3-(trifluoromethyl)benzyl][(1S)-1,2,3,4-tetrahydro-1-naphthalenyl]amino}carbonyl)-1,2,4-benzenetricarboxylic acid;

5-({(3,5-dibromobenzyl)[(1S)-1,2,3,4-tetrahydro-1-naphthalenyl]amino}carbonyl)-1,2,4-benzenetricarboxylic acid;

5-({[3-fluoro-5-(trifluoromethyl)benzyl][(1S)-1,2,3,4-tetrahydro-1-naphthalenyl]amino}carbonyl)-1,2,4-benzenetricarboxylic acid;

5-({(3,5-dimethoxybenzyl)[(1S)-1,2,3,4-tetrahydro-1-naphthalenyl]amino}carbonyl)-1,2,4-benzenetricarboxylic acid;

5-({(2,3-dichlorobenzyl)[(1S)-1,2,3,4-tetrahydro-1-naphthalenyl]amino}carbonyl)-1,2,4-benzenetricarboxylic acid;

5-({(2,4-dichlorobenzyl)[(1S)-1,2,3,4-tetrahydro-1-naphthalenyl]amino}carbonyl)-1,2,4-benzenetricarboxylic acid;

5-({(3,5-dimethylbenzyl)[(1S)-1,2,3,4-tetrahydro-1-naphthalenyl]amino}carbonyl)-1,2,4-benzenetricarboxylic acid;

-[((1S)-1,2,3,4-tetrahydro-1-naphthalenyl{3-[(trifluoromethyl)sulfanyl]benzyl}amino)carbonyl]-1,2,4-benzenetricarboxylic acid;

5-({[3-(methylsulfanyl)benzyl][(1S)-1,2,3,4-tetrahydro-1-naphthalenyl]amino}carbonyl)-1,2,4-benzenetricarboxylic acid;

5-({{3-[(methoxyimino)methyl]benzyl}[(1S)-1,2,3,4-tetrahydro-1-naphthalenyl]amino}carbonyl)-1,2,4-benzenetricarboxylic acid;

-({[3-(hydroxymethyl)benzyl][(1S)-1,2,3,4-tetrahydro-1-naphthalenyl]amino}carbonyl)-1,2,4-benzenetricarboxylic acid;

5-(-{3-formylbenzyl)[(1S)-1,2,3,4-tetrahydro-1-naphthalenyl]amino}carbonyl)-1,2,4-benzenetricarboxylic acid;

5-({{3-[(tert-butoxyimino)methyl]benzyl}[(1S)-1,2,3,4-tetrahydro-1-naphthalenyl]amino}carbonyl)-1,2,4-benzenetricarboxylic acid; and 5-({{3-[(isopropoxyimino)methyl]benzyl}[(1S)-1,2,3,4-tetrahydro-1-naphthalenyl]amino}carbonyl)-1,2,4-benzenetricarboxylic acid.

7. A compound according to claim 1 wherein $L_1$ is alkylene;

$R_1$ is aryl wherein said aryl is fluorenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxy, hydroxyalkyl, nitro, oxo, and —$NR_ER_F$;

$L_2$ is absent; and $R_2$ is absent.

8. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is fluorenyl substituted with 0 or 1 substituents selected from the group consisting of hydroxy and oxo;

$L_2$ is absent; and $R_2$ is absent.

9. A compound according to claim 8 selected from the group consisting of 5-({(9H-fluoren-2-ylmethyl)[(1S)-1,2,3,4-tetrahydro-1-naphthalenyl]amino}carbonyl)-1,2,4-benzenetricarboxylic acid;

5-({[(9-hydroxy-9H-fluoren-2-yl)methyl][(1S)-1,2,3,4-tetrahydro-1-naphthalenyl]amino}carbonyl)-1,2,4-benzenetricarboxylic acid; and 5-({[(9-oxo-9H-fluoren-2-yl)methyl][(1S)-1,2,3,4-tetrahydro-1-naphthalenyl]amino}carbonyl)-1,2,4-benzenetricarboxylic acid.

10. A compound according to claim 1 wherein $L_1$ is alkylene;

$R_1$ is aryl;

$L_2$ is a covalent bond; and $R_2$ is aryl.

11. A compound according to claim 1 wherein $L_1$ is alkylene;

$R_1$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —$CH=NOR_{EE}$;

$L_2$ is a covalent bond; and $R_2$ is aryl wherein said aryl is phenyl substituted with 0, 1, 2, 3, 4 or 5 substituents each independently selected from alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —$CH=NOR_{EE}$.

12. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, and —$NR_ER_F$;

$L_2$ is a covalent bond; and $R_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$.

13. A compound according to claim 12 selected from the group consisting of 5-({([1,1'-biphenyl]-4-ylmethyl)[(1S)-1,2,3,4-tetrahydro-1-naphthalenyl]amino}carbonyl)-1,2,4-benzenetricarboxylic acid;

5-({[(2'-chloro[1,1'-biphenyl]-4-yl)methyl][(1S)-1,2,3,4-tetrahydro-1-naphthalenyl]amino}carbonyl)-1,2,4-benzenetricarboxylic acid;

5-({[(3',5'-dichloro[1,1'-biphenyl]-4-yl)methyl][(1S)-1,2,3,4-tetrahydro-1-naphthalenyl]amino}carbonyl)-1,2,4-benzenetricarboxylic acid;

5-({[(2'-methoxy[1,1'-biphenyl]-4-yl)methyl][(1S)-1,2,3,4-tetrahydro-1-naphthalenyl]amino}carbonyl)-1,2,4-benzenetricarboxylic acid;

5-({[(4'-chloro[1,1'-biphenyl]-4-yl)methyl][(1S)-1,2,3,4-tetrahydro-1-naphthalenyl]amino}carbonyl)-1,2,4-benzenetricarboxylic acid;

5-({[(4'-fluoro[1,1'-biphenyl]-4-yl)methyl][(1S)-1,2,3,4-tetrahydro-1-naphthalenyl]amino}carbonyl)-1,2,4-benzenetricarboxylic acid;

5-({[(4'-methoxy[1,1'-biphenyl]-4-yl)methyl][(1S)-1,2,3,4-tetrahydro-1-naphthalenyl]amino}carbonyl)-1,2,4-benzenetricarboxylic acid;

5-[((1S)-1,2,3,4-tetrahydro-1-naphthalenyl{[2'-(trifluoromethyl)[1,1'-biphenyl]-4-yl]methyl}amino)carbonyl]-1,2,4-benzenetricarboxylic acid;

5-({[(2'-methyl[1,1'-biphenyl]-4-yl)methyl][(1S)-1,2,3,4-tetrahydro-1-naphthalenyl]amino}carbonyl)-1,2,4-benzenetricarboxylic acid;

5-[((1S)-1,2,3,4-tetrahydro-1-naphthalenyl{[4'-(trifluoromethyl)[1,1'-biphenyl]-2-yl]methyl}amino)carbonyl]-1,2,4-benzenetricarboxylic acid;

5-({[(4'-fluoro[1,1'-biphenyl]-2-yl)methyl][(1S)-1,2,3,4-tetrahydro-1-naphthalenyl]amino}carbonyl)-1,2,4-benzenetricarboxylic acid;

5-({[(4'-fluoro[1,1'-biphenyl]-3-yl)methyl][(1S)-1,2,3,4-tetrahydro-1-naphthalenyl]amino}carbonyl)-1,2,4-benzenetricarboxylic acid;

5-[((1S)-1,2,3,4-tetrahydro-1-naphthalenyl{[4'-(trifluoromethyl)[1,1'-biphenyl]-4-yl]methyl}amino)carbonyl]-1,2,4-benzenetricarboxylic acid;

5-({([1,1'-biphenyl]-2-ylmethyl)[(1S)-1,2,3,4-tetrahydro-1-naphthalenyl]amino}carbonyl)-1,2,4-benzenetricarboxylic acid;

5-({([1,1'-biphenyl]-3-ylmethyl)[(1S)-1,2,3,4-tetrahydro-1-naphthalenyl]amino}carbonyl)-1,2,4-benzenetricarboxylic acid;

5-({[(2-methyl[1,1'-biphenyl]-3-yl)methyl][(1S)-1,2,3,4-tetrahydro-1-naphthalenyl]amino}carbonyl)-1,2,4-benzenetricarboxylic acid;

5-[((1S)-1,2,3,4-tetrahydro-1-naphthalenyl{[4'-(trifluoromethyl)[1,1'-biphenyl]-3-yl]methyl}amino)carbonyl]-1,2,4-benzenetricarboxylic acid;

5-({[(5'-fluoro-2'-methoxy[1,1'-biphenyl]-3-yl)methyl][(1S)-1,2,3,4-tetrahydro-1-naphthalenyl]amino}carbonyl)-1,2,4-benzenetricarboxylic acid;

5-({[(5'-chloro-2'-methoxy[1,1'-biphenyl]-3-yl)methyl][(1S)-1,2,3,4-tetrahydro-1-naphthalenyl]amino}carbonyl)-1,2,4-benzenetricarboxylic acid;

5-({[(3',5'-dichloro[1,1'-biphenyl]-3-yl)methyl][(1S)-1,2,3,4-tetrahydro-1-naphthalenyl]amino}carbonyl)-1,2,4-benzenetricarboxylic acid;

5-({[(2'-methoxy[1,1'-biphenyl]-3-yl)methyl][(1S)-1,2,3,4-tetrahydro-1-naphthalenyl]amino}carbonyl)-1,2,4-benzenetricarboxylic acid;

5-({[(2'-chloro[1,1'-biphenyl]-3-yl)methyl][(1S)-1,2,3,4-tetrahydro-1-naphthalenyl]amino}carbonyl)-1,2,4-benzenetricarboxylic acid;

5-({[(2',5'-dimethoxy[1,1'-biphenyl]-3-yl)methyl][(1S)-1,2,3,4-tetrahydro-1-naphthalenyl]amino}carbonyl)-1,2,4-benzenetricarboxylic acid;

5-({[(3'-chloro[1,1'-biphenyl]-3-yl)methyl][(1S)-1,2,3,4-tetrahydro-1-naphthalenyl]amino}carbonyl)-1,2,4-benzenetricarboxylic acid;

5-({[(3',4'-dichloro[1,1'-biphenyl]-3-yl)methyl][(1S)-1,2,3,4-tetrahydro-1-naphthalenyl]amino}carbonyl)-1,2,4-benzenetricarboxylic acid;

5-({[(3'-chloro-4'-fluoro[1,1'-biphenyl]-3-yl)methyl][(1S)-1,2,3,4-tetrahydro-1-naphthalenyl]amino}carbonyl)-1,2,4-benzenetricarboxylic acid;

5-({[(3'-nitro[1,1'-biphenyl]-3-yl)methyl][(1S)-1,2,3,4-tetrahydro-1-naphthalenyl]amino}carbonyl)-1,2,4-benzenetricarboxylic acid;

5-({[(3'-methoxy[1,1'-biphenyl]-3-yl)methyl][(1S)-1,2,3,4-tetrahydro-1-naphthalenyl]amino}carbonyl)-1,2,4-benzenetricarboxylic acid;

5-({[(4'-chloro[1,1'-biphenyl]-3-yl)methyl][(1S)-1,2,3,4-tetrahydro-1-naphthalenyl]amino}carbonyl)-1,2,4-benzenetricarboxylic acid; and 5-({(1S)-1,2,3,4-tetrahydro-1-naphthalenyl[(3',4',5'-trimethoxy[1,1'-biphenyl]-3-yl)methyl]amino}carbonyl)-1,2,4-benzenetricarboxylic acid.

14. A compound according to claim 1 wherein $L_1$ is alkylene;

$R_1$ is aryl;

$L_2$ is alkylene; and $R_2$ is aryl.

15. A compound according to claim 1 wherein $L_1$ is alkylene;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, and —CH=NOR$_{EE}$;

$L_2$ is alkylene; and $R_2$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, and —CH=NOR$_{EE}$.

16. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$;

$L_2$ is alkylene wherein said alkylene is —$CH_2$—; and $R_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$.

17. A compound according to claim 16 that is 5-({(3-benzylbenzyl)[(1S)-1,2,3,4-tetrahydro-1-naphthalenyl]amino}carbonyl)-1,2,4-benzenetricarboxylic acid.

18. A compound according to claim 1 wherein $L_1$ is alkylene;

$R_1$ is aryl;

$L_2$ is —$(CH_2)_pO(CH_2)_q$—; and $R_2$ is aryl.

19. A compound according to claim 1 wherein $L_1$ is alkylene;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —CH=$NOR_{EE}$;

$L_2$ is —$(CH_2)_pO(CH_2)_q$—; and $R_2$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —CH=$NOR_{EE}$.

20. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$;

$L_2$ is —$(CH_2)_pO(CH_2)_q$—;

p is 0;

q is 0; and $R_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$.

21. A compound according to claim 20 selected from the group consisting of 5-({[3-(4-chlorophenoxy)benzyl][(1S)-1,2,3,4-tetrahydro-1-naphthalenyl]amino}carbonyl)-1,2,4-benzenetricarboxylic acid;

5-[((1S)-1,2,3,4-tetrahydro-1-naphthalenyl{3-[3-(trifluoromethyl)phenoxy]benzyl}amino)carbonyl]-1,2,4-benzenetricarboxylic acid;

5-({[3-(4-methoxyphenoxy)benzyl][(1S)-1,2,3,4-tetrahydro-1-naphthalenyl]amino}carbonyl)-1,2,4-benzenetricarboxylic acid;

5-({[3-(3,4-dichlorophenoxy)benzyl][(1S)-1,2,3,4-tetrahydro-1-naphthalenyl]amino}carbonyl)-1,2,4-benzenetricarboxylic acid;

5-({[3-(4-chlorophenoxy)benzyl][(1S)-1,2,3,4-tetrahydro-1-naphthalenyl]amino}carbonyl)-1,2,4-benzenetricarboxylic acid;

5-({[3-(4-tert-butylphenoxy)benzyl][(1S)-1,2,3,4-tetrahydro-1-naphthalenyl]amino}carbonyl)-1,2,4-benzenetricarboxylic acid;

5-({[3-(4-methylphenoxy)benzyl][(1S)-1,2,3,4-tetrahydro-1-naphthalenyl]amino}carbonyl)-1,2,4-benzenetricarboxylic acid;

5-({[3-(3,5-dichlorophenoxy)benzyl][(1S)-1,2,3,4-tetrahydro-1-naphthalenyl]amino}carbonyl)-1,2,4-benzenetricarboxylic acid;

5-({[3-(4-nitrophenoxy)benzyl][(1S)-1,2,3,4-tetrahydro-1-naphthalenyl]amino}carbonyl)-1,2,4-benzenetricarboxylic acid;

5-({[3-(4-cyanophenoxy)benzyl][(1S)-1,2,3,4-tetrahydro-1-naphthalenyl]amino}carbonyl)-1,2,4-benzenetricarboxylic acid; and 5-({[3-(4-fluorophenoxy)benzyl][(1S)-1,2,3,4-tetrahydro-1-naphthalenyl]amino}carbonyl)-1,2,4-benzenetricarboxylic acid.

22. A compound according to claim 20 that is 5-({(3-phenoxybenzyl)[(1S)-1,2,3,4-tetrahydro-1-naphthalenyl]amino}carbonyl)-1,2,4-benzenetricarboxylic acid.

23. A compound according to claim 1 wherein $A_1$ and $A_2$ are each independently selected from the group consisting of alkoxycarbonyl, carboxy, hydroxy, ($NR_AR_B$)carbonyl, and —$S(O)_2OH$;

$A_3$ is carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$;

$L_2$ is —$(CH_2)_pO(CH_2)_q$—;

p is 0;

q is 0; and

R$_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$.

24. A compound according to claim 23 selected from the group consisting of

2-[(methylamino)carbonyl]-5-({(3-phenoxybenzyl)[(1S)-1,2,3,4-tetrahydro-1-naphthalenyl]amino}carbonyl) terephthalic acid;

4-[(methylamino)carbonyl]-6-({(3-phenoxybenzyl)[(1S)-1,2,3,4-tetrahydro-1-naphthalenyl]amino}carbonyl) isophthalic acid;

2-[(cyanoamino)carbonyl]-5-({(3-phenoxybenzyl)[(1S)-1,2,3,4-tetrahydro-1-naphthalenyl]amino}carbonyl) terephthalic acid;

4-[(cyanoamino)carbonyl]-6-({(3-phenoxybenzyl)[(1S)-1,2,3,4-tetrahydro-1-naphthalenyl]amino}carbonyl) isophthalic acid;

2-(aminocarbonyl)-5-({(3-phenoxybenzyl)[(1S)-1,2,3,4-tetrahydro-1-naphthalenyl]amino}carbonyl) terephthalic acid;

4-(aminocarbonyl)-6-({(3-phenoxybenzyl)[(1S)-1,2,3,4-tetrahydro-1-naphthalenyl]amino}carbonyl)isophthalic acid;

2-(methoxycarbonyl)-5-({(3-phenoxybenzyl)[(1S)-1,2,3,4-tetrahydro-1-naphthalenyl]amino}carbonyl) terephthalic acid;

4-(methoxycarbonyl)-6-({(3-phenoxybenzyl)[(1S)-1,2,3,4-tetrahydro-1-naphthalenyl]amino}carbonyl) isophthalic acid;

2-hydroxy-5-({(3-phenoxybenzyl)[(1S)-1,2,3,4-tetrahydro-1-naphthalenyl]amino}carbonyl) terephthalic acid;

4-hydroxy-6-({(3-phenoxybenzyl)[(1S)-1,2,3,4-tetrahydro-1-naphthalenyl]amino}carbonyl)isophthalic acid;

2-({(3-phenoxybenzyl)[(1S)-1,2,3,4-tetrahydro-1-naphthalenyl]amino}carbonyl)-5-sulfoterephthalic acid; and 4-({(3-phenoxybenzyl)[(1S)-1,2,3,4-tetrahydro-1-naphthalenyl]amino}carbonyl)-6-sulfoisophthalic acid.

25. A compound according to claim 1 wherein

A$_1$ and A$_2$ are each independently selected from the group consisting of carboxy and —NR$_C$S(O)$_2$R$_D$ wherein one of A$_1$ or A$_2$ is —NR$_C$S(O)$_2$R$_D$;

A$_3$ is carboxy;

A$_4$, A$_5$, A$_6$, A$_7$, A$_8$, A$_9$, A$_{10}$ and A$_{11}$ are each hydrogen;

L$_1$ is alkylene wherein said alkylene is —CH$_2$—;

R$_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, and —CH=NOR$_{EE}$;

L$_2$ is —(CH$_2$)$_p$O(CH$_2$)$_q$—;

p is 0;

q is 0; and

R$_2$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, and —CH=NOR$_{EE}$.

26. A compound according to claim 1 wherein

A$_1$ and A$_2$ are each independently selected from the group consisting of carboxy and —NR$_C$S(O)$_2$R$_D$ wherein one of A$_1$ or A$_2$ is —NR$_C$S(O)$_2$R$_D$;

A$_3$ is carboxy;

A$_4$, A$_5$, A$_6$, A$_7$, A$_8$, A$_9$, A$_{10}$ and A$_{11}$ are each hydrogen;

L$_1$ is alkylene wherein said alkylene is —CH$_2$—;

R$_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$;

L$_2$ is —(CH$_2$)$_p$O(CH$_2$)$_q$—;

p is 0;

q is 0;

R$_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$; and R$_D$ is selected from the group consisting of alkyl and aryl.

27. A compound according to claim 1 wherein

A$_1$ and A$_2$ are each independently selected from the group consisting of carboxy and —NR$_C$S(O)$_2$R$_D$ wherein one of A$_1$ or A$_2$ is —NR$_C$S(O)$_2$R$_D$;

A$_3$ is carboxy;

A$_4$, A$_5$, A$_6$, A$_7$, A$_8$, A$_9$, A$_{10}$ and A$_{11}$ are each hydrogen;

L$_1$ is alkylene wherein said alkylene is —CH$_2$—;

R$_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$;

L$_2$ is —(CH$_2$)$_p$O(CH$_2$)$_q$—;

p is 0;

q is 0;

R$_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$; and R$_D$ is selected from the group consisting of alkyl and aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, —NR$_E$R$_F$, and —N(R$_A$)C(O)NR$_B$R$_C$.

28. A compound according to claim 27 selected from the group consisting of 4-({[(4-methoxyphenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(4-methoxyphenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(3-chloro-4-methylphenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(3-chloro-4-methylphenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(2-chlorophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(2-chlorophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(3-chlorophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(3-chlorophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(4-chlorophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(4-chlorophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(4-nitrophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(4-nitrophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(4-bromophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(4-bromophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(3-nitrophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(3-nitrophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(phenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(phenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(2-nitrophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(2-nitrophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(2-methylphenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(2-methylphenyl)sulfonyl]amino}carbonyl)-5-({(3-phenoxybenzyl)[(1S)-1,2,3,4-tetrahydro-1-naphthalenyl]amino}carbonyl)terephthalic acid;

4-{[({4-[(2,3-dihydroxypropyl)amino]phenyl}sulfonyl)amino]carbonyl}-6-({(3-phenoxybenzyl)[(1S)-1,2,3,4-tetrahydro-1-naphthalenyl]amino}carbonyl)isophthalic acid;

2-{[({4-[(2,3-dihydroxypropyl)amino]phenyl}sulfonyl)amino]carbonyl}-5-({(3-phenoxybenzyl)[(1S)-1,2,3,4-tetrahydro-1-naphthalenyl]amino}carbonyl)terephthalic acid;

2-({[(4-{[(methylamino)carbonyl]amino}phenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(4-{[(methylamino)carbonyl]amino}phenyl)sulfonyl]amino}carbonyl)-6-({(3-phenoxybenzyl)[(1S)-1,2,3,4-tetrahydro-1-naphthalenyl]amino}carbonyl)isophthalic acid;

4-[({[4-(butyrylamino)phenyl]sulfonyl}amino)carbonyl]-6-({(3-phenoxybenzyl)[(1S)-1,2,3,4-tetrahydro-1-naphthalenyl]amino}carbonyl)isophthalic acid;

2-[({[4-(butyrylamino)phenyl]sulfonyl}amino)carbonyl]-5-({(3-phenoxybenzyl)[(1S)-1,2,3,4-tetrahydro-1-naphthalenyl]amino}carbonyl)terephthalic acid;

4-({[(3,4-difluorophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(3,4-difluorophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(2,5-difluorophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(2,5-difluorophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(2-methoxy-4-methylphenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(2-methoxy-4-methylphenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(4-methylphenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(4-methylphenyl)sulfonyl]amino}carbonyl)-5-({(3-phenoxybenzyl)[(1S)-1,2,3,4-tetrahydro-1-naphthalenyl]amino}carbonyl)terephthalic acid;

2-({[(2-fluorophenyl)sulfonyl]amino}carbonyl)-5-({(3-phenoxybenzyl)[(1S)-1,2,3,4-tetrahydro-1-naphthalenyl]amino}carbonyl)terephthalic acid;

4-({[(2-fluorophenyl)sulfonyl]amino}carbonyl)-6-({(3-phenoxybenzyl)[(1S)-1,2,3,4-tetrahydro-1-naphthalenyl]amino}carbonyl)isophthalic acid;

2-({[(4-hydroxyphenyl)sulfonyl]amino}carbonyl)-5-({(3-phenoxybenzyl)[(1S)-1,2,3,4-tetrahydro-1-naphthalenyl]amino}carbonyl)terephthalic acid; and 4-({[(4-hydroxyphenyl)sulfonyl]amino}carbonyl)-6-({(3-phenoxybenzyl)[(1S)-1,2,3,4-tetrahydro-1-naphthalenyl]amino}carbonyl)isophthalic acid.

29. A compound according to claim 1 wherein $A_1$ and $A_2$ are each independently selected from the group consisting of carboxy and —$NR_CS(O)_2R_D$ wherein one of $A_1$ or $A_2$ is —$NR_CS(O)_2R_D$;

$A_3$ is carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —CH=$NOR_{EE}$;

$L_2$ is —$(CH_2)_pO(CH_2)_q$—;

p is 0;

q is 0;

$R_2$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —CH=$NOR_{EE}$; and $R_D$ is arylalkyl.

30. A compound according to claim 1 wherein $A_1$ and $A_2$ are each independently selected from the group consisting of carboxy and —$NR_CS(O)_2R_D$ wherein one of $A_1$ or $A_2$ is —$NR_CS(O)_2R_D$;

$A_3$ is carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$;

$L_2$ is —$(CH_2)_pO(CH_2)_q$—;

p is 0;

q is 0;

$R_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$; and $R_D$ is arylalkyl wherein the aryl of arylalkyl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$.

31. A compound according to claim 30 selected from the group consisting of

4-{[(benzylsulfonyl)amino]carbonyl}-6-({(3-phenoxybenzyl)[(1S)-1,2,3,4-tetrahydro-1-naphthalenyl]amino}carbonyl)isophthalic acid; and 2-{[(benzylsulfonyl)amino]carbonyl}-5-({(3-phenoxybenzyl)[(1S)-1,2,3,4-tetrahydro-1-naphthalenyl]amino}carbonyl)terephthalic acid.

32. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$;

$L_2$ is —$(CH_2)_pO(CH_2)_q$—;

p is 0;

q is 1; and $R_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=$NOR_{EE}$, and —$NR_ER_F$.

33. A compound according to claim 32 that is 5-({[3-(benzyloxy)benzyl][(1S)-1,2,3,4-tetrahydro-1-naphthalenyl]amino}carbonyl)-1,2,4-benzenetricarboxylic acid.

34. A compound according to claim 1 wherein $L_1$ is alkylene;

$R_1$ is aryl;

$L_2$ is —$(CH_2)_pO(CH_2)_q$—; and $R_2$ is cycloalkyl.

35. A compound according to claim 1 wherein $L_1$ is alkylene;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —CH=$NOR_{EE}$;

$L_2$ is —$(CH_2)_pO(CH_2)_q$—; and $R_2$ is cycloalkyl.

36. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$;

$L_2$ is —$(CH_2)_pO(CH_2)_q$—;

p is 0;

q is 0; and $R_2$ is cycloalkyl.

37. A compound according to claim 36 selected from the group consisting of 5-({[3-(cyclohexyloxy)benzyl][(1S)-1,2,3,4-tetrahydro-1-naphthalenyl]amino}carbonyl)-1,2,4-benzenetricarboxylic acid; and 5-({{3-[exo-bicyclo[2.2.1]hept-2-yloxy]benzyl}[(1S)-1,2,3,4-tetrahydro-1-naphthalenyl]amino}carbonyl)-1,2,4-benzenetricarboxylic acid.

38. A compound according to claim 1 wherein $L_1$ is alkylene;

$R_1$ is aryl;

$L_2$ is —$(CH_2)_pO(CH_2)_q$—; and $R_2$ is cycloalkenyl.

39. A compound according to claim 1 wherein $L_1$ is alkylene;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, and —CH=NOR$_{EE}$;

$L_2$ is —$(CH_2)_pO(CH_2)_q$—; and $R_2$ is cycloalkenyl.

40. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$;

$L_2$ is —$(CH_2)_pO(CH_2)_q$—;

p is 0;

q is 0; and $R_2$ is cycloalkenyl.

41. A compound according to claim 40 that is 5-({[3-(2-cyclohexen-1-yloxy)benzyl][(1S)-1,2,3,4-tetrahydro-1-naphthalenyl]amino}carbonyl)-1,2,4-benzenetricarboxylic acid.

42. A compound according to claim 1 wherein $L_1$ is alkylene;

$R_1$ is aryl;

$L_2$ is —$(CH_2)_pS(CH_2)_q$—; and $R_2$ is aryl.

43. A compound according to claim 1 wherein $L_1$ is alkylene;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, and —CH=NOR$_{EE}$;

$L_2$ is —$(CH_2)_pS(CH_2)_q$—; and $R_2$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —NR$_E$R$_F$, (NR$_E$R$_F$)carbonyl, —N(R$_A$)C(O)NR$_B$R$_C$, and —CH=NOR$_{EE}$.

44. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —CH=NOR$_{EE}$, and —NR$_E$R$_F$;

$L_2$ is —$(CH_2)_pS(CH_2)_q$—;

p is 0;

q is 0; and $R_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkyltlhio, halogen, hydroxyalkyl, methylenedioxy, nitro, —CH=NOR$_{EE}$, and —NR$_E$R$_F$.

45. A compound according to claim 44 selected from the group consisting of 5-({[3-(phenylsulfanyl)benzyl][(1S)-1,2,3,4-tetrahydro-1-naphthalenyl]amino}carbonyl)-1,2,4-benzenetricarboxylic acid;

5-({{3-[(4-methoxyphenyl)sulfanyl]benzyl}[(1S)-1,2,3,4-tetrahydro-1-naphthalenyl]amino}carbonyl)-1,2,4-benzenetricarboxylic acid;

5-({{3-[(4-nitrophenyl)sulfanyl]benzyl}[(1S)-1,2,3,4-tetrahydro-1-naphthalenyl]amino}carbonyl)-1,2,4-benzenetricarboxylic acid; and 5-({{3-[(4-chlorophenyl)sulfanyl]benzyl}[(1S)-1,2,3,4-tetrahydro-1-naphthalenyl]amino}carbonyl)-1,2,4-benzenetricarboxylic acid.

46. A compound according to claim 1 wherein $L_1$ is alkylene;

$R_1$ is aryl;

$L_2$ is —$(CH_2)_pC(O)(CH_2)_q$—; and $R_2$ is aryl.

47. A compound according to claim 1 wherein $L_1$ is alkylene;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —$CH=NOR_{EE}$;

$L_2$ is —$(CH_2)_pC(O)(CH_2)_q$—; and $R_2$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —$CH=NOR_{EE}$.

48. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, and —$NR_ER_F$;

$L_2$ is —$(CH_2)_pC(O)(CH_2)_q$—;

p is 0;

q is 0; and $R_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, and —$NR_ER_F$.

49. A compound according to claim 48 that is 5-({(3-benzoylbenzyl)[(1S)-1,2,3,4-tetrahydro-1-naphthalenyl]amino}carbonyl)-1,2,4-benzenetricarboxylic acid.

50. A compound according to claim 1 wherein $L_1$ is alkylene;

$R_1$ is aryl;

$L_2$ is —$(CH_2)_pC(OH)(CH_2)_q$—; and $R_2$ is aryl.

51. A compound according to claim 1 wherein $L_1$ is alkylene;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —$CH=NOR_{EE}$;

$L_2$ is —$(CH_2)_pC(OH)(CH_2)_q$—; and $R_2$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —$CH=NOR_{EE}$.

52. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, and —$NR_ER_F$;

$L_2$ is —$(CH_2)_pC(OH)(CH_2)_q$—;

p is 0;

q is 0; and $R_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, and —$NR_ER_F$.

53. A compound according to claim 52 that is 5-({{3-[hydroxy(phenyl)methyl]benzyl}[(1S)-1,2,3,4-tetrahydro-1-naphthalenyl]amino}carbonyl)-1,2,4-benzenetricarboxylic acid.

54. A compound according to claim 1 wherein $L_1$ is alkylene;

$R_1$ is aryl;

$L_2$ is —$(CH_2)_pCH=NO(CH_2)_q$—; and $R_2$ is aryl.

55. A compound according to claim 1 wherein $L_1$ is alkylene;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —$CH=NOR_{EE}$;

$L_2$ is —$(CH_2)_pCH=NO(CH_2)_q$—; and $R_2$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —$CH=NOR_{EE}$.

56. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is alkylene wherein said alkylene is —$CH_2$—;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, and —$NR_ER_F$;

$L_2$ is —$(CH_2)_pCH=NO(CH_2)_q$—;

p is 0;

q is an integer 0–1; and $R_2$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, and —$NR_ER_F$.

57. A compound according to claim 56 selected from the group consisting of 5-({{3-[(phenoxyimino)methyl]benzyl}[(1S)-1,2,3,4-tetrahydro-1-naphthalenyl]amino}carbonyl)-1,2,4-benzenetricarboxylic acid;

5-({(3-{[(benzyloxy)imino]methyl}benzyl)[(1S)-1,2,3,4-tetrahydro-1-naphthalenyl]amino}carbonyl)-1,2,4-benzenetricarboxylic acid;

5-({[3-({[(4-nitrobenzyl)oxy]imino}methyl)benzyl][(1S)-1,2,3,4-tetrahydro-1-naphthalenyl]amino}carbonyl)-1,2,4-benzenetricarboxylic acid; and 5-({[3-({[(2,3,4,5,6-pentafluorobenzyl)oxy]imino}methyl)benzyl][(1S)-1,2,3,4-tetrahydro-1-naphthalenyl]amino}carbonyl)-1,2,4-benzenetricarboxylic acid.

58. A compound according to claim 1 wherein $L_1$ is alkylene;

$R_1$ is cycloalkyl;

$L_2$ is absent; and $R_2$ is absent.

59. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is —$CH_2$—;

$R_1$ is cycloalkyl;

$L_2$ is absent; and $R_2$ is absent.

60. A compound according to claim 59 that is 5-({(cyclohexylmethyl)[(1S)-1,2,3,4-tetrahydro-1-naphthalenyl]amino}carbonyl)-1,2,4-benzenetricarboxylic acid.

61. A compound according to claim 1 wherein $L_1$ is —$(CH_2)_mO(CH_2)_n$—;

$R_1$ is aryl;

$L_2$ is absent; and $R_2$ is absent.

62. A compound according to claim 1 wherein $L_1$ is —$(CH_2)_mO(CH_2)_n$—;

$R_1$ is aryl wherein said aryl is phenyl substituted with 0, 1, 2, 3, 4 or 5 substituents each independently selected from the group consisting of alkenyl, alkenyloxy, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, alkynyloxy, carboxy, carboxyalkyl, cyano, cyanoalkyl, ethylenedioxy, formyl, haloalkoxy, haloalkyl, haloalkylthio, halogen, hydroxy, hydroxyalkyl, mercapto, methylenedioxy, nitro, oxo, —$NR_ER_F$, ($NR_ER_F$)carbonyl, —$N(R_A)C(O)NR_BR_C$, and —$CH=NOR_{EE}$;

$L_2$ is absent; and $R_2$ is absent.

63. A compound according to claim 1 wherein $A_1$, $A_2$ and $A_3$ are each carboxy;

$A_4$, $A_5$, $A_6$, $A_7$, $A_8$, $A_9$, $A_{10}$ and $A_{11}$ are each hydrogen;

$L_1$ is —$(CH_2)_mO(CH_2)_n$—;

m is an integer 2–4;

n is 0;

$R_1$ is aryl wherein said aryl is phenyl substituted with 0, 1, or 2 substituents selected from the group consisting of alkoxy, alkoxycarbonyl, alkenyl, alkenyloxy, alkyl, alkylthio, cyano, formyl, haloalkoxy, haloalkyl, haloalkylthio, halogen, hydroxyalkyl, methylenedioxy, nitro, —$CH=NOR_{EE}$, and —$NR_ER_F$;

$L_2$ is absent; and $R_2$ is absent.

64. A compound according to claim 63 that is 5-({(4-phenoxybutyl)[(1S)-1,2,3,4-tetrahydro-1-naphthalenyl]amino}carbonyl)-1,2,4-benzenetricarboxylic acid.

65. A pharmaceutical composition comprising a therapeutically effective amount of a compound according to claim 1 or a pharmaceutically acceptable salt thereof in combination with a pharmaceutically acceptable carrier.

66. A method of treating bladder overactivity in a host mammal in need of such treatment comprising administering a therapeutically effective amount of a compound according to claim 1 or a pharmaceutically acceptable salt thereof.

67. A method of treating urinary incontinence in a host mammal in need of such treatment comprising administering a therapeutically effective amount of a compound according to claim 1 or a pharmaceutically acceptable salt thereof.

68. A method of treating pain in a mammal comprising administering to a mammal in need of such treatment a therapeutically effective amount of a compound according to claim 1 or a pharmaceutically acceptable salt thereof.

* * * * *

UNITED STATES PATENT AND TRADEMARK OFFICE
CERTIFICATE OF CORRECTION

PATENT NO. : 6,831,193 B2 Page 1 of 1
APPLICATION NO. : 10/141989
DATED : December 14, 2004
INVENTOR(S) : Chih-Hung Lee et al.

It is certified that error appears in the above-identified patent and that said Letters Patent is hereby corrected as shown below:

Col. 86, Line 42, add "and tetrazolyl;" before "or".

Col. 86, Line 46, add "and tetrazolyl;" after "-S(O)2OH".

Col. 87, Line 44, replace "and cycloalkenyl, cycloalkyl" with --cycloalkenyl and cycloalkyl--.

Col. 89, Line 10, add "5" at the start of this line.

Col. 89, Line 31, add "5" at the start of this line.

Col. 89, Line 40, add "5" at the start of this line.

Signed and Sealed this

Eighteenth Day of July, 2006

JON W. DUDAS
*Director of the United States Patent and Trademark Office*